US008906673B2

(12) United States Patent
Vu et al.

(10) Patent No.: US 8,906,673 B2
(45) Date of Patent: Dec. 9, 2014

(54) AUTOMATED DETECTION AND COUNTING OF BIOMOLECULES USING NANOPARTICLE PROBES

(75) Inventors: Tania Q. Vu, Portland, OR (US); Brian R. Long, Portland, OR (US); Benjamin K. Scholl, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 199 days.

(21) Appl. No.: 13/265,634

(22) PCT Filed: Apr. 29, 2010

(86) PCT No.: PCT/US2010/032965
§ 371 (c)(1),
(2), (4) Date: Oct. 21, 2011

(87) PCT Pub. No.: WO2010/127114
PCT Pub. Date: Nov. 4, 2010

(65) Prior Publication Data
US 2012/0046191 A1 Feb. 23, 2012

Related U.S. Application Data

(60) Provisional application No. 61/174,924, filed on May 1, 2009.

(51) Int. Cl.
C12M 1/34 (2006.01)
B82Y 15/00 (2011.01)
C40B 30/10 (2006.01)
G01N 33/58 (2006.01)
G01N 33/561 (2006.01)

(52) U.S. Cl.
CPC ............ *G01N 33/588* (2013.01); *G01N 33/561* (2013.01); *B82Y 15/00* (2013.01); *Y10S 977/904* (2013.01); *Y10S 977/778* (2013.01)
USPC ........... 435/288.7; 977/904; 977/778; 506/12

(58) Field of Classification Search
CPC .................................................... G01N 33/533
USPC ........................................... 506/7; 435/288.7
See application file for complete search history.

(56) References Cited

U.S. PATENT DOCUMENTS 7,309,568 B2 * 12/2007 Oshida et al. ................ 435/6.11
2002/0028457 A1 * 3/2002 Empedocles et al. ............. 435/6

(Continued)

FOREIGN PATENT DOCUMENTS

WO WO 2008/0151985 5/2008

OTHER PUBLICATIONS

Lagerholm et al. (Biophysical Journal, 2006, vol. 91, pp. 3050-3060).*
Casanova et al., "Counting the number of proteins coupled to single nanoparticles," *Journal of the American Chemical Society*, vol. 129, pp. 12592-12593, 2007.
Extended European Search Report issued Aug. 22, 2012 by the European Patent Office for EPC Patent Application No. 10770330.8 filed Apr. 29, 2010, 13 pp.

(Continued)

*Primary Examiner* — Christopher M Gross
*Assistant Examiner* — Richard L Manteuffel
(74) *Attorney, Agent, or Firm* — Klarquist Sparkman, LLP

(57) ABSTRACT

An apparatus and method for counting nanoparticle probes is disclosed. In one embodiment, quantum dot-tagged proteins on optically transparent membranes or slides are counted. The transparent membranes or slides are loaded onto a stage (e.g., an X-Y stage or X-Y-Z stage), which can automatically reposition the transparent membrane or slides for image capture at varying locations. A microscope can be used for providing a light source to fluoresce the nanocrystals and for providing the magnification needed for image capture. Once one or more images are captured, the nanoparticles can be automatically counted using post-processing software that maintains a total count across multiple images, if desired.

17 Claims, 25 Drawing Sheets

(56) References Cited

U.S. PATENT DOCUMENTS

| | | |
|---|---|---|
| 2005/0148100 A1 | 7/2005 | Su et al. |
| 2007/0111225 A1 | 5/2007 | Lambert et al. |
| 2007/0159624 A1 | 7/2007 | Resch-Genger et al. |
| 2008/0220982 A1 | 9/2008 | Vu et al. |
| 2009/0277791 A1* | 11/2009 | Vu et al. .................. 204/461 |
| 2010/0038559 A1* | 2/2010 | Feke et al. ............... 250/458.1 |

OTHER PUBLICATIONS

Scholl et al., "Single Particle Quantum Dot Imaging Achieves Ultrasensitive Detection Capabilities for Western Immunoblot Analysis," *ACS Nano*, vol. 3, No. 6, 11 pp., Jun. 23, 2009.

Tibbe et al., "Optical tracking and detection of immunomagnetically selected and aligned cells," *Nature Biotechnology*, vol. 17, 4 pp., Dec. 1999.

* cited by examiner

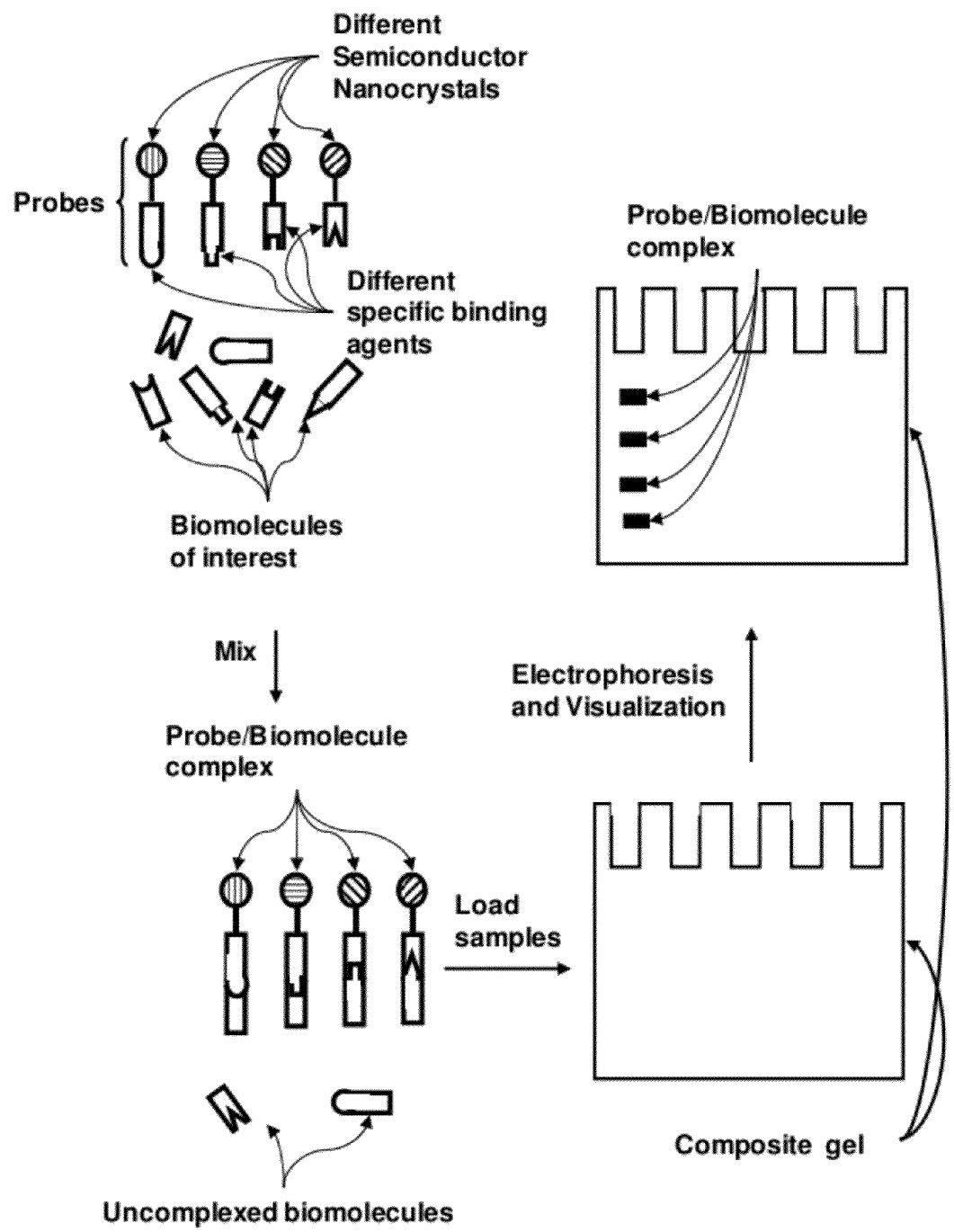

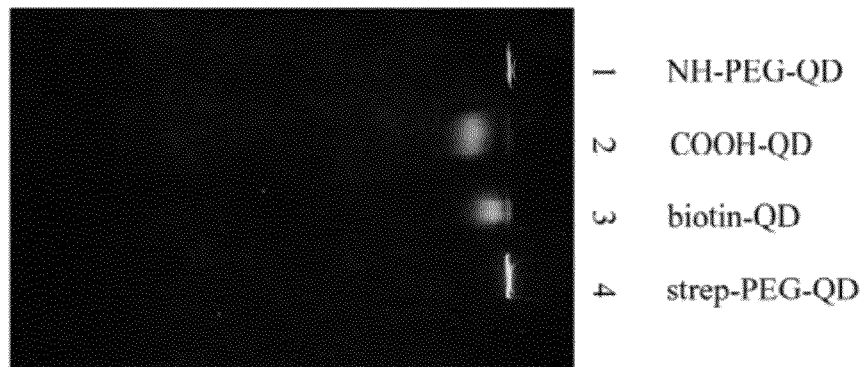
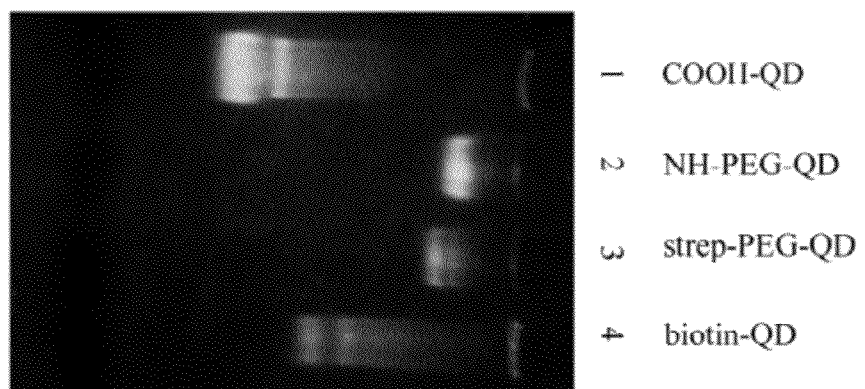
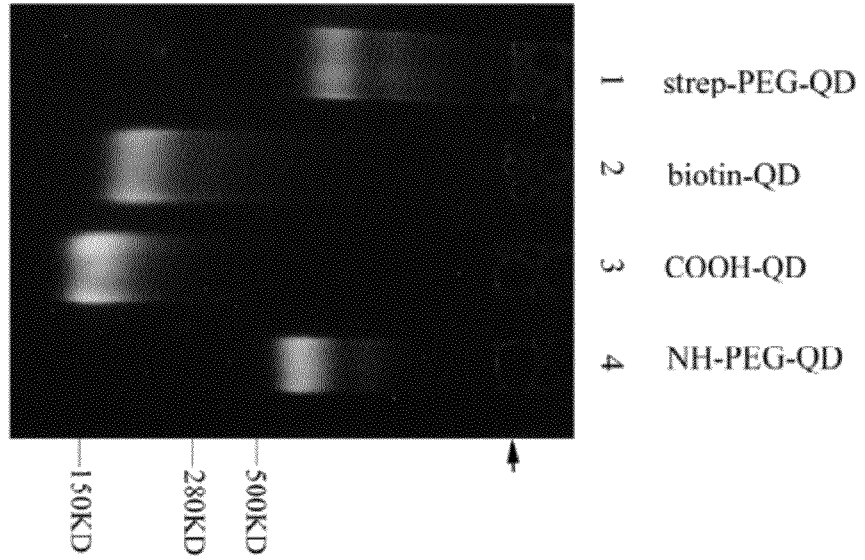

FIG. 8
A
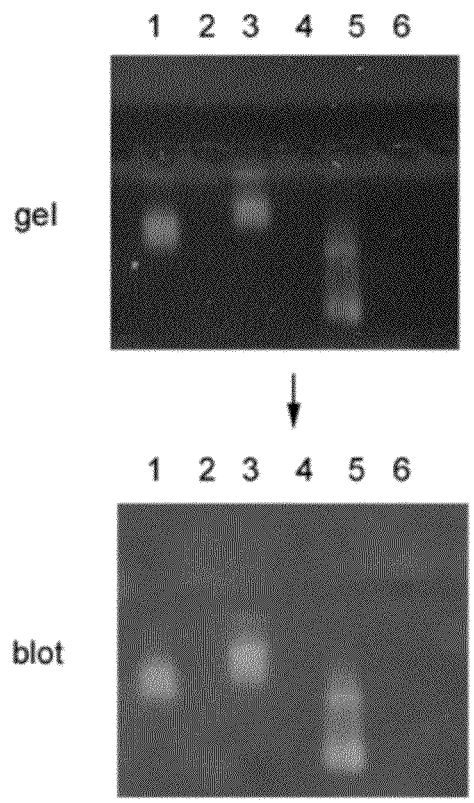
1 strep-QD585: 2.5nM
2 strep-QD585: 0.125nM
3 strep-QD655: 2.5nM
4 strep-QD655: 0.125nM
5 biotin-QD655: 2.5nM
6 biotin-QD655: 0.125nM
(2 uL/ lane)
Single QD detected in the band from Lane 4. Note this is not visible with traditional UV transillumination
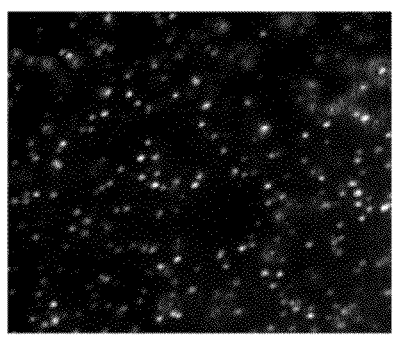

Figure 1 Gel Blot Identification of receptor complexes with single QD resolution Sensitive protein detection with conventional Western blot and QD tags

FIG. 21A
SPQD Western Blotting
SDS-PAGE Separation of Protein Sample
↓
Electrotransfer to PVDF Membrane
↓
Tag PVDF Membrane with Antibody-QD Probe
↓
Convert to Transparent PVDF Membrane
↓
Automated Imaging and Counting of Discrete QD Probe
FIG. 21B
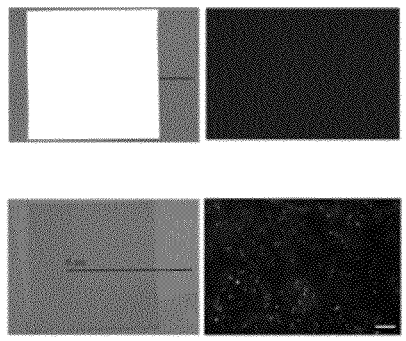
FIG. 21C
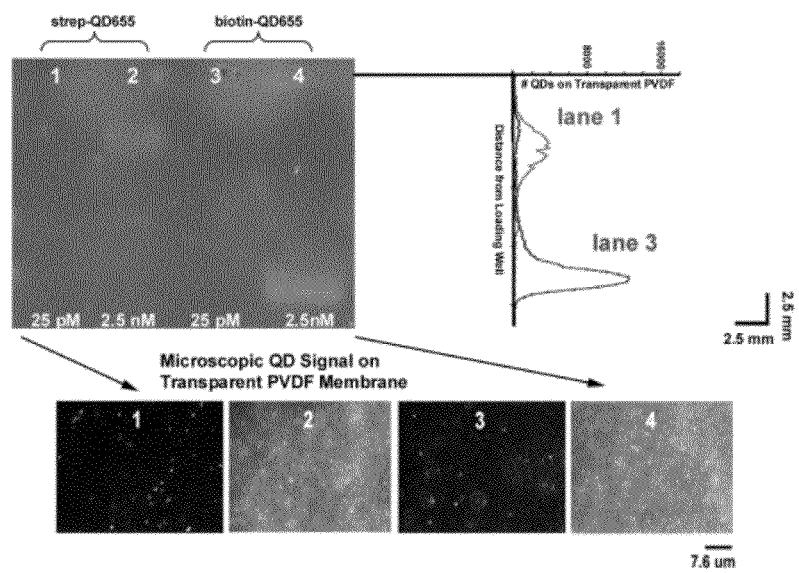

SPQD Western
NGF

Traditional Western
NGF

SPQD Western
Factor XI

Traditional Western
Factor XI

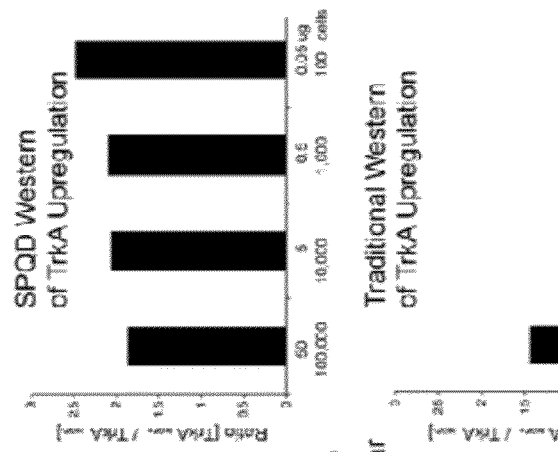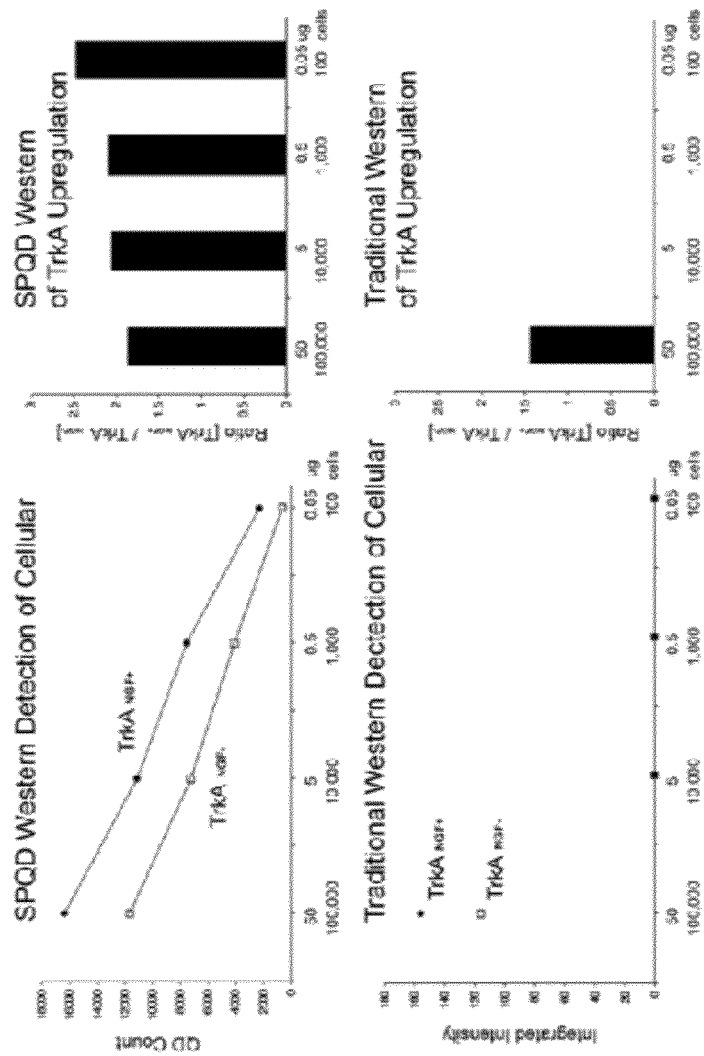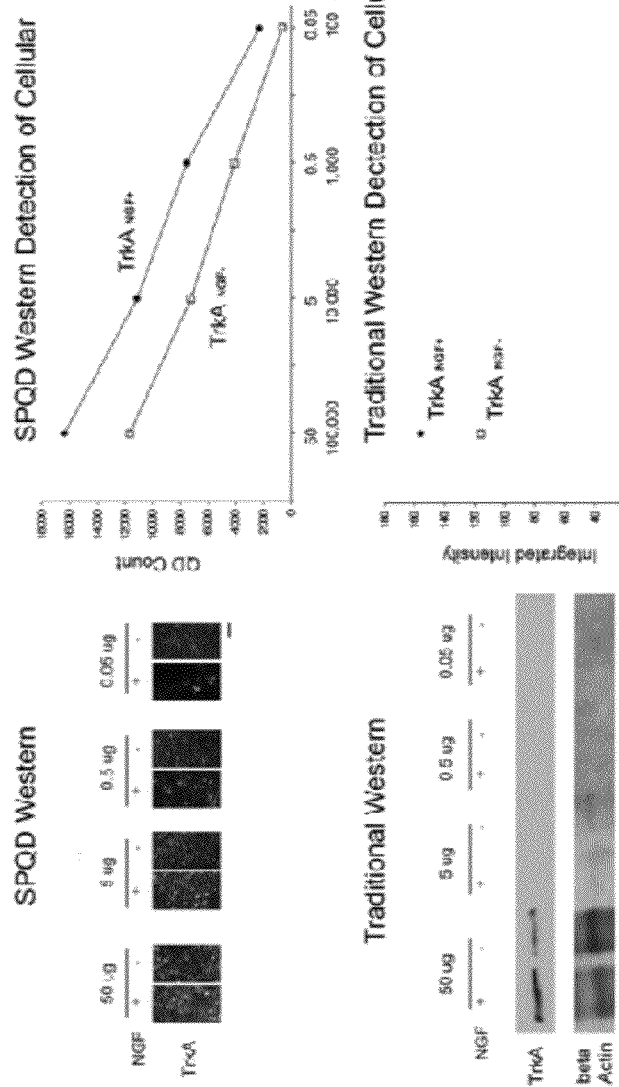

SPQD Detection of CrkL

Traditional Western

FIG. 25A
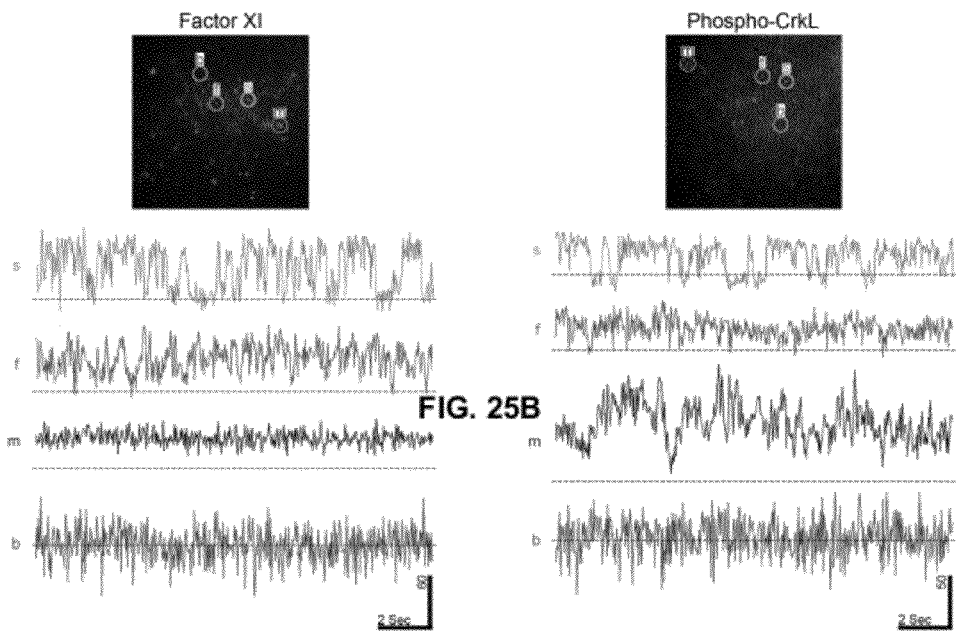
FIG. 25B
FIG. 25C
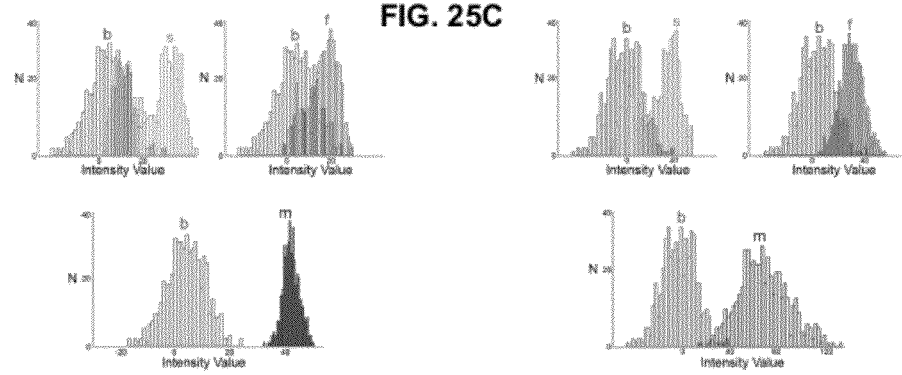
FIG. 25D
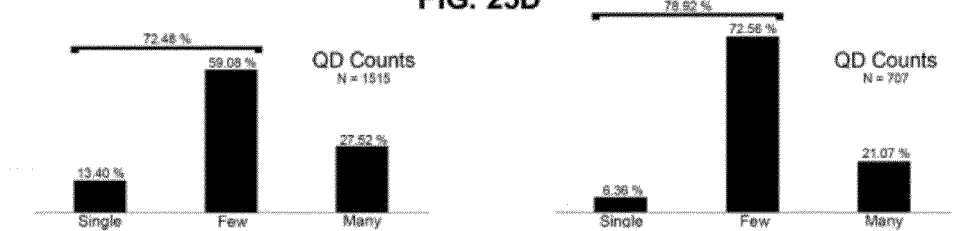

AUTOMATED DETECTION AND COUNTING OF BIOMOLECULES USING NANOPARTICLE PROBES

CROSS REFERENCE TO RELATED APPLICATIONS

This is the U.S. National Stage of International Application No, PCT/US2010/032965, filed Apr. 29, 2010, which was published in English under PCT Article 21 (2), which in turn claims the benefit of U.S. Provisional Application No. 61/174,924, filed May 1, 2009. The provisional application is incorporated by reference herein in its entirety.

FIELD

This disclosure relates to the field of detecting biomolecules. Specifically, this disclosure relates to methods for detecting and counting biomolecules using nanoparticle probes, such as quantum dots.

BACKGROUND

Quantum dots are fluorescent semiconductor nanoparticles. The fluorescence of semiconductor nanocrystals significantly exceeds the brightness and photostability of conventional fluorophores, such as organic dyes, typically used in molecular biological and biochemical applications (Chan and Nie, *Science* 281, 2016-2018, 1998; Bruchez et al., *Science* 281, 2013-2016, 1998). The novel optical properties of semiconductor nanocrystals allow for ultrasensitive detection and quantification of semiconductor nanocrystals, and any molecules bound to them, with simple fluorescence illumination-detection sources (Chan and Nie, *Science* 281, 2016-2018, 1998; Michalet et al., *Single Molecules* 2, 261-276, 2001; Howarth et al., *Proc. Natl. Acad. Sci. USA* 102, 7583-7588, 2005; Agrawal et al., *Anal. Chem.* 78, 1061-1070, 2006; Alivisatos et al., *Annual Review of Biomedical Engineering* 7, 55-76, 53 plates, 2005; Vu et al., *Nano Letters* 5, 603-607, 2005). The ability to detect nanocrystals makes the use of semiconductor nanocrystals an ideal choice to replace typical tags (such as fluorescent tags) for diverse applications.

For example, as a fluorescent label for Western blots, semiconductor nanocrystals offer much higher sensitivity (picogram quantities) and more reliable quantification (100-fold linear concentration range) then traditional chemistries based on reactions catalyzed by horse radish peroxidase (Ornberg et al., *Nature Methods* 2, 2005; Bakalova et al., *J. Am. Chem. Soc.* 127, 9328-9329, 2005. In addition, by using semiconductor nanocrystals as an in situ immunohistochemical label, target biomolecules can be localized at the single molecule level in cells (Michalet et al., *Single Molecules* 2, 261-276, 2001; Grecco et al., *Microscopy research and technique* 65, 169-179, 2004; Sundara Rajan and Vu, *Nano Letters* 6, 2049-2059, 2006).

An indispensable feature of Western immunoblotting is its capability to fractionate and determine the size of specific proteins, thus making it a favored technique for routine protein analysis of complex biomixtures. Despite widespread use, Western immunoblotting faces significant limitations in detection sensitivity, making it difficult or impossible to use in situations requiring detection of trace proteins (less than 1 ng) or scarce biosamples (less than $10^5$-$10^6$ cells). Detecting Western immunoblot signals at the level of single fluorescent tags would achieve the ultimate sensitivity limit in Western immunoblotting technology and allow even broader application of this invaluable technique. Other analytical techniques for protein detection have similar sensitivity problems.

Substantially-improved detection methods are needed to detect protein samples present at trace concentrations in complex, heterogeneous tissue and biofluid samples.

SUMMARY

This disclosure concerns an apparatus and method for detecting target biomolecules (such as polypeptides, nucleic acid molecules, and other biomolecules). The apparatus and methods allow for counting quantum dot-tagged proteins on optically transparent membranes or slides. The application of single nanoparticle detection capabilities to blotting technologies (e.g., Western blotting, membrane blotting, etc.) or protein microarrays provides a solution to a broad range of applications currently limited by insufficient detection sensitivity and/or sample availability.

In one embodiment, target biomolecules are labeled with a nanoparticle probe that includes a detectable nanoparticle, such as a fluorescent semiconductor nanocrystal (quantum dot). Target biomolecules can be labeled in situ in cells, or cell lysates or other biological solutions. The labeled biomolecules are placed on a transparent base material, such as a membrane or slide. The transparent base material is loaded onto a stage (e.g., an X-Y stage or X-Y-Z stage), which can automatically reposition the transparent base for image capture at varying locations. A microscope can be used for providing a light source to cause the nanocrystals to fluoresce and for providing the magnification needed for image capture. Once one or more images are captured, the nanoparticles can be automatically counted using post-processing software that maintains a total count across multiple images, if desired.

In another embodiment, an error rate is calculated by using a movie with multiple frames of a single location on the transparent base. The movie captures nanocrystals that are not fluorescing in one image, but fluoresce in other images, due to nanocrystal blinking. An array can be used to track a total count of nanocrystals across multiple movie frames. This total count can be compared to a single image capture at the same location to obtain an error rate associated with temporary non-fluorescing nanocrystals.

In yet another embodiment, the transparent base can be a transparent membrane or transparent slide in a variety of formats. For example, a Western blot can be used where some of the proteins are fractionated using an electric field. Another format is called a "membrane" blot, which is similar to a Western blot, but electrophoresis is not used. In another format, a protein microarray can be used wherein the nanocrystals are transferred to a slide, such as a glass slide.

The apparatus and method described herein can be useful for detecting protein or protein fragments in small populations of cells. Such detection of small numbers of cells can be useful in certain applications, such as in a solid tumor biopsy, where small numbers of cells is important.

The foregoing and other objects, features, and advantages of the invention will become more apparent from the following detailed description, which proceeds with reference to the accompanying figures.

BRIEF DESCRIPTION OF THE DRAWINGS

FIG. 3 is a schematic diagram of an exemplary procedure for the separation and detection of multiple different target biomolecules using semiconductor nanocrystals with different spectral emissions.

FIG. 4A is a digital image showing the electrophoretic migration of semiconductor nanocrystals in a 6% native polyacrylamide gel.

FIG. 4B is a digital image showing the electrophoretic migration of semiconductor nanocrystals in a composite polyacrylamide-agarose gel under native conditions (0.5× TBE running buffer).

FIG. 4C is a digital image showing the electrophoretic migration of semiconductor nanocrystals in a composite polyacrylamide-agarose gel under denaturing conditions (0.1% SDS in 0.5× TBE).

FIG. 8 is a digital image showing the ultrasensitive detection afforded by single molecule detection of low concentrations of quantum dots compared to conventional detection of UV transillumination.

FIG. 21A-C is a flowchart of a method for Single Point Quantum Dot (SPQD) Western Immunobloting along with a set of digital images showing opaque and transparent membranes and captured images of quantum dots.

FIG. 23A-C is a set of digital images illustrating that single point QD Western Immunoblotting provides a significant reduction in the amounts of required cell samples.

FIG. 25A-D is a set of digital photos showing QD blinking analysis of purified and cellular protein with populations of detected QD counts composed of single, few and multiple QDs.

DETAILED DESCRIPTION

I. Explanation of Terms

Figure 1:
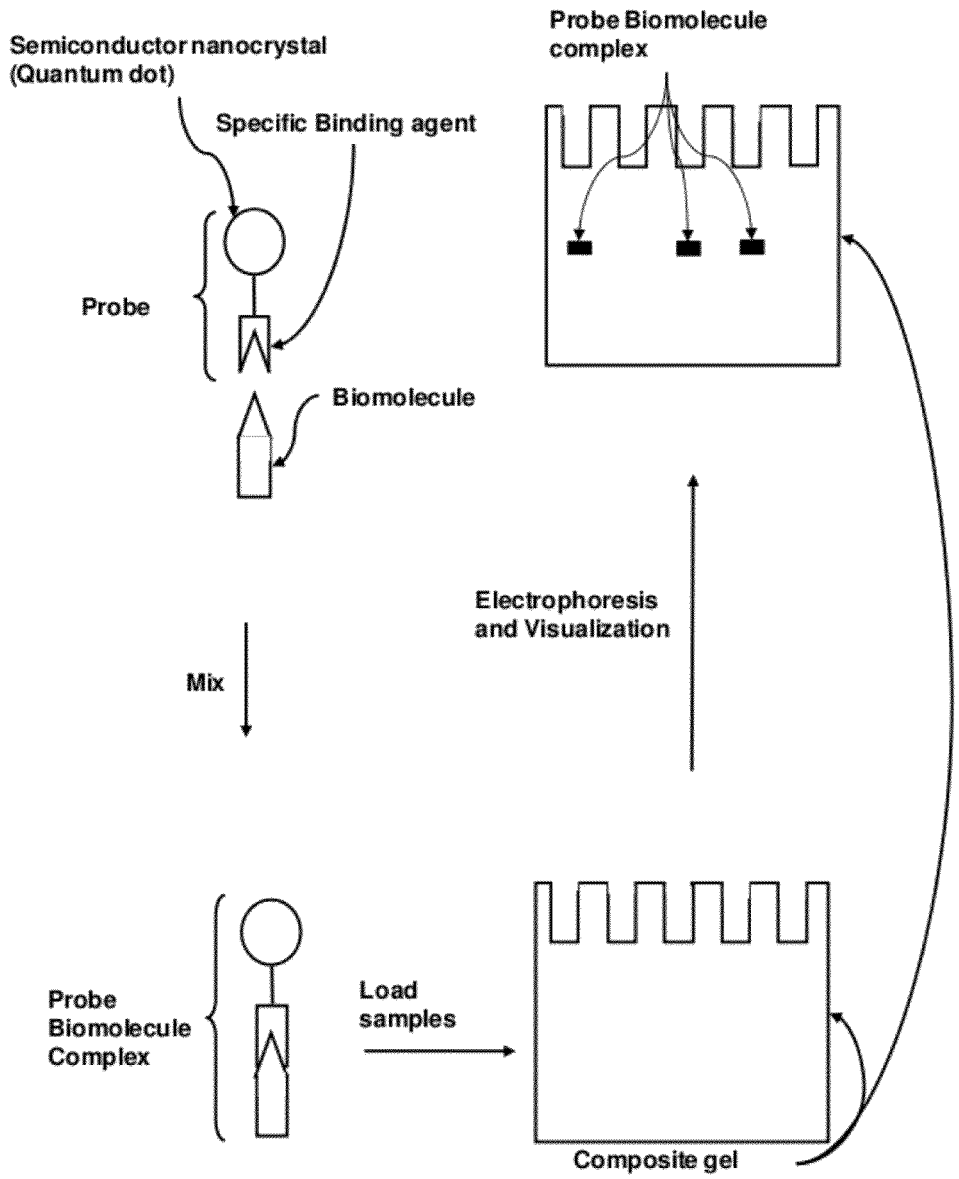
FIG. 1 is a schematic diagram of an exemplary procedure for the separation and detection of a target biomolecule:nanoparticle probe complex using composite gel electrophoresis.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of specific terms are provided:

Aptamer: Small nucleic acid or peptide molecules that bind a specific target molecule, such as a target biomolecule.

Composite gel: A gel made from two or more different component materials, for example a cross-linked polymer and a gel stabilizer.

Cross-linked polymer: A three-dimensional network formed from the chemical reaction of monomers and a cross-linker.

Detect: To determine if an agent (such as a signal or particular molecule) is present or absent. In some examples, this can further include quantification. The use of a nanoparticle probes in particular examples permits detection of a target biomolecule, for example detection of a signal from a nanoparticle probe can be used to detect the presence of a target biomolecule of interest that is labeled with the nanoparticle probe. In some examples, a single nanoparticle probe can be detected, for example, a single semiconductor nanocrystal can be detected.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths).

Emission or emission signal: The light of a particular wavelength generated from a source. In particular examples, an emission signal is emitted from a semiconductor nanocrystal after the fluorophore absorbs light at its excitation wavelengths.

Excitation or excitation signal: The light of a particular wavelength necessary and/or sufficient to excite an electron transition to a higher energy level. In particular examples, an excitation is the light of a particular wavelength necessary and/or sufficient to excite a fluorophore to a state such that the fluorophore, such as a semiconductor nanocrystal, will emit a different (such as a longer) wavelength of light then the wavelength of light from the excitation signal.

Electrophoresis: Electrophoresis, such as gel electrophoresis, is the process of separating a mixture of charged molecules based on the different mobility of these charged molecules in an applied electric field. The mobility of a molecule is generally related to the characteristics of the charged molecule, such as size, shape, and surface charge amongst others. The mobility of a molecule also is influenced by the electrophoretic medium, for example the composition of the electrophoresis gel. For example, when the electrophoretic medium is cross-linked acrylamide (polyacrylamide) increasing the percentage if acrylamide in the gel reduces the size of the resulting pores in the gel and retards the mobility of a molecule relative to a gel with a lower percentage of acrylamide (larger pore size).

Label: An agent capable of detection, for example by spectrophotometry, flow cytometry, or microscopy. For example, a label can be attached to a specific binding agent, such as an antibody or a protein, thereby permitting detection of a biomolecule bound to the specific binding agent. Specific, non-limiting examples of labels include fluorescent tags, enzymatic linkages, and radioactive isotopes and nanoparticles, such as semiconductor nanocrystals. In some embodiments, the label is a nanoparticle, such as a semiconductor nanocrystal. Methods for labeling are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Light transmissible: A material that can transmit at least some light, for example a material that light can pass through.

Linker: A compound or moiety that acts as a molecular bridge to operably link two different molecules, wherein one portion of the linker is operably linked to a first molecule, and wherein another portion of the linker is operably linked to a second molecule. The two different molecules can be linked to the linker in a step-wise manner. There are no particular size or content limitations for the linker so long as it can fulfill its purpose as a molecular bridge. Linkers are known to those skilled in the art to include, but are not limited to, chemical chains, chemical compounds, carbohydrate chains, peptides, haptens, and the like. The linkers can include, but are not limited to, homobifunctional linkers and heterobifunctional linkers. Heterobifunctional linkers, well known to those skilled in the art, contain one end having a first reactive functionality to specifically link a first molecule, and an opposite end having a second reactive functionality to specifically link to a second molecule. Depending on such factors as the molecules to be linked, and the conditions in which the method of detection is performed, the linker can vary in length and composition for optimizing such properties as flexibility, stability, and resistance to certain chemical and/or temperature parameters. For example, short linkers of sufficient flexibility include, but are not limited to, linkers having from 2 to 10 carbon atoms (see for example U.S. Pat. No. 5,817,795). In particular examples, a linker is the combination of streptavidin or avidin and biotin.

Film: A composition capable of adhering to a membrane, such as a PDVF membrane, and substantially inhibiting the atmosphere from contacting the membrane. The film can be applied to one side, both sides, or even a portion of the membrane.

Nanoparticles: Particles having maximum dimensions of about 1000 nanometers (nm) in any direction, meaning that the particle does not have any dimension that exceeds 1000 nm. In some examples, a nanoparticle has maximum dimensions of about 100 nm or less in any direction. An example of a nanoparticle is a quantum dot, but other examples include iron oxide or gold nanoparticles. Examples of methods of making gold nanoparticles are disclosed in U.S. Patent Publication 2005/0120174. Nanoparticles used as the nanoparticle probes of the present disclosure can be of any shape (such a spherical, tubular, pyramidal, conical or cubical), but particularly suitable nanoparticles are spherical. The spherical surface provides a substantially smooth and predictable high surface to volume ratio that can be optimized for controlled attachment of specific binding agents such as antibodies, with the bound agents extending substantially radially outwardly from the surface of the sphere.

Nucleic acid molecule (or sequence): A deoxyribonucleotide or ribonucleotide polymer including without limitation, cDNA, mRNA, genomic DNA, and synthetic (such as chemically synthesized) DNA or RNA. The nucleic acid molecule can be double stranded (ds) or single stranded (ss). Where single stranded, the nucleic acid molecule can be the sense strand or the antisense strand. Nucleic acid molecules can include natural nucleotides (such as A, T/U, C, and G), and can also include analogs of natural nucleotides. In one embodiment, a nucleic acid molecule is an aptamer.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. (herein incorporated by reference).

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Polymerization: The reaction of monomer molecules together in a chemical reaction to form linear chains or a three-dimensional network of polymer chains. In one embodiment, the polymer polyacrylamide is formed from the polymerization of acrylamide in the presence of a crosslinker, which in some embodiments is N',N-methylenebisacrylamide (BIS). Upon the introduction of catalyst, the polymerization of acrylamide and BIS proceeds via a free-radical mechanism. The most common system of catalytic initiation involves the production of free oxygen radicals by ammonium persulfate (APS) in the presence of the tertiary aliphatic amine N,N,N',N'-tetramethylethylenediamine (TEMED) although other free radical generators can be employed.

Polysaccharide gel stabilizer: A polysaccharide that stabilizes the three-dimensional structure of a gel.

Peptide/Protein/Polypeptide: All of these terms refer to a polymer of amino acids and/or amino acid analogs that are joined by peptide bonds or peptide bond mimetics. In one embodiment, a peptide is an aptamer.

Probe: Any molecule that specifically binds to a protein or nucleic acid sequence that is being targeted, and which can be identified (detected) so that the targets can then be detected. In particular examples, the probe is a nanoparticle probe that is labeled with a specific binding agent for binding the nanoparticle to a target biomolecule, such as a particular protein, peptide, small molecule, or nucleic acid molecule. In certain embodiments, the probe can be identified by the color, or composition of the nanoparticle, or by the wavelength of light, such as a color of light, emitted by the nanoparticle (as in a quantum dot). In certain embodiments, the probe includes a nanoparticle conjugated to an antibody or other specific-binding molecule that binds to a target protein.

Quantitating: Determining or measuring a quantity (such as a relative quantity) of a molecule, such as the quantity of a target biomolecule.

Sample: Any quantity of a substance that includes targets (such as target biomolecules) that can be used in a method disclosed herein. The sample can be a biological sample or can be extracted from a biological sample derived from humans, animals, plants, fungi, yeast, bacteria, tissue cultures, viral cultures, or combinations thereof. In particular examples of the disclosed compositions and methods, the biological sample is a cellular suspension.

Semiconductor nanocrystals (quantum dots): Semiconductor nanocrystals have evolved over the last few years to provide a new type of fluorescent label. Semiconductor crystalline nanospheres are also known as quantum dots, which are engineered, inorganic, semiconductor nanocrystals that fluoresce stably and possess a uniform generally spherical surface area that can be chemically modified to attach biomolecules to them, such as a specific binding agent. Generally, semiconductor nanocrystals can be prepared with relative monodispersity (for example, with the diameter of the core varying approximately less than 10% between semiconductor nanocrystals in the preparation), as has been described previously (Bawendi et al., *J. Am. Chem. Soc.* 115:8706, 1993). Semiconductor nanocrystals are known in the art have, for example, a core selected from the group consisting of CdSe, CdS, and CdTe (collectively referred to as "CdX"). These semiconductor nanocrystals have been used in place of organic fluorescent dyes as labels in immunoassays (as in U.S. Pat. No. 6,306,610) and as molecular beacons in nucleic acid assays (as in U.S. Pat. No. 6,500,622).

Specific binding agent: A specific binding agent is an agent that binds substantially only to a defined target. Thus a protein-specific binding molecule binds substantially only the specified protein. Examples include antibodies that bind to specific antigens, and nucleic acid molecules that hybridize to substantially identical complementary nucleic acid sequences under hybridization conditions of varying stringency (such as highly stringent conditions). Another example is a protein that specifically binds to a receptor (such as neurotrophin that specifically binds to a TrkA receptor expressed on the surface of certain neurons). Other examples of specific binding agents include aptamers.

Target biomolecule: A target biomolecule for the nanoparticle probes is a molecule of interest about which information is desired. A target biomolecule can be any molecule that is or once was part of a living organism. In several non-limiting examples, a target biomolecule is a polypeptide, a nucleic acid, a ligand, or a small molecule. In one example, the information desired is location of the biomolecule on or within a cell, such as a cell in a biological sample. In another example, the information desired is the presence or absence of the biomolecule, for example in a sample, such as a biological sample. In another example, the information desired is the presence, absence, and/or location of the target biomolecule in a gel, such as a composite gel. In another example, the information desired is the presence, absence, and/or location of the target biomolecule in on a membrane, such as a polyvinylidene fluoride (PVDF) membrane.

Translucent: Having the property of transmitting at least some light. A translucent material can be substantially transparent, such that light passes through the material without substantial scattering and/or absorption. In one example, a translucent material, such as a membrane, is transparent to light in the UV visible spectrum, for example wavelengths of light between about 1 nanometers and about 750 nanometers.

Visible: Capable of detection, by the eye or other detection device.

II. Detailed Description of Several Embodiments

Disclosed herein are novel methods of using detectable nanoparticle probes, such as fluorescent semiconductor nanocrystals (quantum dots), that improve both the capabilities of gel electrophoresis and immunohistochemistry. These methods are based on the discovery that a composite gel matrix can be used to separate biomolecules labeled with detectable nanoparticle probes, such as fluorescent semiconductor nanocrystals. A particular advantage of the disclosed method is that fluorescent semiconductor nanocrystals can be used to visualize target biomolecules (such as proteins) in cells and the same fluorescent semiconductor nanocrystal biomolecule complexes can be purified and directly visualized in one step using a composite gel (such as a polyacrylamide-agarose gel).

In conventional protein electrophoresis the constituents of a biological sample, such as a cell lysate, are separated by electrophoresis in a polyacrylamide matrix (either under native or non native conditions, for example in the presence of a detergent, such as sodium dodecyl sulfate (SDS), and/or a reducing agent, such as a beta-mercaptoethanol (BME)). A limitation of conventional polyacrylamide gels is that nanoparticles, such as fluorescent semiconductor nanocrystals, are not mobile in the gel (see for example FIG. 4A). The lack of mobility in conventional polyacrylamide gels inhibits the separation of nanoparticle labeled biomolecules.

Nanoparticles, such as fluorescent semiconductor nanocrystals, have been shown to be mobile in agarose gels. However, agarose gels have large pores and do not resolve individual protein species labeled with nanoparticles, such as proteins labeled with fluorescent semiconductor nanocrystals. In addition, agarose gels also display a high degree of opacity which may interfere with the detection of signals produced by fluorescent semiconductor nanocrystals. Finally, agarose gels are not suitable for Western blotting because proteins cannot easily be transferred by electroblotting from the agarose gel to a membrane suitable for detection (for example, to investigate protein-protein interactions).

The methods disclosed herein overcome the deficiencies present in both agarose and polyacrylamide gels by using composite gels formed from a mixture of a cross-linked polymer (such as acrylamide) and a gel stabilizer (such as agarose) for the separation and identification of biomolecules in complex with nanoparticles. Unlike polyacrylamide and agarose gels, the composite gels are able to separate nanoparticle-biomolecule complexes by electrophoresis. In addition, the proteins that are separated can be transferred to membranes, such as PVDF membranes, for identification and probing of protein-protein interactions by Western blotting. In some embodiments, a film is applied to a membrane to prevent exposure to the atmosphere and/or photo-bleaching.

The methods disclosed herein provide, for the first time, the ability to directly correlate Western blot analysis with fluorescence localization in cells, because the same nanoparticle-biomolecule complexes can be visualized in both methods. An added benefit of direct semiconductor nanocrystal in-gel electrophoresis is that it is more rapid than conventional polyacrylamide gel electrophoresis (PAGE) in determining protein-protein interactions, because it eliminates extensive and time-consuming immunoprecipitation steps that are typically involved in determining protein-protein interactions. Furthermore, the methods disclosed herein are more sensitive than conventional indirect fluorescence detection steps, because they take advantage of the superior fluorescence properties of fluorescent semiconductor nanocrystals. In addition, the superior fluorescent properties of the semiconductor nanocrystals also allows for the quantification and visualization of the semiconductor nanocrystals, and proteins bound by probes that include such semiconductor nanocrystals, at single nanocrystal resolution.

The ability to analyze protein electroblots at the single semiconductor nanocrystal level can significantly enhance the detection of proteins and their protein-protein association through improvement in signal, signal to noise ratio, noise reduction, and quantitative capability. After separation and hybridization, specific binding can be distinguished from random binding on single molecule level on PVDF membrane.

A. Methods for the Detection of Target Biomolecules

Disclosed herein are methods for detecting a target biomolecule of interest in a sample. An exemplary procedure is diagrammed in FIG. 1. The method involves contacting a sample, such as a biological sample, that contains or is suspected of containing a target biomolecule of interest with a nanoparticle probe that includes a detectable nanoparticle, such as a semiconductor nanocrystal (exemplary nanoparticles for use with the disclosed methods are given below in section D). A biomolecule of interest can be any biomolecule about which information, such as location, is desired. Examples of such biomolecules include without limitation polypeptides, nucleic acids, ligands, or small molecules. The formation of a complex between the target biomolecule of interest and the nanoparticle probe effectively labels the target biomolecule of interest in the sample. Once the sample has been contacted with the nanoparticle probe, the constituents of the sample are prepared for separation by electrophoresis. Typically the sample is mixed with loading buffer, and then the sample is loaded onto a composite gel that includes a cross-linked polymer and a gel stabilizer and is capable of separating the labeled target biomolecule of interest from other biomolecules in the sample (exemplary composite gels for use in the disclosed methods, such as polyacrylamide-agarose gels, are given below in section C). The sample, which includes the labeled target biomolecule of interest, is electrophoresed in the composite gel to separate the labeled target biomolecule of interest from other biomolecules in the sample. Methods of electrophoretic separation are well known in the art and can be found, for example, in Sambrook et al., *Molecular Cloning: A Laboratory Manual*, 3$^{rd}$ ed. Cold Spring Harbor Press, 2000, and U.S. Pat. Nos. 4,889,606 and 5,449,446). Standard electrophoresis buffers can quench semiconductor nanocrystal fluorescence. Accordingly, a buffer that does not cause fluorescence quenching can be selected, such as 0.5× TBE (Tris-Boric acid-EDTA) electrophoresis running buffer. The electrophoresis is run in buffer for a period time and at a voltage sufficient to achieve desired separation of nanoparticle labeled biomolecules, such as for 1-2 hours at 100V. The nanoparticle is detected, such that detection of the nanoparticle detects the target biomolecule of interest in the electrophoresed sample. Exemplary methods for the detection of nanoparticles, such as semiconductor nanocrystals, are given below in section E, however any method can be used that allows for the detection of nanoparticles.

Molecules, such as nanoparticle probes, target biomolecules, and labeled biomolecules (such as a biomolecule labeled with a nanoparticle probe) have physical characteristics, for example size, mass, charge, shape and the like. The physical characteristics of a nanoparticle probe and/or a target biomolecule would be expected to affect the electrophoretic mobility of a labeled target biomolecule in a gel, for example when the target biomolecule is labeled with a nanoparticle probe, such as a nanoparticle probe that includes a detectable nanoparticle. Using the methods disclosed herein, target biomolecules that are labeled with a nanoparticle probe, which includes a detectable nanoparticle, are able to be separated by the physical characteristics of the nanoparticle probe (for example, the size, charge, weight, or other physical characteristic of the nanoparticle probe), the physical characteristics of the target biomolecule (for example, the size, charge, weight, or other physical characteristic of the target biomolecule), or a combination thereof.

In some situations, it may be advantageous to separate the labeled target biomolecule by the physical characteristics (such as size) of the nanoparticle probe. In one example, nanoparticle probes that are different sizes can be used to label different target biomolecules of interest that have the same or similar sizes, in this way the nanoparticle probe can be used to effectively separate biomolecules that would otherwise co-localize during gel electrophoresis, such as during traditional polyacrylamide or agarose gel electrophoresis. When the nanoparticle probe includes a semiconductor nanocrystal, different sizes of semiconductor nanocrystals with different emission spectra can be used (for example, if the size of the nanocrystal is varied and the composition is maintained), effectively separating the biomolecules of interest by the size and the spectral emission of the nanoparticle probe. Alternatively, semiconductor nanocrystals with the same emission spectra can be used.

In some situations it may be advantageous to separate the labeled target biomolecule by the physical characteristic of the target biomolecule. By way of example, nanoparticle probes can be used that are of the same size to label a target biomolecule of interest with multiple isoforms that have dissimilar sizes (for example, a protein with different transcriptional start sites), in this way the nanoparticle probe can be used to effectively discriminate between the multiple isoforms of the biomolecule during gel electrophoresis using the composite gels described herein. When the nanoparticle probe includes a semiconductor nanocrystal, semiconductor nanocrystals with different emission spectra can be used (for example, if the size of the nanocrystal is maintained and the composition is varied). Alternatively, semiconductor nanocrystals with the same emission spectra can be used.

In some embodiments, the target biomolecule is labeled with a nanoparticle probe having a defined physical characteristic that separates the labeled target biomolecule during electrophoresis. In some embodiments, the physical characteristic of the nanoparticle probe is the size of the nanoparticle probe and the labeled target biomolecule is separated by the size of the nanoparticle probe. In some embodiments, the physical characteristic of the nanoparticle probe is the mass of the nanoparticle probe and the labeled target biomolecule is separated by the mass of the nanoparticle probe. In some embodiments, the physical characteristic of the nanoparticle probe is the charge of the nanoparticle probe and the labeled target biomolecule is separated by the charge of the nanoparticle probe. In some embodiments, the labeled target biomolecule is separated by the physical characteristics of the target biomolecule. In some embodiments, the labeled target biomolecule is separated by the combination of the physical characteristics of the nanoparticle probe and target biomolecule.

In some embodiments, the nanoparticle probe includes a specific binding agent that specifically binds the target biomolecule of interest. In some embodiments, the specific binding agent is an antibody, a ligand, an aptamer, or a peptide. The specific binding agent can be conjugated directly to the nanoparticle. Alternatively, the specific binding agent can be operably linked to the nanoparticle with a linker. Methods for the conjugation of nanoparticles and specific binding agents, for example via a linker, are given below. In some embodiments, the linker is streptavidin, avidin, biotin, or a combination thereof.

The present methods are applicable for any sample for which information about a biomolecule of interest is desired, for example to detect the presence of and/or location of the biomolecule of interest or the interaction partner(s) of the biomolecule of interest. In the case of cellular samples, such as tissue samples (for example cultured cells), the sample can be contacted with a nanoparticle probe and then lysed or homogenized to solubilize or suspend the constituent biomolecules, such as the target biomolecule. Optionally, the sample can be further processed, for example to remove particulate matter or debris, or partially purified to isolate a class of molecules (such as proteins) of interest. In the case of biological fluid samples, the fluid can be partially purified or concentrated if desired.

In some embodiments, a detectable nanoparticle is a semiconductor nanocrystal (for example, a semiconductor nanocrystal with maximum dimensions between about 5 nm and 1000 nm) that emits a detectable electromagnetic signal, such as a characteristic emission spectrum, for example light. The detectable electromagnetic signal emitted by the semiconductor nanocrystal can be used to identify the target biomolecule of interest, for example to identify the position (location) of the target biomolecule of interest on or within a cell, within a gel (such as a composite gel), or on or within a membrane (for example, a transfer membrane, such as a membrane that can be used for a Western blot). In one embodiment, the characteristic emission spectrum of a semiconductor nanocrystal identifies the presence or position (location) of the target biomolecule on or within a cell. In another embodiment, the characteristic emission spectrum of the semiconductor nanocrystal identifies the presence or position (location) of the target biomolecule within a gel, such as a composite gel. In another embodiment, the characteristic emission spectrum semiconductor nanocrystal identifies the presence or position (location) of the target biomolecule on or within a membrane. In some situations it may be advantageous to separate a cell or population of cells from other cells prior to electrophoresis, for example when the sample is a plurality of cells. Thus, in some embodiments, the characteristic emission spectrum of the semiconductor nanocrystal is used to separate a cell or population of cells of interest, for example using fluorescent activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620).

If desired, the separated biomolecules of interest, such as proteins, can be transferred to a membrane (such as PVDF-membranes) for further characterization. Typically, a transfer buffer is selected that does not appreciably quench the fluorescence of semiconductor nanocrystals, such that the fluorescence emission spectrum of the semiconductor nanocrystal is maintained. While not wanting to be bound by theory, it is believed that some metal ions interfere with the fluorescence of semiconductor nanocrystals. Thus, it may be advantageous to include an agent that removes metals from the buffer, such as EDTA and the like. In one example 0.5× tris-boric acid-EDTA (TBE)-20% methyl alcohol may chosen as the transfer buffer instead of the more common Tris-Glycine-20% methyl alcohol. In some examples, the transfer buffer is removed from the membrane, for example by washing, such that the buffer does not interfere with the fluorescence of the semiconductor nanocrystals on the membrane.

In some embodiments, the target biomolecule of interest is transferred to a membrane, such that the target biomolecule can be further identified, for example by contacting the membrane with a detectable probe capable of specifically binding to the target biomolecule of interest and detecting the detectable probe. Detecting the detectable probe identifies the target biomolecule of interest on the membrane. In some embodiments, the detectable probe includes a specific binding agent that specifically binds the target biomolecule of interest, such as an antibody, a ligand, an aptamer, or a peptide. Typically, the detectable probe includes a label, such as an electron-dense compound, an enzyme, a fluorochrome, a hapten, a radioisotope, or a nanoparticle (for example, a semiconductor nanocrystal). In specific embodiments, the detectable probe includes a semiconductor nanocrystal. In the some examples, the detectable probe includes a semiconductor nanocrystal with an emission spectrum distinct from the emission spectrum of the semiconductor nanocrystal included in the nanoparticle probe used to label the target biomolecule. Thus, the different emission spectra can be used to detect and identify the target biomolecule.

Figure 2:
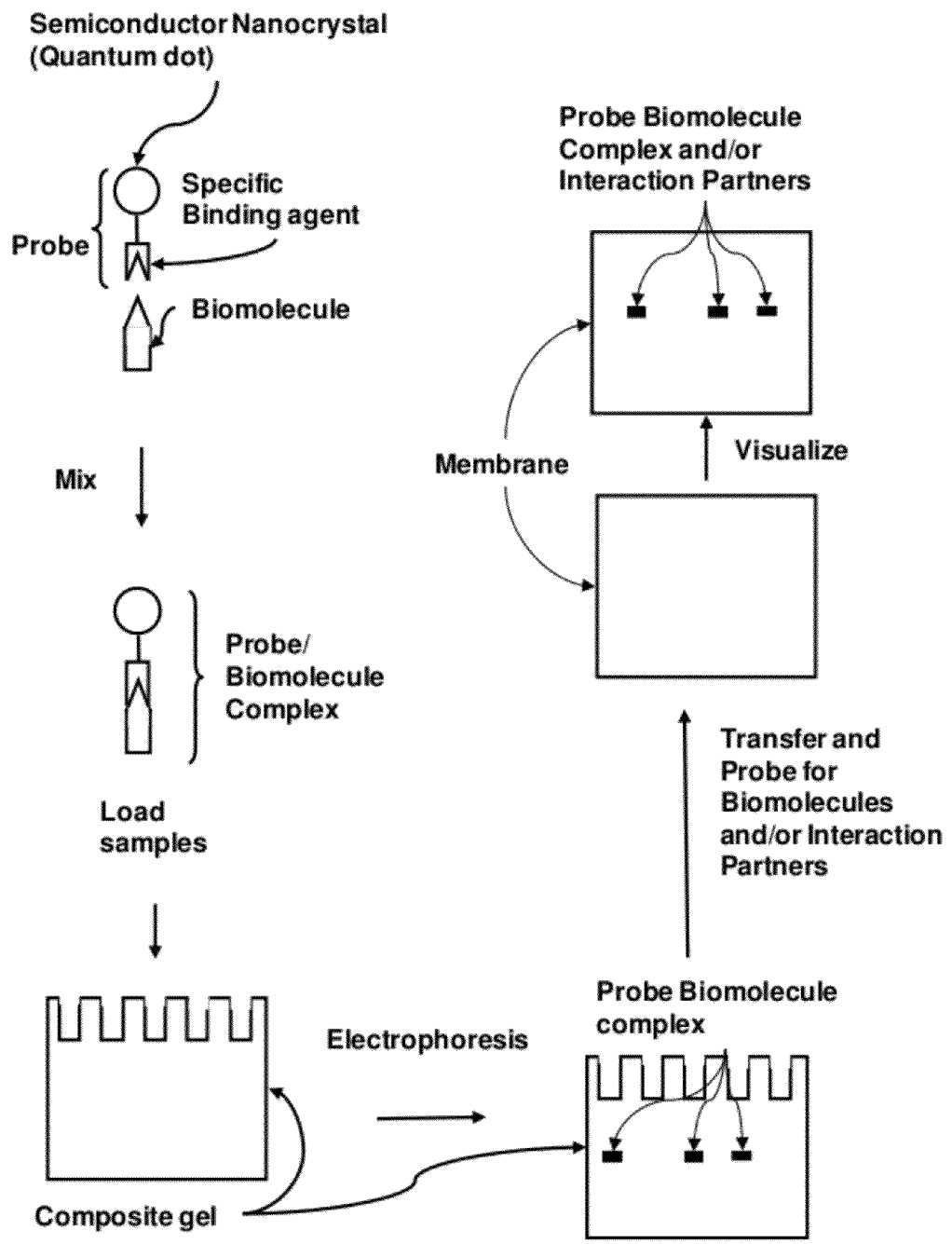
FIG. 2 is a schematic diagram of an exemplary procedure for the separation, detection, and identification of a target biomolecule:nanoparticle probe complex using composite gel electrophoresis and transfer to membrane for Western blot analysis.

The disclosed methods are particularly suitable for the detection of biomolecules that interact with a target biomolecule. By way of example, a labeled target biomolecule can be separated by gel electrophoresis using a composite gel (such as the gels described herein). The separated biomolecules (such as proteins) present in or on the gel (including the target biomolecule of interest and biomolecules interacting with the biomolecule of interest) can be transferred to a membrane and probed for the presence of biomolecules suspected of interacting with the target biomolecule, for example by contacting the membrane with detectable probe capable of specifically binding a biomolecule that is suspected of interacting with the target biomolecule. The detectable probe is detected and it is determined if the detectable probe co-localizes with the target biomolecule of interest. Co-localization of the detectable probe with the target biomolecule of interest indicates that that the biomolecule interacts with the target biomolecule of interest. In some embodiments, the detectable probe includes a specific binding agent that specifically binds the biomolecule suspected of interacting with the biomolecule of interest, such as an antibody, a ligand, an aptamer, or a peptide. Typically, the detectable probe includes a label, such as an electron-dense compound, an enzyme, a fluorochrome, a hapten, a radioisotope, or a nanoparticle (for example, a semiconductor nanocrystal). In specific embodiments, the detectable probe includes semiconductor nanocrystal. In the some examples, the detectable probe includes a semiconductor nanocrystal with an emission spectrum distinct from the emission spectrum of the semiconductor nanocrystal included in the nanoparticle probe. Thus, the different emission spectra can be used to detect and identify the target biomolecule of interest and the biomolecule suspected of interacting with the target biomolecule of interest. An exemplary procedure for the detection and identification of target biomolecules of interest and their interaction partners is diagramed as FIG. 2.

The disclosed methods are equally applicable to detection of multiple biomolecules of interest in a sample. FIG. 3, for example, illustrates different biomolecules of interest (such as protein biomolecules) that have been electrophoretically separated and labeled with distinguishable semiconductor nanocrystals. The method involves contacting a sample, such as a biological sample, that contains or is suspected of containing a plurality of (such as more than one) different biomolecules of interest with a different nanoparticle probe specific for each different biomolecule of interest, wherein the different nanoparticle probes include different detectable nanoparticles. The formation of a complex between the target biomolecules of interest and the different nanoparticle probes specific for each different biomolecule of interest effectively labels the target biomolecules of interest in the sample. The sample, which includes the labeled biomolecules of interest, is electrophoresed in a composite gel to separate the labeled target biomolecules of interest from other biomolecules in the sample. The nanoparticles are detected, such that detection of the nanoparticle detects the different target biomolecules of interest in the electrophoresed sample, for example relative to a different molecular weight. In some embodiments, each different biomolecule of interest is labeling with a nanoparticle probe having a defined physical characteristic different from the other nanoparticle probes and the different biomolecules of interest are separated by the physical characteristic of the nanoparticle probe. In some embodiments, the physical characteristic of the nanoparticle probes is the size of the nanoparticle probes and the different biomolecules of interest are separated by the size of the nanoparticle probes. In some embodiments, the physical characteristic of the nanoparticle probes is the mass of the nanoparticle probes and the different biomolecules of interest are separated by the mass of the nanoparticle probes. In some embodiments, the physical characteristic of the nanoparticle probes is the charge of the nanoparticle probes and the different biomolecules of interest are separated by the charge of the nanoparticle probes. In some embodiments, each of the different detectable nanoparticles has the same physical characteristic and the different labeled biomolecules of interest are separated by the size of the different biomolecules of interest. In some embodiments, each of the different detectable nanoparticle probes includes a specific binding agent that specifically binds each different biomolecule of interest. In some embodiments, each of the different detectable nanoparticles includes a different semiconductor nanocrystal that emits a characteristic detectable electromagnetic spectrum distinct from the other semiconductor nanocrystals. In some embodiments, the characteristic emission spectra from the different semiconductor nanocrystals are light and the different biomolecules of interest are detected by detecting different wavelengths of light, such as colors of light.

B. Films

Disclosed herein are methods for sealing a membrane containing semiconductor nanocrystals. In some embodiments, a film is applied, for example as a sealant, to a membrane, such as a PVDF membrane, to substantially seal the membrane, for example to avoid or prevent contact with the atmosphere or oxygen in the atmosphere, and/or to maintain or increase the transparency of the membrane to light, such as light in the ultraviolet(UV)-visible spectrum, such that the membrane is translucent, for example, substantially optically transparent to light in the UV-visible spectrum.

Under some conditions, the ability to visualize semiconductor nanocrystals transferred to membranes can be limited, for example rapid quenching can photo-bleach single semiconductor nanocrystals, sometimes in less then about 60 seconds of UV-illumination. In addition, membrane auto-fluorescence can mask the signal of single semiconductor nanocrystals. While photo-bleaching and auto-fluorescence typically does not affect the ability to visualize and/or quantitate large numbers of semiconductor nanocrystals present on a membrane (for example as viewed as a band on a membrane under normal magnification), these phenomena can reduce the ability to visualize single semiconductor nanocrystals, for example under magnification, such as high magnification. While not wanting to be bound by theory, photo-bleaching of single semiconductor nanocrystals is presumed to occur through a photo-oxidative mechanism, for example in water-based buffers such as PBS, TBS, and culture media such as DMEM.

The observation of semiconductor nanocrystals, such as quantum dots, at the single particle level on membranes is facilitated by increasing the transparency of the membranes, for example by rendering the membranes at least translucent, such as optically transparent to light in the UV-visible spectrum, producing a low background autofluorescence, and substantially sealing the membranes from interaction with the atmosphere to reduce photo-bleaching of semiconductor nanocrystal fluorescence, for example for a duration necessary for imaging single semiconductor nanocrystals present on the membrane (for example a duration greater than about 5 minutes, such as greater than about 10 minutes, greater than about 15 minutes, greater than about 20 minutes, greater than about 25 minutes, or even greater than about 30 minutes).

As disclosed herein, the physiochemical interaction of a translucent film, for example a film that is substantially transparent to light in the UV-visible spectrum, such as a film of a silica containing polymer or monomer, with the membrane, such as a PVDF membrane, creates a translucent film/membrane hybrid, which increases the membrane's optically transparency (for example optically transparent to light in the UV-visible range), keeps this glassy-like transparent stable, and creates a protective seal on the membrane. This interaction is aided if material used to produce the film and the membrane are of similar hydrophobicity (for example through interaction of a hydrophobic agent, such as a silica-based monomer or polymer, with hydrophobic PVDF membrane). Moreover, sealing the membranes mitigates UV-induced quenching such that membranes are stable to UV-illumination induced photo-bleaching for periods greater than 5 minutes, such as greater than 10 minutes, greater than 15 minutes, greater than 20 minutes, greater than 25 minutes, or even greater than 30 minutes.

As disclosed herein, a semi-interpenetrating network can be formed from a membrane, such as a PVDF membrane, and a light transmissible film, such as a translucent film of silica-based polymers and/or monomers, such as silica-based polymers and monomers that are substantially optically transparent to light in the UV-visible spectrum. These silica-based networks produce a stable silica-PVDF membrane network which is at least translucent, such as transparent, and emits very little autofluorescence. This discovery allows visualization of single semiconductor nanocrystals, such as quantum dots, on and/or inside a membrane, for example a membrane used in a typical blot application, such as Western, Northern, Southern or any other protein/nucleic acid blot application. The film effectively seals semiconductor nanocrystals from the atmospheric effects of oxidation thus prolonging semiconductor nanocrystals fluorescence stability. This discovery greatly enhances the ability to stably image single semiconductor nanocrystals, for example for periods exceeding 30 minutes. The ability to maintain fluorescence of semiconductor nanocrystals is important for applications in which the blot needs to be imaged for long periods, for example scanning a membrane for the presence of single semiconductor nanocrystals on a membrane that is several centimeters in length in single steps on the micrometer scale. This ability to maintain the fluorescence of semiconductor nanocrystals also greatly improves the ability to image multiple different color semiconductor nanaocrystals sequentially on a single membrane. For example, to show co-localization of two or more semiconductor nanocrystals of two or more colors it may necessary to scan the same section of a membrane multiple times. The ability to maintain the fluorescence of the semiconductor nanocrystals greatly enhances this ability.

While not bound by theory, it is believed that upon introduction of a silica-based polymer or monomer to the surface of a membrane that the silica-based polymer or monomer penetrates the existing polymer network of the membrane, such as a PDVF membrane, on the molecular scale. The penetration of the silica-based polymer or monomer is believed to be a physical interaction facilitated by intermolecular forces, such as van der Waals forces, not intermolecular cross-linking. Thus, the silica-based polymer or monomer can be separated from the polymer network of the membrane. As a result, upon removal of the silica-based polymer or monomer through washing, the membrane can be converted back to its pre-sealed state. This reversibility is particularly useful for applications where imaging can be performed, the membrane blot further hybridized, and re-imaged.

Typically a film is chosen, such that when the film is applied to the membrane, the membrane is sealed and at least translucent, for example substantially transparent to light in the UV-visible range, and the fluorescence of the semiconductor nanocrystals is not quenched by addition of the film. Thus, the choice of film can be influenced by the spectral properties of the film. For example, in some embodiments, a film is chosen that is at least translucent, such as clear, for example substantially transparent to light in the UV-visible range, such that the film does not interfere with light passing through the membrane or emanating from the semiconductor nanocrystals present on the membrane. For example, a film is chosen that does not exclude the wavelength of light used to excite the semiconductor nanocrystals or the wavelength of light emitted by the semiconductor nanocrystals.

As disclosed herein, photo-bleaching of semiconductor nanocrystals can be reduced by air drying membranes, and substantially sealing them, and rendering them at least translucent, such that the membranes are light transmissible, for example using a non-florescent polymer or monomer, such as a silica-based polymer of which silica (silicon dioxide) is the main backbone constituent. By forming organic side-chains of the Si—O—Si—O inorganic backbone, silica-agents are formed which now can penetrate the hydrophobic PVDF polymer network.

Silica-based agent that are of use as films in the disclosed methods include without limitation siloxanes, silcones, silanes, specialty silanes, silane coupling agents, polysilanes silathianes, stannoxanes, silazanes, polymethylsilsesquioxanes, polyvinylsilsequioxanes, polyphosphazines, polysilazanes, polysiloxanes, polysilsesquioxanes, polyborosilanes, polycarbosilazanes, variants, derivatives and combinations thereof.

Siloxanes are chemical compounds composed of an inorganic silicon-oxygen backbone ( . . . —Si—O—Si—O—Si—O— . . . ) of units of the form $[R1R2SiO]_n$, where R1 and R2 are independently hydrogen or a hydrocarbon group, examples of siloxanes include polysiloxanes, polyvinylsiloxanes, and polymethylsiloxanes among others. Silcones, also referred to as polymerized siloxanes, are mixed inorganic-organic polymers with the chemical formula $[R1R2SiO]_n$, where R=is a organic group, such as methyl, ethyl, and phenyl etc. These materials are composed of an inorganic silicon-oxygen backbone ( . . . —Si—O—Si—O—Si—O— . . . ). The organic side-chains present on Si atoms confer hydrophobic properties. Silanes are silicon analogues of alkane hydrocarbons. Silanes are composed of a chain of silicon atoms covalently bound to hydrogen atoms. The general formula of a silane is $[SiH_{2n+2}]_n$. Specialty silanes, such as chlorosilanes, ogranfunctional silanes, alhylsilanes, polyborosilanes, methylpolycarbosilane, vinylpolycarbosilanes, methylvinylpolycarbosilane, polytitanocarbosilane, allyl hydridopolycarbosilanes, hydridopolycarbosilane, and polycarbosilanes, contain reactive groups which react with other silanols to for a siloxane bond. Silane coupling agents are silcon-based chemicals that contain two types of reactivity inorganic and organic—in the same molecule. A typical structure of silane coupling agents is: $(RO)_3SiCH_2CH_2$—X where RO is a hydrolyzable group, such as methoxy, ethoxy, or acetoxy, and X is an organofunctional group, such as amino, methscryloxy, epoxy. Polysilanes have a continuous backbone of silicon atoms. Silathianes are compounds having the structure $H_3Si[SSiH_2]_nSSiH_3$ and branched-chain analogues. Silathianes are analogous in structure to siloxane with —S— replacing —O—. Stannoxanes are compounds having the structure $H_3Sn[OSnH_2]_nOSnH_3$, and are Ttin (Sn) analogues of siloxanes. Silazanes are saturated silicon-nitrogen hybrids, having straight or branched chains. They are analogous in structure to siloxanes with —NH— replacing —O—, for example trisilazane has the general chemical formula $H_3SiNHSiH_2NHSiH_3$.

Specific examples of polymers and monomers that can be used to seal membranes, such as PVDF membranes, are polysiloxanes, such dimethylvinyl terminated polydimethylsiloxane, CAS No. 68083-19-2, dimethyl, methylhydrogen siloxane, CAS No. 68037-59-2, dimethyl siloxane, and tetramethyl-tetravinyl-cyclotetrasiloxane, silanes, such as tetra (trimethylsiloxy) silane CAS No. 3555-47-3, dimethylvinylated and trimethylated silica CAS No. 68988-89-6, and combinations thereof, such as encapsulants sold by the Dow Corning company under the trade name SYLGARD®, (such as SYLGARD®184, and SYLGARD®182) amongst others.

Figure 14:
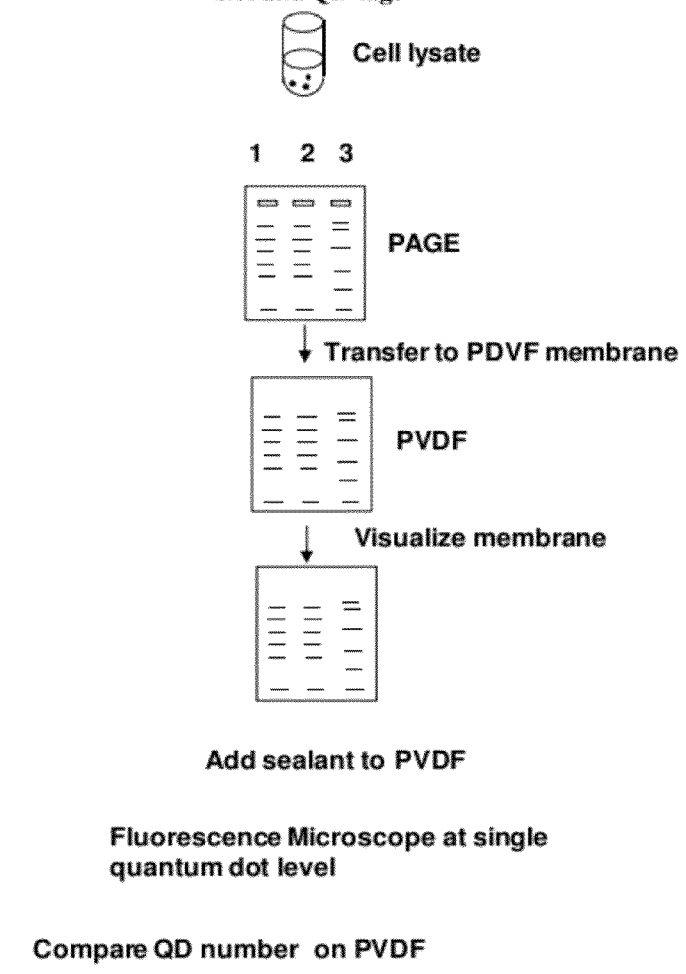
FIG. 14 is a schematic showing an exemplary procedure for the visualization of single semiconductor nanocrystals using sealed membranes during conventional PAGE transfer to a PDVF membrane and hybridization with semiconductor nanocrystals labeled antibodies.

The disclosed methods of rendering the PVDF membranes at least translucent, such as substantially transparent to light in the UV-visible spectrum, and inhibiting photo-bleaching of semiconductor nanocrystals can be used to detect single semiconductor nanocrystals in traditional Western, Northern, Southern or any other protein/nucleic acid blot application. An exemplary procedure for inhibiting photo-bleaching of semiconductor nanocrystals when used in conventional Western blotting is shown in FIG. 14. In this method target biomolecules, such as proteins, are separated by standard PAGE techniques known to those of skill in the art. The separated target biomolecules are then transferred to a membrane, such as a PVDF membrane. Typically this is done by electroblotting. The transferred target biomolecule can be further identified, for example by contacting the membrane with a detectable probe, such as a probe that includes a semiconductor nanocrystal, capable of specifically binding to the target biomolecule of interest. The membrane is sealed with a film and the presence of the detectable probe on the membrane determined. This identifies the target biomolecule of interest on the membrane. Sealing the membrane with a film inhibits photobleaching of the detectable probe, such as a probe that includes a semiconductor nanocrystal, such that the detectable probe (and the target biomolecule bound to such probe) can be detected, for example visualized, at the single detectable probe level, for example single semiconductor nanocrystal level.

Figure 13:
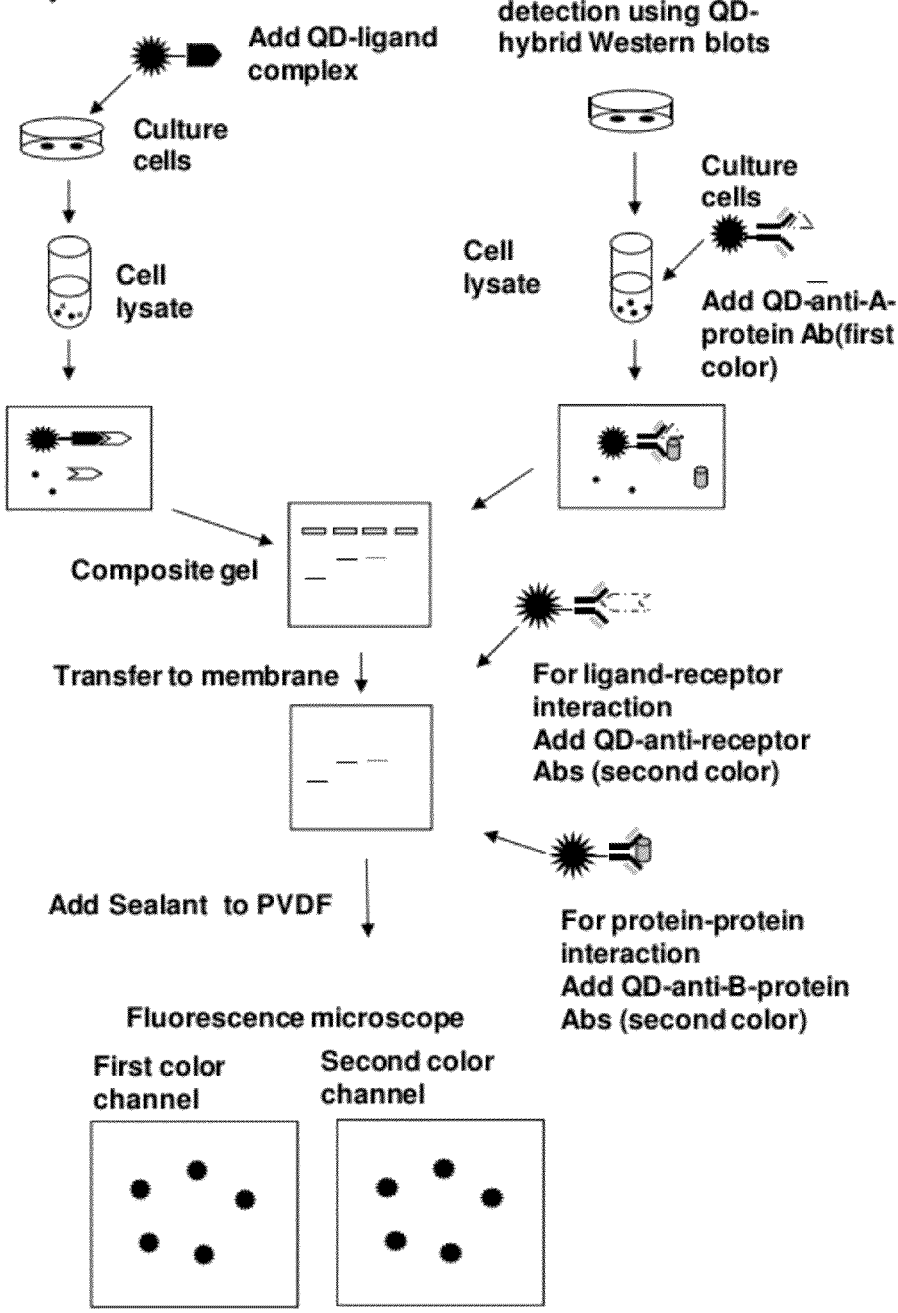
FIG. 13 is a schematic diagram of an exemplary procedure for the separation and detection of single semiconductor nanocrystals using sealed membranes.

Films can be applied as a liquid, for example a viscous liquid, although aerosol application of a film is also envisioned. Liquid films can then be allowed to flow over the surface of the membrane, effectively coating the membrane or a portion thereof and coating or encasing the semiconductor nanocrystal on the membrane or a portion of it. Alternatively, the film can be brushed, sprayed or otherwise applied to the membrane, such that the surface of the membrane is coated with the film. Applying the film effectively coats the membrane and prevents contact between the membrane and the atmosphere, such that photo-bleaching of semiconductor nanocrystals present on the membrane is inhibited. The film can be applied to one side of the membrane, both sides of the membrane, or even to a portion of one or both sides of the membrane. Exemplary procedures for inhibiting photobleaching of semiconductor nanocrystals in conjunction with the disclosed composite gels are shown in FIG. 13.

In some examples, the film can be removed without harming the biomolecules or probes bound to the molecules, for example without removing the biomolecules, probes, or both. This way a particular membrane can be contacted with multiple probes at multiple times. In particular examples, a silica-based agent is chosen that can be washed off with water or solution made with detergent, ethanol solution and the like.

C. Composite Gels

The methods disclosed herein involve the use of a composite gel for the separation of a target biomolecule of interest labeled with a nanoparticle probe, such as nanoparticle probe that includes a semiconductor nanocrystal. Composite gels suitable for the disclosed methods include a combination of cross-linkable monomers (such as acrylamide) that can be polymerized using a free-radical based system, a cross-linker (such as N,N'-methylenebisacrylamide), and a gel stabilizer (such as agarose). Suitable composite gel compositions are chosen such that the gel medium is capable of separating a target biomolecule labeled with a nanoparticle probe, such as the probes described herein.

The composite gel medium used in the disclosed methods is formed by the free-radical cross-linking polymerization of monomers and cross-linkers in an aqueous solution in which the gel stabilizer is dissolved. While not wanting to be bound by theory, the polymerized gel is assumed to have a structure in which the solidified gel stabilizer is dispersed in the three dimensional cross-linked polymer. The composite gels for use in the disclosed methods contain relatively low percentages of cross-linked polymers (such as about 0.1% to about 7.0%) in order for the pore size to be sufficiently large enough for nanoparticle labeled biomolecules to enter and be separated in the gel matrix. Such gels lack mechanical stability in the absence of a gel stabilizer. Thus, gel stabilizers are used to import mechanical stability to the gel matrix. It is believed that the gel stabilizers stabilize the polymer matrix without grossly affecting its sieving nature, because the gel stabilizers form gels with relatively large pores, whereas the cross-linked polymers form gels with relatively small pores, making the cross-linked polymers the effective sieving entity when polymerized in the presence of a gel stabilizer. This structure is one of the characteristic features of the gel medium used in the disclosed methods.

The composite gels for use in the disclosed methods include a cross-linked polymer, which is the free radical polymerization reaction product of a mixture of at least one monomer, such as at least 1, at least 2, at least 3, at least 4, or more monomers, and at least one cross-linker, such as at least 1, at least 2, at least 3, at least 4 or more cross-linkers sufficient to cross-link the monomer, thereby forming the polymer. Suitable cross-linkable monomers include acrylamide, acrylamide derivatives (such as N-methylacrylamide, N,N-dimethylacrylamide, N-(hydroxymethyl)acrylamide, diacetonacrylamide, N-hydroxypropylacrylamide, and those disclosed in U.S. Pat. No. 5,185,466), other monomers, such as those disclosed in U.S. Pat. No. 5,840,877 (for example N-acryloyl-tris(hydroxymethyl)aminomethane, or N-acryloyl-1-amino-1-deoxy-D-galactitol), or a combination thereof. Other monomers that can be used in the disclosed methods include the acrylic monomers based on sugar alcohols disclosed in U.S. Pat. Nos. 5,185,466 and 5,202,007 and those disclosed in U.S. Pat. No. 5,319,046. It is contemplated that any of the monomers described herein can be used in the disclosed methods in any combination such that the resultant polymer gel is capable of separating nanoprobe labeled biomolecules. In some embodiments, the monomer is acrylamide, N-methylacrylamide, N,N-dimethylacrylamide, N-(hydroxymethyl)acrylamide, diacetonacrylamide, N-hydroxypropylacrylamide, N-acryloyl-tris(hydroxymethyl)aminomethane, N-acryloyl-1-amino-1-deoxy-D-galactitol, or a combination thereof. In specific embodiments, the monomer is acrylamide. Composite gels useful for the disclosed methods typically contain from about 0.1% cross-linked monomer to about 7% cross-linked monomer, such as about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0% about 5.1%, about 5.2%, about 5.3%, about 5.4%, about 5.5%, about 5.6%, about 5.7%, about 5.8%, about 5.9%, about 6.0% about 6.1%, about 6.2%, about 6.3%, about 6.5%, about 6.5%, about 6.6%, about 6.7%, about 6.8%, about 6.9%, or about 7.0% cross-linked monomer. The choice of percentage can be made based on factors such as the resolution required and the monomer selected. For example, a percentage of monomer is chosen that is capable if resolving a biomolecule labeled with a nanoparticle probe.

A cross-linking agent such those described in Gelfi and Righetti *Electrophoresis* 2:213-219, 1981 or known to those of skill in the art may be employed to form the composite gels for use in the disclosed methods. Gels suitable for the disclosed methods contain a cross-linker capable of cross-linking the monomers described above. In some embodiments, the cross-linker is N,N'-methylenebisacrylamide, N,N'-propylenebisacrylamide, diacrylamide dimethylether, 1,2-diacrylamide ethyleneglycol, ethylenureabisacrylamide, ethylene diacrylate, N,N'-diallyltartardiamide, N,N'-bisacrylylcystamine, N,N'-1,2-dihydroxyethylene-bisacrylamide, N,N-bisacrylyl cystamine, trisacryloyl-hexahydrotriazine, dihydroxyethylene-bis-acrylamide, piperazine-di-acrylamide, or a combination thereof. In certain embodiments, the cross-linker is N,N'-methylenebisacrylamide (BIS). Cross linking agents are typically used in an amount of about 2% to about 30% by weigh and preferably about 3% to about 10% by weight, based on the total weight of the monomer (such as acrylamide) and the cross-linking agent. Higher percentages of cross-linker typically result in gels that increase in opacity as the percentage of cross-linker increases.

The composite gels for use in the disclosed methods include at least one gel stabilizer. In some embodiments, the gel stabilizer includes at least one polysaccharide, such as at least 1, at least 2, at least 3, at least 4, or more polysaccharides. In some embodiments, the polysaccharide is agarose or an agarose derivative, such as an agarose derivative which contains hydroxyethyl groups (for example, those disclosed in U.S. Pat. Nos. 3,956,273 and 4,319,975, or available form a commercial source, such as SEAKEM®, or NUSIEVE®), and the like. In other embodiments, the polysaccharide is cellulose or a cellulose derivative, such as hydroxyethyl cellulose, hydroxypropylmethyl, cellulose methyl cellulose, or the like. Agarose and cellulose are similar in that they are both linear polymers. They differ in their sugar constituents, in glycosidic linkages, and in the ability to form gels. While derivatized celluloses remain in solution at high and low temperatures, agarose polymers form thermally reversible gels. In other embodiments, the polysaccharide is galactomannan, dextran, starch, levan, glucan, mannan, xylan, or other polysaccharide that acts to stabilize the cross-linked polymer. In some embodiment the gel stabilizer is a combination of polysaccharides, such as a combination of any of the polysaccharides described above. In specific embodiments, the polysaccharide is agarose, a derivative thereof, or a combination thereof. Composite gels useful for the disclosed methods typically contain from about 0.1% polysaccharide to about 7% polysaccharide, such as about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0% about 5.1%, about 5.2%, about 5.3%, about 5.4%, about 5.5%, about 5.6%, about 5.7%, about 5.8%, about 5.9%, about 6.0% about 6.1%, about 6.2%, about 6.3%, about 6.5%, about 6.5%, about 6.6%, about 6.7%, about 6.8%, about 6.9%, or about 7.0% polysaccharide. The choice of percentage can be made based on factors such as the resolution required and the polysaccharide selected.

In specific embodiments, the composite gel is a mixture of agarose and cross-linked acrylamide (polyacrylamide, formed from acrylamide and N,N'-methylenebisacrylamide). In some embodiments, the composite gel includes from about 0.1% agarose to about 3.0% agarose, such as about 0.1%, about 0.2%, about 0.3%, about 0.4%, about 0.5, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% agarose and from about 0.1% cross-linked acrylamide to about 7% cross-linked acrylamide, such as about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0% about 5.1%, about 5.2%, about 5.3%, about 5.4%, about 5.5%, about 5.6%, about 5.7%, about 5.8%, about 5.9%, about 6.0% about 6.1%, about 6.2%, about 6.3%, about 6.5%, about 6.5%, about 6.6%, about 6.7%, about 6.8%, about 6.9%, or about 7.0% cross-linked acrylamide. In certain embodiments, the composite gel includes from about 0.5% agarose to about 1.5% agarose, such as about 0.5, about 0.6%, about 0.7%, about 0.8%, about 0.9%, about 1.0%, about 1.1%, about 1.2%, about 1.3%, about 1.4%, or about 1.5% agarose and from about 0.5% cross-linked acrylamide to about 3% cross-linked acrylamide, such as about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% cross-linked acrylamide.

The cross-linking polymerization can be initiated in the presence of a peroxide and/or under irradiation of ultra-violet rays. The reaction can be further accelerated by heat and irradiation with ultra-violet rays. As the polymerization catalyst, a known low temperature-polymerization initiator can be used, such as those described in Gelfi and Righetti *Electrophoresis* 2:213-219, 1981, Gelfi and Righetti *Electrophoresis* 2:220-228, 1981; and *Modern Electrophoresis* edited by Aoki and Nagai (Hirokawa Shoten, 1973). Examples of initiators include a mixture of beta-dimethylaminopropionitrile and ammonium peroxodisulfate, a mixture of N,N,N',N'-tetramethylethylenediamine (TEMED) and ammonium peroxodisulfate, a mixture of TEMED and riboflavin, a combination of a mixture of TEMED, riboflavin and hydrogen peroxide, and irradiation with ultra-violet rays. The most common system of catalytic initiation involves the production of free oxygen radicals by ammonium persulfate (APS) in the presence of the tertiary aliphatic amine TEMED.

The gel-based electrophoretic embodiments of the invention can be carried out in any suitable format, for example in standard-sized gels, minigels, strips, capillaries, and gels designed for use with microtiter plates and other high throughput (HTS) applications, and the like. Formats for gels include those described in U.S. Pat. Nos. 5,578,180; 5,922, 185; 6,057,106; 6,059,948; 6,096,182; 6,143,154; 6,162,338; 6,562,213, U.S. Patent Publications 20020134680, 20030127330 and 20030121784; and published PCT Application Nos. WO 95/27197, WO 99/37813, WO 02/18901 and WO 02/071024.

D. Nanoparticle Probes

Biological samples, including tissue samples or cultured cells (or homogenates or lysates) or other biofluids containing a single or multiple target proteins are contacted with nanoparticle probes, for example semiconductor nanocrystals conjugated to specific binding agents (such as antibodies, ligands, peptides, or aptamers).

Nanoparticles are discrete structures having dimensions less than or equal to about 1000 nm (for example, less than about 500 nm, less than about 400 nm, less than about 300 nm, less than about 200 nm, less than about 100 nm, less than about 50 nm, less than about 20 nm, less than about 10 nm, or even less than about 1 nm, for example 0.1 nm-1000 nm, such as 0.1-100 nm, 0.1-50 nm or 0.1-10 nm). Typically a nanoparticle has three dimensions on the nanoscale. That is, the particle is between 0.1 and 1000 nm in each spatial dimension, such as any integer or integer fraction between 0.1 and 1000 nm. In particular examples, the particle is between 0.1 and 100 nm in each spatial dimension, such as any integer or integer fraction between 0.1 and 100 nm.

An example of a nanoparticle is a semiconductor nanocrystal, but other examples include various polymers, silica (including dye-doped silica), and metal oxides and metals, such as iron oxide and gold nanoparticles. Examples of methods of making gold nanoparticles are disclosed in U.S. Patent Publication 2005/0120174. Nanoparticles used as the nanoparticle probes of the present disclosure can be of any shape (such a spherical, tubular, pyramidal, conical or cubical), but particularly suitable nanoparticles are spherical. The spherical surface provides a substantially smooth and predictably oriented surface for the attachment of specific binding agents such as antibodies, with the attached agents extending substantially radially outwardly from the surface of the sphere.

In particular embodiments, the nanoparticle is spaced from a specific binding agent (such as an agent that binds a target biomolecule, for example an antibody) by a linker. The specific binding agents are linked to the nanoparticle by linkers that space the binding agent slightly from the nanoparticle. As a result, multiple specific binding agents can be distributed over the surface of the nanoparticle to form a three dimensional binding surface that efficiently interacts with targets biomolecules, such as proteins.

In certain embodiments, the detectable nanoparticles are semiconductor nanocrystals, also known as quantum dots (QUANTUM DOTS™). Semiconductor nanocrystals are nanoparticles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. In quantum confined particles, the bandgap energy is a function of the size and/or composition of the nanocrystal. As the band gap energy of such semiconductor nanocrystals varies with size, coating and/or material of the crystal, populations of these crystals can be produced that have a variety of spectral emission properties. Furthermore, the intensity of the emission of a particular wavelength can be varied, thereby enabling the use of a variety of encoding schemes. A spectral label defined by a combination of semiconductor nanocrystals with differing emission signals can be identified from the characteristics of the spectrum emitted by the label when the semiconductor nanocrystals are energized. Semiconductor nanocrystals with different spectral characteristics are described in for example, U.S. Pat. No. 6,602, 671, which is incorporated herein by reference.

A mixed population of semiconductor nanocrystals of various sizes and/or compositions can be excited simultaneously using a single wavelength of light and the detectable luminescence can be engineered to occur at a plurality of wavelengths. The luminescent emission is related to the size and/or the composition of the constituent semiconductor nanocrystals of the population. Furthermore, semiconductor nanocrystals can be made highly luminescent through the use of a shell material which efficiently encapsulates the surface of the semiconductor nanocrystal core. A "core/shell" semiconductor nanocrystal has a high quantum efficiency and significantly improved photochemical stability. The surface of the core/shell semiconductor nanocrystal can be modified to produce semiconductor nanocrystals that can be coupled to a variety of biological molecules or substrates by techniques described in, for example, Bruchez et al. Science 281:2013-2016, 1998, Chan et al. *Science* 281:2016-2018, 1998, and U.S. Pat. No. 6,274,323, which are incorporated herein by reference.

Semiconductor nanocrystals can be used to detect or track a single target, such as a target biomolecule (for example, a protein expressed by a cell). Additionally, a mixed population of semiconductor nanocrystals can be used for either simultaneous detection of multiple targets (such as, different target biomolecules) or to detect particular biomolecules and/or other items of interest, such as proteins, for example in gel, such as a gel used for electrophoretic separation, a population of cells, such as cultured cells, suspensions of primary cells, or disaggregated tissues or organs. For example, compositions of semiconductor nanocrystals comprising one or more particle size distributions having characteristic spectral emissions can be used to identify particular target biomolecules of interest. The semiconductor nanocrystals can be tuned to a desired wavelength to produce a characteristic spectral emission by changing the composition and size, or size distribution, of the semiconductor nanocrystal. The information encoded by the semiconductor nanocrystals can be spectroscopically decoded, thus providing the location and/or identity of the particular item or component of interest.

Semiconductor nanocrystals for use in the subject methods are made using techniques known in the art. Examples of semiconductor nanocrystals suitable for use in the methods disclosed herein are available commercially, for example, from Invitrogen (Carlsbad, Calif.), Quantum Dot Corporation (Hayward, Calif.), and Evident Technologies (Troy, N.Y.). Semiconductor nanocrystals useful in the disclosed methods include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. The use of Group IV semiconductors such as germanium or silicon, or the use of organic semiconductors, can also be feasible under certain conditions. The semiconductor nanocrystals can also include alloys comprising two or more semiconductors selected from the group consisting of the above Group III-V compounds, Group II-VI compounds, Group IV elements, and combinations of the same. Formation of semiconductor nanocrystals of various compositions are disclosed for example in U.S. Pat. Nos. 6,927,069; 6,855,202; 6,689,338; 6,306,736; 6,225,198; 6,207,392; 6,048,616; 5,990,479; 5,690,807; 5,571,018; 5,505,928; 5,262,357 (all of which are incorporated herein in their entireties); as well as PCT Publication No. 99/26299 (published May 27, 1999).

The semiconductor nanocrystals described herein have a capability of absorbing radiation over a broad wavelength band. This wavelength band includes the range from gamma radiation to microwave radiation. In addition, these semiconductor nanocrystals have a capability of emitting radiation within a narrow wavelength band of about 40 nm or less, preferably about 20 nm or less, thus permitting the simultaneous use of a plurality of differently colored semiconductor nanocrystal probes without overlap (or with a small amount of overlap) in wavelengths of emitted light when exposed to the same energy source. Both the absorption and emission properties of semiconductor nanocrystals can serve as advantages over dye molecules which have narrow wavelength bands of absorption (such as about 30-50 nm) and broad wavelength bands of emission (such as about 100 nm) and broad tails of emission (such as another 100 nm) on the red side of the spectrum. Both of these properties of dyes impair the ability to use a plurality of differently colored dyes when exposed to the same energy source.

The frequency or wavelength of the narrow wavelength band of light emitted from the semiconductor nanocrystal can be further selected according to the physical properties of the semiconductor nanocrystal. There are many alternatives to selectively manipulate the emission wavelength of semiconductor nanocrystals. These alternatives include: (1) varying the composition of the nanocrystal, and (2) adding a plurality of shells around the core of the nanocrystal in the form of concentric shells. Thus, as one of ordinary skill in the art will realize, a particular composition of a semiconductor nanocrystal as listed above will be selected based upon the spectral region being monitored. For example, semiconductor nanocrystals that emit energy in the visible range include, but are not limited to, CdS, CdSe, CdTe, ZnSe, ZnTe, GaP, and GaAs. Semiconductor nanocrystals that emit energy in the near IR range include, but are not limited to, InP, InAs, InSb, PbS, and PbSe. Finally, semiconductor nanocrystals that emit energy in the blue to near-ultraviolet include, but are not limited to, ZnS and GaN. A nanocrystal composed of a 3 nm core of CdSe and a 2 nm thick shell of CdS will emit a narrow wavelength band of light with a peak intensity wavelength of 600 nm. In contrast, a nanocrystal composed of a 3 nm core of CdSe and a 2 nm thick shell of ZnS will emit a narrow wavelength band of light with a peak intensity wavelength of 560 nm. It should be noted that different wavelengths can also be obtained in multiple shell type semiconductor nanocrystals by respectively using different semiconductor nanocrystals in different shells, for example, by not using the same semiconductor nanocrystal in each of the plurality of concentric shells.

Additionally, the emission spectra of semiconductor nanocrystals of the same composition can be tuned by varying the size of the particle with larger particles tending to emit at longer wavelengths. For example, semiconductor nanocrystals that emit at different wavelengths based on size (565 nm, 655 nm, 705 nm, or 800 nm emission wavelengths), which are suitable for use the methods disclosed herein are available from Invitrogen (Carlsbad, Calif.).

Optionally, the emission of semiconductor nanocrystals can be enhanced by overcoating the particle with a material that has a higher bandgap energy than the semiconductor nanocrystal core. Suitable materials for overcoating are disclosed in U.S. Pat. No. 6,274,323, which is incorporated herein by reference.

These and many other aspects of semiconductor nanocrystal design are disclosed in U.S. Pat. Nos. 5,990,479; 6,114,038; 6,207,392; 6,306,610; 6,500,622; 6,709,929; 6,914,256; and in U.S. Patent Publication 2003/0165951, which are incorporated herein by reference to the extent they disclose design of semiconductor nanocrystals.

The methods disclosed herein involve nanoparticles, such as semiconductor nanocrystals, associated with a specific binding molecule or affinity molecule that binds to a biomolecule of interest, such as a biomolecule expressed by a cell, for example a protein. Without limitation, nanoparticle conjugates can include any specific binding molecules (or molecular complexes), linked to a nanoparticle, which can interact with a biological target, to detect biological processes, or reactions, as well as alter biological molecules or processes. Typically, the specific binding molecules physically interact with a biomolecule. Preferably, the interactions are specific. The interactions can be, but are not limited to, covalent, noncovalent, hydrophobic, hydrophilic, electrostatic, van der Waals, or magnetic interactions. In certain examples, the specific binding molecules are antibodies. However, one of skill in the art will recognize that the class of specific binding agents includes a wide variety of agents that are capable of interacting (binding) specifically to a biomolecule, such as a biomolecule expressed by a cell, such as receptors and receptor analogues, ligands, including small molecule ligands and other binding partners.

Nanoparticle conjugates, such as semiconductor nanocrystal conjugates, can be made using techniques known in the art. For example, moieties such as TOPO and TOP, generally used in the production of semiconductor nanocrystals, as well as other moieties, can be readily displaced and replaced with other functional moieties, including, but not limited to carboxylic acids, amines, aldehydes, and styrene to name a few. One of ordinary skill in the art will realize that factors relevant to the success of a particular displacement reaction include the concentration of the replacement moiety, temperature and reactivity. Thus, for the purposes of the present disclosure, any functional moiety can be utilized that is capable of displacing an existing functional moiety to provide a nanoparticle with a modified functionality for a specific use. The ability to utilize a general displacement reaction to modify selectively the surface functionality of the semiconductor nanocrystals enables functionalization for specific uses. For example, because detection of biomolecules and/or cells is typically carried out in aqueous media (such as buffers and/or culture media), one example of the present invention utilizes nanoparticles (such as, semiconductor nanocrystals) that are solubilized in water. In the case of water-soluble nanoparticles, the outer layer includes a compound having at least one linking moiety that attaches to the surface of the particle and that terminates in at least one hydrophilic moiety. The linking and hydrophilic moieties are spanned by a hydrophobic region sufficient to prevent charge transfer across the region. The hydrophobic region also provides a "pseudo-hydrophobic" environment for the nanoparticle and thereby shields it from aqueous surroundings. The hydrophilic moiety can be a polar or charged (positive or negative) group. The polarity or charge of the group provides the necessary hydrophilic interactions with water to provide stable solutions or suspensions of the nanoparticle. Exemplary hydrophilic groups include polar groups such as hydroxides (—OH), amines, polyethers, such as polyethylene glycol and the like, as well as charged groups, such as carboxylates (—$CO^2$—), sulfonates ($SO^3$—), phosphates (—$PO_4^{2-}$ and —$PO_3^{2-}$), nitrates, ammonium salts (—$NH^{4+}$), and the like. A water-solubilizing layer is found at the outer surface of the overcoating layer. Methods for rendering nanoparticles water-soluble are known in the art and described, for example, in International Publication No. WO 00/17655. The affinity for the nanoparticle surface promotes coordination of the linking moiety to the nanoparticle outer surface and the moiety with affinity for the aqueous medium stabilizes the nanoparticle suspension. A displacement reaction can be employed to modify the nanoparticle to improve the solubility in a particular organic solvent.

Nanoparticles, such as semiconductor nanocrystals, of varying sizes (such as, from about 1 nm to 1000 nm), composition, and/or size distribution are conjugated to specific binding molecules which bind specifically to a target biomolecule of interest. The specific binding molecule is selected based on its affinity for the particular target biomolecule of interest. The affinity molecule can comprise any molecule capable of being linked to one or more nanoparticles that is also capable of specific recognition of a particular substance (such as a target biomolecule) of interest. In general, any affinity molecule useful in the prior art in combination with a dye molecule to provide specific recognition of a detectable substance will find utility in the formation of the nanoparticle (such as semiconductor nanocrystal) probes. Such specific binding molecules include, by way of example only, such classes of substances as monoclonal and polyclonal antibodies, nucleic acids (both monomeric and oligomeric), proteins, polysaccharides, and small molecules such as sugars, peptides, drugs, and ligands. Lists of such affinity molecules are available in the published literature such as, by way of example, the *Handbook of Fluorescent Probes and Research Chemicals* (sixth edition) by R. P. Haugland, available from Molecular Probes, Inc.

In certain examples, the specific binding molecule is an antibody. More specifically, the specific binding molecule can be derived from polyclonal or monoclonal antibody preparations, can be a human antibody, or can be a hybrid or chimeric antibody, such as a humanized antibody, an altered antibody, F(ab')$_2$ fragments, F(ab) fragments, Fv fragments, a single-domain antibody, a dimeric or trimeric antibody fragment construct, a minibody, or functional fragments thereof which bind to the biomolecule of interest.

Antibodies of use with the nanoparticle probes can be produced using standard procedures described in a number of texts, including Harlow and Lane (*Antibodies, A Laboratory Manual*, CSHL, New York, 1988). The determination that a particular agent binds substantially only to the specified target biomolecule (such as a protein) can readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting can be used to determine that a given binding agent binds substantially only to the desired target biomolecule.

Shorter fragments of antibodies can also serve as specific binding agents on the nanoparticles. For instance, Fabs, Fvs, and single-chain Fvs (SCFvs) that bind to a specified protein would be specific binding agents. These antibody fragments are described as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Optionally, the specific binding agents are attached to the nanoparticle via a linker, such as a streptavidin-biotin interaction. However, many different types of linking agents can alternatively be used to link the specific binding agent to the nanoparticle. Moreover, the linking agent can be in the form of one or more linking agents linking one or more nanoparticles to one or more affinity molecules. Alternatively, two types of linking agents can be utilized. One or more of the first linking agents can be linked to one or more nanoparticles and also linked to one or more second linking agents. The one or more second linking agents can be linked to one or more specific binding molecules and to one or more first linking agents.

One form in which the nanoparticle can be linked to an affinity molecule via a linking agent is by coating a semiconductor nanocrystal with a thin layer of glass, such as silica ($SiO_x$ where x=1-2), using a linking agent such as a substituted silane, such as 3-mercaptopropyl-trimethoxy silane to in the nanocrystal to the glass. The glass-coated semiconductor nanocrystal can then be further treated with a linking agent, such as an amine such as 3-aminopropyl-trimethoxysilane, which will function to link the glass-coated semiconductor nanocrystal to the affinity molecule. That is, the glass-coated semiconductor nanocrystal can then be linked to the affinity molecule. The original semiconductor nanocrystal compound can also be chemically modified after it has been made in order to link effectively to the affinity molecule. A number of references summarize the standard classes of chemistry which can be used to this end, in particular the *Handbook of Fluorescent Probes and Research Chemicals* (6th edition) by R. P. Haugland, available from Molecular Probes, Inc., and the book *Bioconjugate Techniques* by Greg Hermanson, available from Academic Press, New York.

When the semiconductor nanocrystal can be coated with a thin layer of glass, the glass, by way of example, can comprise a silica glass ($SiO_x$ where x=1-2), having a thickness ranging from about 0.5 nm to about 10 nm, and preferably from about 0.5 nm to about 2 nm.

The semiconductor nanocrystal is coated with the coating of thin glass, such as silica, by first coating the nanocrystals with a surfactant such as tris-octyl-phosphine oxide, and then dissolving the surfactant-coated nanocrystals in a basic methanol solution of a linking agent, such as 3-mercaptopropyl-tri-methoxy silane, followed by partial hydrolysis which is followed by addition of a glass-affinity molecule linking agent such as amino-propyl trimethoxysilane which will link to the glass and serve to form a link with the affinity molecule.

These and many other techniques for linking specific binding agents to nanoparticles, such as semiconductor nanocrystals (including quantum dots), are found in U.S. Pat. No. 5,990,479 at columns 7-8, which columns are incorporated by reference.

E. Detection

Semiconductor nanocrystals-bound to the biomolecular constituent of interest can be qualitatively or quantitatively detected under illumination, such as UV-illumination, using available detection technologies, such as fluorescence scanners and/or digital cameras. If desired different specific binding agents conjugated to semiconductor nanocrystals with different spectral properties can be used to detect different cellular components.

Separate populations of semiconductor nanocrystals can be produced that are identifiable based on their different spectral characteristics. In the context of the methods disclosed herein, separate populations of semiconductor nanocrystals with different emission spectra can be used to identify different biomolecules (for example, different proteins). For example, each of two or more different populations of semiconductor nanocrystals to which specific binding agents are attached can be contacted with a biological sample, and separated on a composite gel as described herein. The characteristic emissions can be observed as colors (if in the visible region of the spectrum) or can be decoded to provide information about the particular wavelength at which the discrete transition is observed Likewise, for semiconductor nanocrystals producing emissions in the infrared or ultraviolet regions, the characteristic wavelengths that the discrete optical transitions occur at provide information about the identity of the particular semiconductor nanocrystal, and hence about the identity of biomolecule of interest. The color of light produced by a particular size, size distribution and/or composition of a semiconductor nanocrystal can be readily calculated or measured by methods which will be apparent to those skilled in the art. As an example of these measurement techniques, the bandgaps for nanocrystals of CdSe of sizes ranging from 12 Å to 115 Å are given in Murray et al., *J. Am. Chem. Soc.* 115:8706, 1993. These techniques allow ready calculation of an appropriate size, size distribution and/or composition of semiconductor nanocrystals and choice of excitation light source to produce a nanocrystal capable of emitting light device of any desired wavelength.

Methods and devices for eliciting and detecting emissions from semiconductor nanocrystals are well known in the art. In brief, a light source typically in the blue or UV range that emits light at a wavelength shorter than the wavelength to be detected is used to elicit an emission by the semiconductor nanocrystals. Numerous such light sources (and devices incorporating such light sources) are known in the art, including without limitation: deuterium lamps and xenon lamps equipped with filters, continuous or tunable gas lasers, such as argon ion, HeCd lasers, solid state diode lasers (for example, GaN, GaAs lasers), YAG and YLF lasers and pulsed lasers. The emissions of semiconductor nanocrystals can similarly be detected using known devices and methods, including without limitation, spectral imaging systems such as those disclosed in U.S. Pat. No. 6,759,235, which is incorporated herein by reference. Optionally, the emissions are passed through one or more filters or prisms prior to detection.

When stimulated with broad-band excitation these particles exhibit extended photostability. The stable fluorescent emission of semiconductor nanocrystals, unlike traditional organic dyes (such as rhodamine or FITC), has allowed free colloidal suspensions of semiconductor nanocrystals to be used to successfully attach and bind specific proteins to cells, and to identify and label proteins and cells living months after attachment without significant bleaching (Chan et al., *Science,* 1998. 281: 2016-8). The simultaneous multicolor wavelength, such as multicolor, identification of semiconductor nanocrystals permits rapid identification of probes without requiring fixation of the cells. Additionally, the wavelength of light, such as color of light, emitted can be tuned based on size of the nanoparticle.

F. Kits

Aspects of this disclosure relate to kits for the separation and detection of a target biomolecule of interest. The nanoparticle probes and composite gels can be supplied in the form of a kit for use in the separation and detection of target biomolecules of interest. In such a kit, an appropriate amount of one or more nanoparticle probes is provided in one or more containers. A nanoparticle probe may be provided suspended in an aqueous solution or as a freeze-dried or lyophilized powder, for instance. The nanoparticle probes that are supplied can be any conventional container that is capable of holding the supplied form, for instance, microfuge tubes, ampoules, or bottles. The kits can include composite gels either in a pre-polymerized state (requiring the initiation of polymerization) or as a pre-cast gel. In other particular embodiments, the kit includes equipment, reagents, and/or instructions for labeling electrophoresing and detecting the target biomolecules of interest.

The amount of the nanoparticle probes supplied in the kit can be any appropriate amount, and may depend on the target market to which the product is directed. For instance, if the kit is adapted for research or clinical use, the amount of each nanoparticle probe would likely be an amount sufficient for several labeling and electrophoresis experiments. In certain embodiments, the nanoparticle probe includes a semiconductor crystal, such as a quantum dot. In some embodiments, the nanoparticle probe includes a specific binding agent (such as an antibody, a ligand, an aptamer, or a peptide) that specifically binds the target biomolecule of interest, such as a polypeptide. In some embodiments, the detectable nanoparticle is conjugated directly to the specific binding agent. In other embodiments, a linker is used to link the detectable nanoparticle and the specific binding agent. In specific embodiments, the linker is streptavidin, avidin, biotin or a combination thereof. In some examples, the nanoparticle probe conjugated to streptavidin, avidin, or biotin, such that the nanoparticle probe can be attached to a specific binding agent that is conjugated to streptavidin, avidin, or biotin.

In some embodiments, pre-cut membranes, pre-cut filter papers, and/or pre-cut membrane/filter paper sandwiches are included in kits, for example for Western blots using the composite gels. In some embodiments, a composition capable of sealing a PDVF membrane is provided in the kit. In some embodiments, the kit does not include any composite gel.

The following examples are provided to illustrate particular features of certain embodiments. However, the particular features described below should not be construed as limitations on the scope of the invention, but rather as examples from which equivalents will be recognized by those of ordinary skill in the art.

EXAMPLES

Example 1

Microscope Imaging

This example describes microscopic imaging procedures used for the examples described below.

Images were acquired using a Zeiss Axiovert microscope equipped with 40× and 100× objectives, excitation and emission filters (Chroma), and a cooled monochrome CCD camera (Axiocam). Fluorescent and bright field optical sections of cells containing quantum dots were imaged using an ApoTome unit (Zeiss) attached to the microscope (z-section thickness of 0.4 micrometers). Contrast and brightness of the images were processed using Photoshop version 8 (Adobe). Quantum dot fluorescence blinking was measured by placing a small volume of NGF-conjugated quantum dots in cell lysates (1 microliter of 15 milligrams/milliliter protein) or freely soluble COOH-conjugated quantum dots (1 microliter of 0.01 nanomolar) onto a coverslip. Time lapse videos of quantum dot fluorescence blinking was captured at a 40 millisecond exposure time for 20 second durations. Areas of quantum dot fluorescence (0.1-0.25 square micrometers) were selected using the outline measurement tool (AxionVision 4.4, Zeiss) and the integrated intensity in each selected area was plotted as a function of time.

Example 2

Composite Polyacrylamide-Agarose Gel Preparation and Electrophoresis

This example describes exemplary procedures for the preparation and electrophoresis of composite gels, such as composite polyacrylamide-agarose gels, for use in the separation of nanoparticle probe:boimolecule complexes.

Gels composed of a mixture of polyacrylamide and agarose (2% polyacrylamide, 0.5% agarose) were prepared for fractionating unconjugated, protein-conjugated quantum dots, and NGF-quantum dots bound to target TrkA receptors. A 1% agarose solution was made by dissolving 1 gram of agarose per 100 milliliters of distilled water and boiling the solution to melt the agarose. The melted agarose was cooled to 55° C. prior to use. A 4% acrylamide solution was made with 30% acrylamide stock (acrylamide:bis=29:1) in 2× tris buffered saline (TBS) buffer containing 0.2% sodium dodecyl sulfate (SDS) and placed in a 55° C. water bath for 10 minutes. Equal volumes of the 1% agarose solution and the 4% acrylamide solution were mixed. Ammonium persulfate was added to the agarose acrylamide solution to a final concentration of 0.05%. TEMED was added at a ratio of 1:5000 (v/v) to the solution. The final 0.5% agarose-2% acrylamide solution was quickly poured into a vertical slab gel apparatus. The samples were electrophoresed under 90-150 V for 1-2 hours in 0.5× tris-borate-EDTA buffer (TBE) with 0.1% SDS. The apparent molecular weights of quantum dot-protein complexes were determined using molecular weight markers (HI MARK™, Invitrogen and PRECISION PLUS PROTEIN™ dual color standards, Bio-Rad). FIG. 4 shows quantum dot mobility and size separation (lane 1 vs. 2) and (lane 3 vs. 4) in exemplary composite agarose acrylamide gels. The digital images shown in FIGS. 4A-4B illustrate the effects of different stationary phase materials on the separation of quantum dots by electrophoresis. Images were captured with handheld black and white Polaroid camera under UV transillumination. The quantum dots are conjugated as indicated: amino pegylated quantum dots (PEG-NH); unconjugated carboxyl quantum dots (COOH-quantum dot); biotin conjugated to quantum dots (biotin-quantum dot), and streptavidin conjugated to amino pegylated quantum dots (strep-PEG-quantum dot). FIG. 4A shows the electrophoretic migration of quantum dots in a 6% native polyacrylamide gel. The quantum dot migration is severely retarded and resolution is poor. FIG. 4B shows the electrophoretic migration of quantum dots in a composite polyacrylamide-agarose gel under native conditions (0.5× TBE running buffer). Bare COOH-quantum dots and biotin-quantum dots are smaller and carry a greater negative charge density (pH 8.3) compared to streptavidin-PEG-quantum dots and NH-PEG-quantum dots and thus migrate more quickly through the gel matrix. The separation on composite polyacrylamide-agarose gels is excellent. Further separation of COOH-quantum dots and biotin-quantum dots into two subspecies highlights the resolution capability of these composite polyacrylamide-agarose gels. FIG. 4C shows the electrophoretic migration of quantum dots in a composite polyacrylamide-agarose gel under denaturing conditions (0.1% SDS in 0.5×TBE). The larger and less negatively charged NH-PEG-quantum dots and streptavidin-NH-PEG-quantum dots enter gels and exhibit good separation resolution as demonstrated by their ability to resolve the subspecies. Biotin-quantum dots and COOH-quantum dots are also well-separated but migrate too quickly under these conditions (90-150 V for 1-2 h) to resolve subspecies. Molecular weight markers give the approximate size of each quantum dot type and show that composite polyacrylamide-agarose gels can separate a wide range of quantum dot sizes (150 kD to >500 kD).

Example 3

In-Gel Separation of TrkA Receptors from Cells and Identification of Protein Interactions This example describes procedures for the separation and visualization of quantum dot protein complexes using composite polyacrylamide-agarose gels.

Nerve growth factor (NGF) is a ligand specifically binds to cellular trkA receptors and serves as a well-studied model for the tyrosine kinase family of signaling receptors. NGF-quantum dots bind specifically to trkA receptors, induce trkA downstream signaling, and are internalized and actively transported inside cell bodies.

To demonstrate that quantum dot based polyacrylamide gel electrophoresis can be used to visualize, separate, and probe protein-protein interactions, quantum dots conjugated with NGF were synthesized. PC12 cells were treated with NGF-quantum dots and it was determined if the NGF-quantum dots that are bound to TrkAs could be separated from a complex cellular lysate mixture.

NGF-quantum dots were synthesized by conjugation of β-NGF (R&D Systems) to COOH-quantum dots obtained from the Quantum Dot Corporation. Conjugation was performed by the reaction of NGF and quantum dots at a 2:1 molar ratio in 1-ethyl-3-(3-dimethylaminopropoyl)-carbodiimide (EDAC) (Sigma-Aldrich) in borate buffer (pH 7.4) at room temperature for 2 hours.

Figure 5:
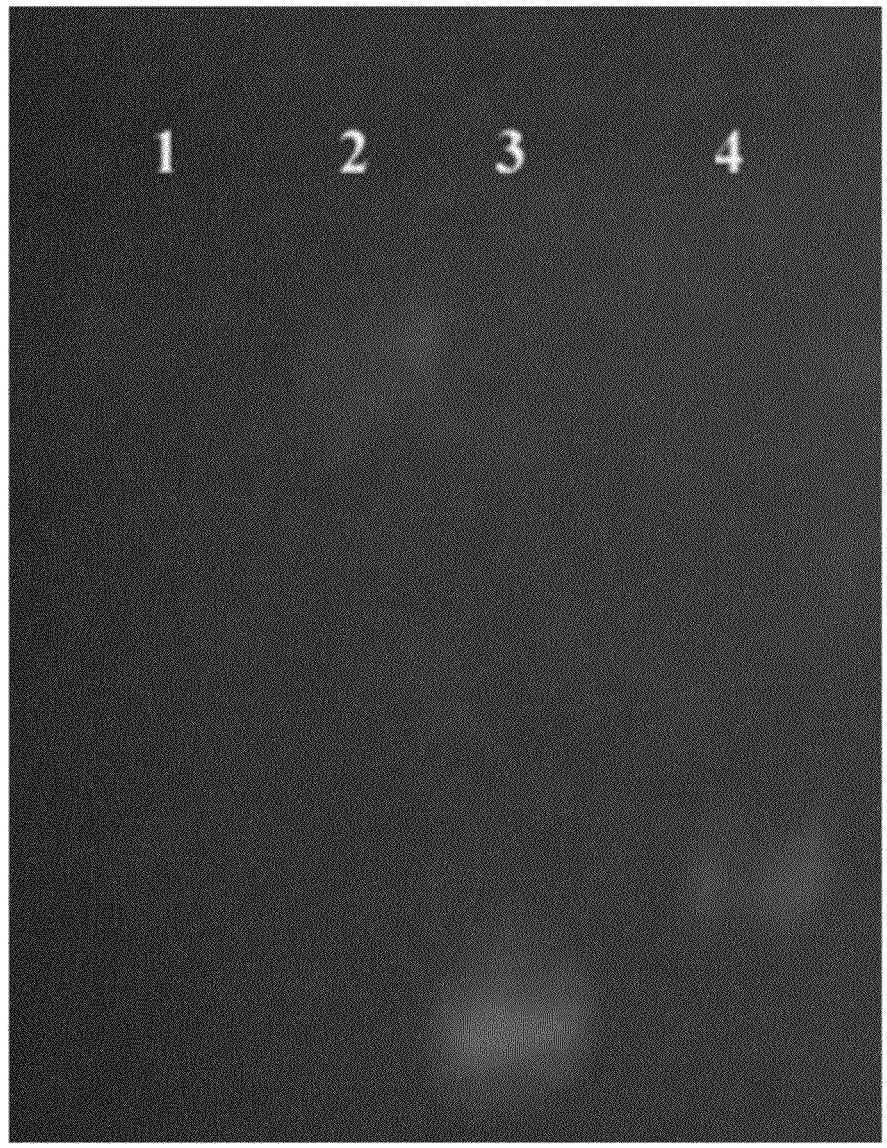
FIG. 5 is an image of quantum dots separated in gels and subsequently transferred to a PVDF membrane showing that lysates from semiconductor nanocrystal treated cells can be fractioned in a composite polyacrylamide-agarose gel system, transferred to membranes, and directly visualized under UV transillumination.

PC-12 cells expressing trkA receptors were obtained from the American Type Culture Collection (ATCC) and grown in collagen-coated T-25 flasks in RPMI-1640 supplemented with 10% horse serum, and 5% fetal bovine serum (FBS) at 37° C. Upon reaching confluence, PC12 cells were stimulated with 20 nanomolar NGF-quantum dots in serum-free media at 37° C. for 30 minutes. After washing out unbound NGF-quantum dots, PC12 cells were treated with lysis buffer (phospho buffed saline (PBS) plus 10% glycerol and 0.25% NP-40) supplemented with protease inhibitor cocktail (Sigma) and phosphatase inhibitors (2 millimolar sodium orthovanadate and 10 millimolar sodium fluoride). Insoluble materials were removed from the protein extracts by centrifugation at 13,000 rpm for 15 minutes. The protein concentration in the cell lysates was measured using a Bradford Protein Assay obtained from Bio-Rad. Cell lysates were mixed with loading buffer (40% (w/v) sucrose, 0.25% (w/v) bromophenol blue) and loaded into wells of 2% acrylamide-0.5% agarose composite gels made without SDS (native conditions) and the electrophoresis was run under 90-150 V in 0.5× TBE buffer for 1-2 hours. In-gel imaging of quantum dots was performed with a hand-held Polaroid camera under UV transillumination. Gels were transferred to PVDF membranes with transfer buffer (0.5×TBE with 20% methanol) under 100 V for 2-3 hours using an electroblotting apparatus (Mini Trans Blot Cell, Bio-Rad). The fluorescence of quantum dots on polyvinylidene fluoride (PVDF) membranes was visualized under UV transillumination. FIG. 5 is a digital image of a membrane showing that lysates from quantum dot treated cells can be fractioned in a composite polyacrylamide-agarose gel system, transferred to membranes, and directly visualized under UV transillumination. Samples were run in native conditions in gels and transferred to membranes. The image of quantum dot targeted proteins transferred to a PVDF membrane and captured with a hand held digital camera under UV transillumination. Lanes: 1) 50 micrograms of cell lysate from NGF-carboxyl quantum dot treated cells; 2) 100 micrograms of cell lysate from NGF-carboxyl quantum dot treated cells; 3) 3 microliters of 5 nanomolar NGF-carboxyl quantum dots; 4) 2 microliters of 5 nanomolar free biotin-quantum dots.

To probe NGF-TrkA interactions, PVDF membranes were blocked with 3% bovine serum albumin (BSA) and subsequently incubated with a biotinylated-polyclonal anti-TrkA antibody (C-14, Santa Cruz). This anti-TrkA antibody is directed against an intracellular peptide within the C-terminus of the TrkA receptor. The Anti-TrkA antibody was biotinylated by incubation with 500-fold excess of $NHS-PEO_4$-biotin (Pierce), followed by dialysis (SLIDE-A-LYZER®, 7 kilodalton molecular weight cut off (MWCO), Pierce) against pH 7.2 PBS to remove unbound biotin. Biotinylated anti-TrkA was added to the blotting buffer (1× tris-buffered saline (TBS) plus 0.1% Tween-20) at a final concentration of 4 micrograms/milliliter. Subsequently, membranes were washed (3 times for 10 minutes each with 1×TBS 0.1% Tween-20) and streptavidin-525 quantum dots (green) were added (1 nanomolar in blotting buffer) for 1 hour at room temperature. After washing (3 times for 10 minutes each with 1×TBS plus 0.1% Tween-20), images of PVDF membranes were captured with digital camera under UV transillumination. For analysis of dual-fluorescence emission, grayscale information from separate red and green channels of a single color image were obtained by Adobe Photoshop version 8 and pseudocolored using red and green look-up tables in Image J (NIH).

Figure 6B:
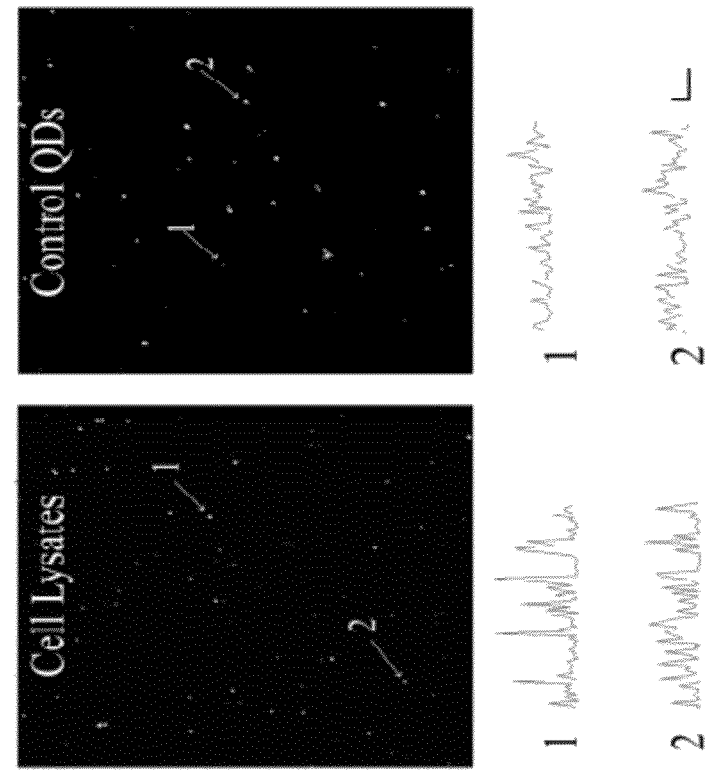
FIG. 6B is a digital image of a microscope image of NGF-semiconductor nanocrystals from cellular lysates that have been cleared from PC12 cells treated with NGF-semiconductor nanocrystals for 30 minutes.
Figure 6A:
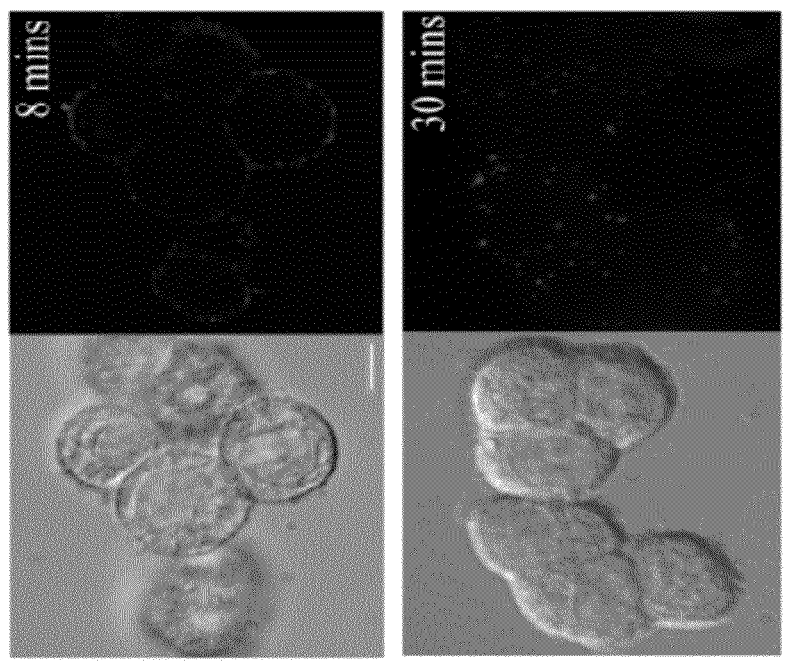
FIG. 6A is a digital image showing that PC12 cells treated with NGF-semiconductor nanocrystals for 8 minutes exhibit discrete NGF-semiconductor nanocrystals bound to TrkA receptor puncta on the cell membrane surface.

FIG. 6A shows that NGF-quantum dots can be used to identify the subcellular location of TrkAs in live PC12 cells. Cells treated with NGF-quantum dots for 8 minutes exhibit discrete NGF-quantum dots that have bound to TrkA receptor puncta on the cell membrane surface. After 30 minutes, NGF-quantum dots are endocytosed into the cellular cytosol. FIG. 6B shows a fluorescence microscope image of cellular lysate containing NGF-quantum dots that have been deposited onto a coverslip (1 microliter). Cellular lysates were obtained from cells that were treated with NGF-quantum dots for 30 minutes and appear as discrete points of fluorescence. Quantum dots were readily observed in the entire field of view, exhibiting fluorescence fluctuations or 'blinking' which is used as a standard for distinguishing single quantum dots (FIG. 6B and associated plots). These fluorescent intensity profiles are characteristic of NGF-quantum dots that are composed of individual or a few quantum dots (Grecco et al., *Microscopy Research and Technique* 65:169-179, 2004). Freely soluble COOH-quantum dots that are deposited directly onto coverslips, serve as a positive control (FIG. 6B) and as expected, exhibit blinking behavior similar to NGF-quantum dots from cellular lysates. These data indicate that quantum dots that have been exposed, then lysed and cleared from cells can be successfully retrieved without aggregation for post-analysis.

Figure 7B:
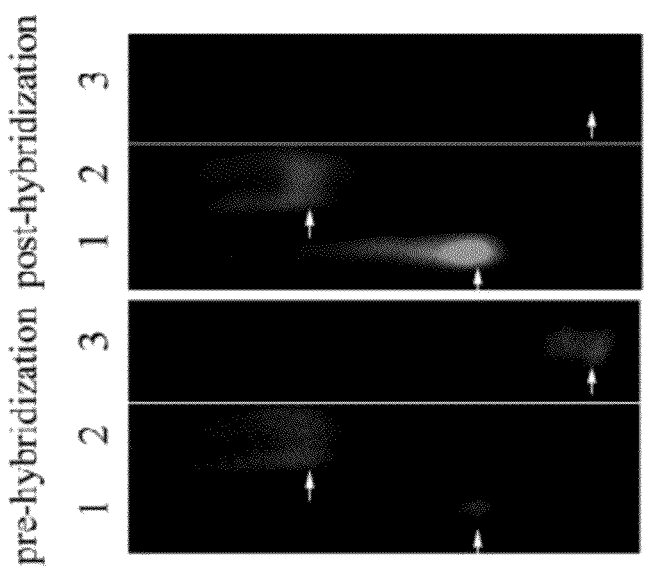
FIG. 7B is a digital image of a Western blot showing that NGF-semiconductor nanocrystals obtained from cellular lysates are complexed to TrkA receptors.
Figure 7A:
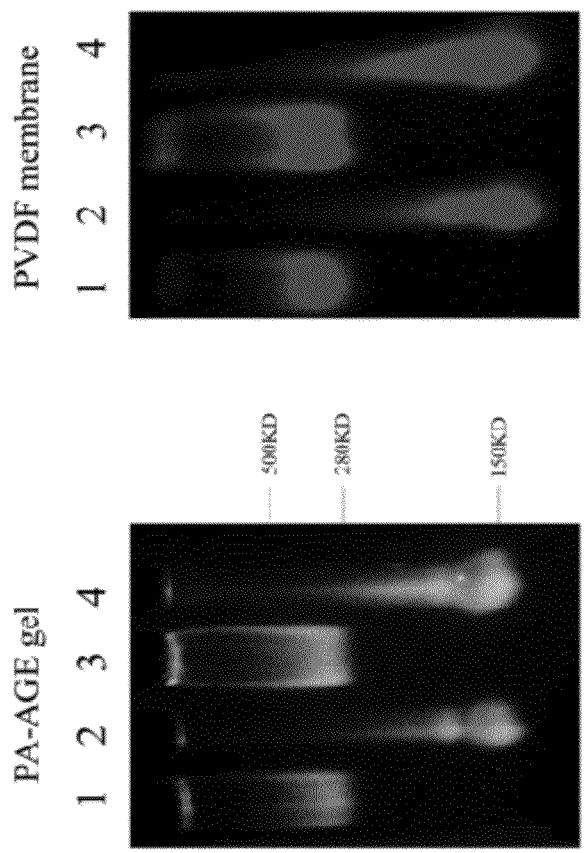
FIG. 7A is a digital image of a composite polyacrylamide-agarose gel electrophoresis separation of cellular lysates containing NGF-semiconductor nanocrystals from NGF-semiconductor nanocrystal treated cells.

Gel electrophoresis and Western blotting can be performed on NGF-quantum dot bound TrkAs in cells following identification of their subcellular localization in cells. Previous work has shown that NGF-TrkA complexes can be efficiently co-precipitated from cellular lysates of NGF-treated cells in the absence of cross-linkers (Tsui-Pierchala and Ginty, *J. Neurosci.* 19:8207-8218 (1999). FIG. 7A shows that cell lysates containing NGF-quantum dot complexes can be separated under native conditions using a composite polyacrylamide-agarose gel electrophoresis system. NGF-quantum dot treated cellular lysates show clear fractionation in polyacrylamide-agarose gels and differences in quantity at two different concentrations (lanes 1 and 3). The mobility of lysates from NGF-quantum dot treated cells is slower than that for freely soluble NGF-quantum dots, indicating that TrkA-NGF-quantum dot complexes may be purified using this quantum dot polyacrylamide-agarose gel electrophoresis technique. This purification step eliminates time and cost consuming steps involved in immunoprecipitation using Protein A/G-sepharose beads.

PVDF membrane replicas of gels made by electroblotting provide good reproducibility of polyacrylamide-agarose gels (FIG. 7A) and allow Western blot analysis for identification of proteins and their binding interactions. FIG. 7B shows an example of purification of NGF-quantum dot complexes from lysates of cells that have been treated with NGF-quantum dots for 30 minutes. Following polyacrylamide-agarose gel electroblotting, membranes were hybridized by incubation with a biotinylated anti-TrkA, washed, and incubated with green streptavidin-conjugated 525 quantum dots. It is noteworthy that this figure was compiled from data obtained from viewing multiple quantum dot colors during a single exposure. Detection of TrkA protein association with NGF can be performed by looking at overall correspondence of shape and location of the two QD colors. For example, NGF-quantum dot cell lysates and exhibits correspondence both in shape and location of red (NGF-quantum dot) and green (biotinylated anti-TrkA-streptavidin-conjugated 525 quantum dot) channels (FIG. 7B, lane 2). As a check, red biotin-conjugated quantum dots serve as a positive control and show hybridization with green streptavidin-conjugated quantum dots (FIG. 7B, lane 1). Moreover, freely soluble NGF-quantum dots serve as a negative control and do not hybridize when exposed to biotinylated anti-TrkA and streptavidin-conjugated quantum dots (FIG. 7B, lane 3), demonstrating that binding of anti-TrkA antibody to NGF-quantum dot cell lysates is specific (FIG. 7B, lane 2). These results indicate that TrkAs can be identified after fractionation in gels and that ligand-receptor interactions may analyzed on Western blots obtained from quantum dot based polyacrylamide-agarose electrophoresis gels. An alternative means of identifying protein-protein interactions is to detect these same QD color overlaps but at the single QD nanoparticle resolution using the method described in Example 8. FIG. 7A shows the gel electrophoresis separation of cellular lysates containing NGF-quantum dots from NGF-quantum dot treated cells (30 minutes) for two concentrations of cell lysates (lane 1: 40 micrograms, lane 3: 80 micrograms) shows decreased mobility in gels compared to NGF-quantum dots which migrate more rapidly though gels (lane 2: 1 microliter, 10 nanomolar NGF-quantum dots, lane 4: 2 microliter, 10 nanomolar NGF-quantum dots). The right hand image is a digital color camera image of electroblotted PVDF membranes. PVDF replicas show faithful transfer of NGF-quantum dots from gels to PVDF membranes. FIG. 7B shows that NGF-quantum dots obtained from cellular lysates are complexed to TrkA receptors. The left hand image is the red channel of a color image taken from composite polyacrylamide-agarose gel electrophoresis fractionated NGF-quantum dot cell lysates. The right hand image is the green channel of a color image of the same PVDF membrane after hybridization with biotinylated anti-TrkA, followed by streptavidin-525 quantum dots. Lane 1 contains biotin-quantum dots as a positive control. Biotin-quantum dots migrate quickly and hybridize with streptavidin-525 quantum dots. Lane 2 is NGF-quantum dot cell lysates which hybridize in the same location and pattern with anti-TrkA-biotin-streptavadin-525quantum dots. This indicates that NGF-quantum dots have bound to TrkAs. Lane 3 is a NGF-quantum dot negative control which does not hybridize with either anti-TrkA-biotin or streptavidin-525 quantum dots.

Example 4

Quantum Dot In-Gel Electrophoresis and Electroblotting

This example describes exemplary conditions for the in gel separation of quantum dots and electroblottting of quantum dot containing gels.

In-gel separation of quantum dots was performed using a hybrid mixture of polyacrylamide and agarose (2% polyacrylamide, 0.5% agarose). A 1% agarose solution was made by dissolving agarose in distilled water, boiling to melt, and cooling the mixture to 55° C. A 4% polyacrylamide solution was made with 30% acrylamide stock (29:1, acrylamide:bis) in 2× TBE buffer (pH=8.3) and then put in 55° C. water bath for 10 min. Equal volumes of the 1% agarose solution and the 4% polyacrylamide solution were mixed together, ammonium persulfate was added to 0.05% (weight/volume) final concentration, and TEMED was added to 1:5000 (volume/volume) to the solution. Composite polyacrylamide-agarose gels were quickly poured into horizontal MINI-SUB® cells (Bio-Rad) and electrophoresis were performed at 100-150 V for 0.5-1.0 hours in 1× TBE running buffer. Gel samples were then transferred to PVDF membrane by electrophoretic transfer system (MINI TRANS BLOT® cell, Bio-Rad) in 0.5× TBE with 20% methanol under 100V for 2-3 hours. Images of protein-quantum dot blotted PVDF membrane replicas were captured with a color digital camera under UV transillumination.

Example 5

Imaging of Single Quantum Dots on Transparent Membrane Blots

This example describes procedures for imaging single quantum dots present in electroblotted membranes.

Figure 12:
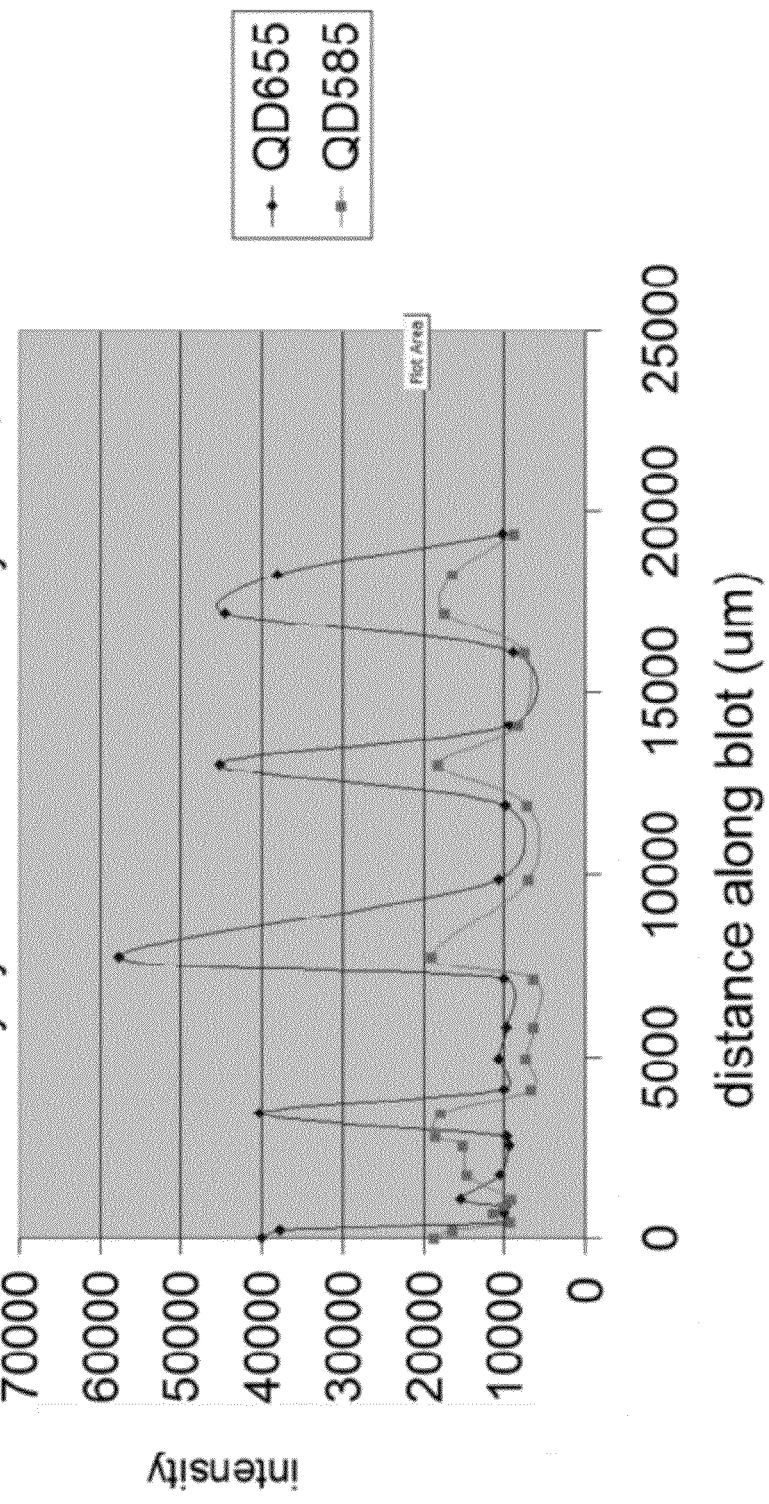
FIG. 12 a plot of the emission of two different colored nanocrystals as a function of distance in a blot showing the colocalization of fractionated and blotted nanocrystals.

Membrane electroblots were air-dried on glass slides (>2 hours) and coated with curing agent (SYLGARD® 184 Silicone Elastomer curing agent, DOW CORNING®, Midland Mich.) to render membranes translucent and to mitigate the effects of UV-induced photo-oxidation. Individual membrane blots were acquired using a Zeiss Axiovert microscope equipped with 40× and 100× objectives, excitation and emission filters (Chroma), and a cooled monochrome CCD camera (Axiocam). To obtain intensity profiles of blots as a function of blot distance (see FIG. 12), single fields of view were acquired along the vertical axis of a gel lane and 'stitched' to form a lane. The total intensity of each field of view was then integrated. Time lapse video of quantum dot fluorescence blinking was obtained to confirm the discrete nature of individual quantum dots.

Several additional agents were tested for the ability to render PVDF membranes substantially translucent (see Table 1).

TABLE 1

| Materials affect on the translucency of PVDF membrane | |
|---|---|
| Agent | Result |
| SLYGARD ® 184 silicone elastomer base (exemplary silicone)* | transparent |
| SLYGARD ® 184 silicone elastomer curing agent (exemplary silicone)# | Transparent |
| Methyl terminated poly(dimethylsiloxane), Mw 3,900 (exemplary polysiloxane) | Transparent |
| (3-Aminopropyl)triethoxy silane (exemplary silane) | Transparent |
| DMSO | solublized membrane, not transparent |
| Hexane | (dry extremely quick) Partially transparent |
| Acetone | slightly transparent |
| Glycerol | can not infiltrate to dry PVDF membrane, not transparent |

TABLE 1-continued

Materials affect on the translucency of PVDF membrane

| Agent | Result |
| --- | --- |
| Dichloromethane | transitory transparency, but high volatility |
| Methanol | not transparent |
| Ethanol | not transparent |
| Poly(vinylidene, fluoride) (solid, powder) | not transparent |

*Includes dimethylvinyl-terminated dimethyl siloxane, dimethylvinylated, and trimethylated silica and tetra(trimethylsiloxy) silane.
Includes dmethyl, ethylhydrogen siloxane-68037-59-2, dimethylvinyl-terminated dimethyl siloxane, dimethylvinylated and trimethylated silica, and tetramethyl tetravinyl cyclotetrasiloxane.

Figure 15:
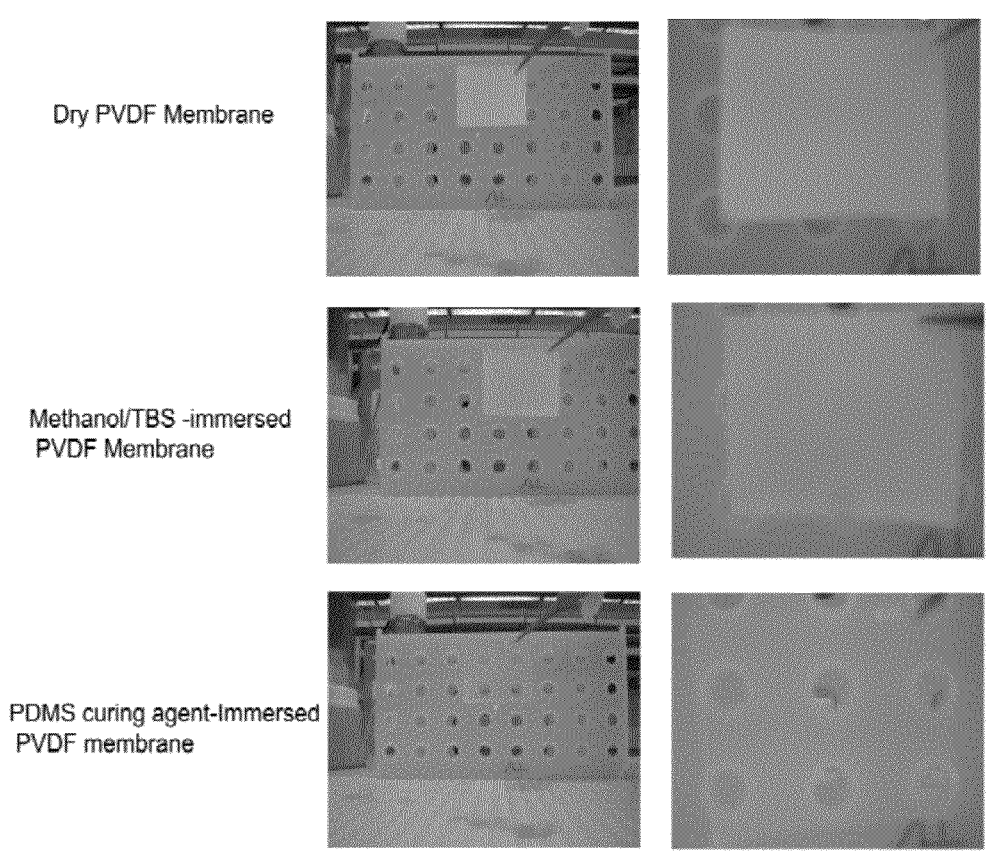
FIG. 15 is a set of digital images showing a translucency comparison of a PVDF membrane under dry, methanol/TBS buffer and a PDMF curing agent.

FIG. 15. shows an exemplary test for transparency of a PVDF membrane under dry conditions, wetting with a mixture of methanol and TBS buffer, and after interaction with SYLGARD®184 curing agent. The PVDF membrane selected has a low fluorescence and is designed specifically for use with fluorescent detection systems in Western blotting application. Background fluorescence is approximately ten times lower than that of other PVDF membranes and two times lower than nitrocellulose membranes. These PVDF membranes are nontransparent under dry conditions, and only slightly transparent after immersion in methanol for two minutes and then TBS buffer for 10 minutes. However, the membrane shows significantly improved transparency when immersed into SYLGARD®184 curing agent for 10 minutes.

Example 6

Quantum Dot In-Gel Pull-Down of trkA Receptors

NGF-quantum dots were synthesized by conjugation of biotinylated β-NGF (R&D Systems) to Strep-QUANTUM DOT®655 (Invitrogen/Quantum Dot Corporation). Conjugation was performed by reaction of NGF and quantum dot (1:1 molar ratio) in PBS (pH7.2) at 4° C. for 2 hours. PC-12 cells (ATCC) were grown in collagen-coated T-25 flasks in RPMI-1640 supplemented with 10% horse serum, and 5% fetal bovine serum at 37° C. PC12 cells were stimulated with 30 nm NGF-quantum dots in serum-free at 37° C. for 15 minutes and removing NGF-quantum dots containing medium and further incubation for 60 minutes. PC12 cells were lysed with lysis buffer (PBS, 10%glycerol and 0.25% NP-40) supplemented with protease inhibitor cocktail (Sigma) and phosphatase inhibitors (2 mM Sodium orthovanadate and 10 mM Sodium fluoride). Insoluble materials were removed from the protein extract by centrifugation (13,000 rpm, 15 minutes). Protein concentration in the cell lysates was measured using the Bio-Rad Protein Assay. Cell lysates were mixed with loading buffer (40% (w/v) sucrose, 0.05% (w/v) bromophenol blue) and loaded on PA-AGE gels under native conditions. In-gel imaging of quantum dots was performed with color camera under UV transillumination or can be performed with single quantum dot resolution using the method described in Example 8.

Example 7

Hybridization of Membrane Blots with Quantum Dots and Their Detection at Single Quantum Dot Resolution To probe for NGF-TrkA interactions, quantum dot in-gel pull downs of NGF-quantum dot-treated cells were blotted onto PVDF membranes, blocked with 3% BSA and 7 μg/ml avidin overnight at 4 degree and subsequently incubated with a biotinylated-polyclonal anti-trkA antibody (C-14, sc-11, Santa Cruz) for 2 hours at room temperature. This anti-trkA is directed against an intracellular peptide within the C-terminus of the trkA receptor. Anti-trkA was biotinylated by incubation with 500-fold excess of NHS-PEO$_4$-biotin (Pierce), followed by dialysis (slide-A-lyzer, 7KD MWCO, Pierce) against PBS (pH7.2) to remove unbound biotin. Biotinylated anti-trkA was added to the blotting buffer (1× TBS/0.1% Tween-20) at a final concentration of 4 μg/ml. Subsequently, membranes were washed (3 times for 10 minutes each with 1×TBS/0.1% Tween-20) and streptavidin-585 quantum dots (yellow)(INVITROGEN™) were added (0.25 nM in blotting buffer) for 1 hour at room temperature.

To probe for biotin-streptavidin interactions and measure the sensitivity of quantum dot in-gel pull downs, quantum dot in-gel pull-downs were performed using a series dilution of biotin-quantum dot 655 ($12\times10^8$, $6\times10^8$, $6\times10^7$, $6\times10^6$, $6\times10^5$, $6\times10^4$, $6\times10^3$, $6\times10^2$, 60,6 number of quantum dot nanoparticles), electroblotted onto to PVDF membrane and blocked with 3% BSA. Biotin-quantum dot blots were hybridized with Strep-quantum dot585 (0.25 nM) by incubation for 1 hour at room temperature, after washing 4 times for 10 minutes each with 1×TBS/0.1% Tween-20.

FIG. 8A shows that an image of quantum dots that have been fractionated in gels and electroblotted onto PVDF membranes. The bright and broad-band fluorescence excitation of quantum dots allows simultaneous multi-color signal using a simple UV table (FIG. 8A, lanes 1, 3, 5) and the transfer of quantum dots from gels to blots maintains high fidelity. When the concentration of quantum dots is diluted by a factor of ×20, the quantum dot fluorescence is not detectable on UV table (FIG. 8A, lanes 2, 4, 6). However (FIG. 8B), QD fluorescence is clearly and stably detectable at the single molecule level on PVDF membranes through rendering the PVDF membrane into a transparent polymethylsiloxane/PVDF composite through physiochemical reaction of polymethylsiloxane with the protein-QD-PVDF blot.

Example 8

Detection of Protein-Protein Interactions at the Single Quantum Dot Level

This example describes an exemplary procedure for the detection and quantification of quantum dots on the nanoparticle scale.

Figure 9:
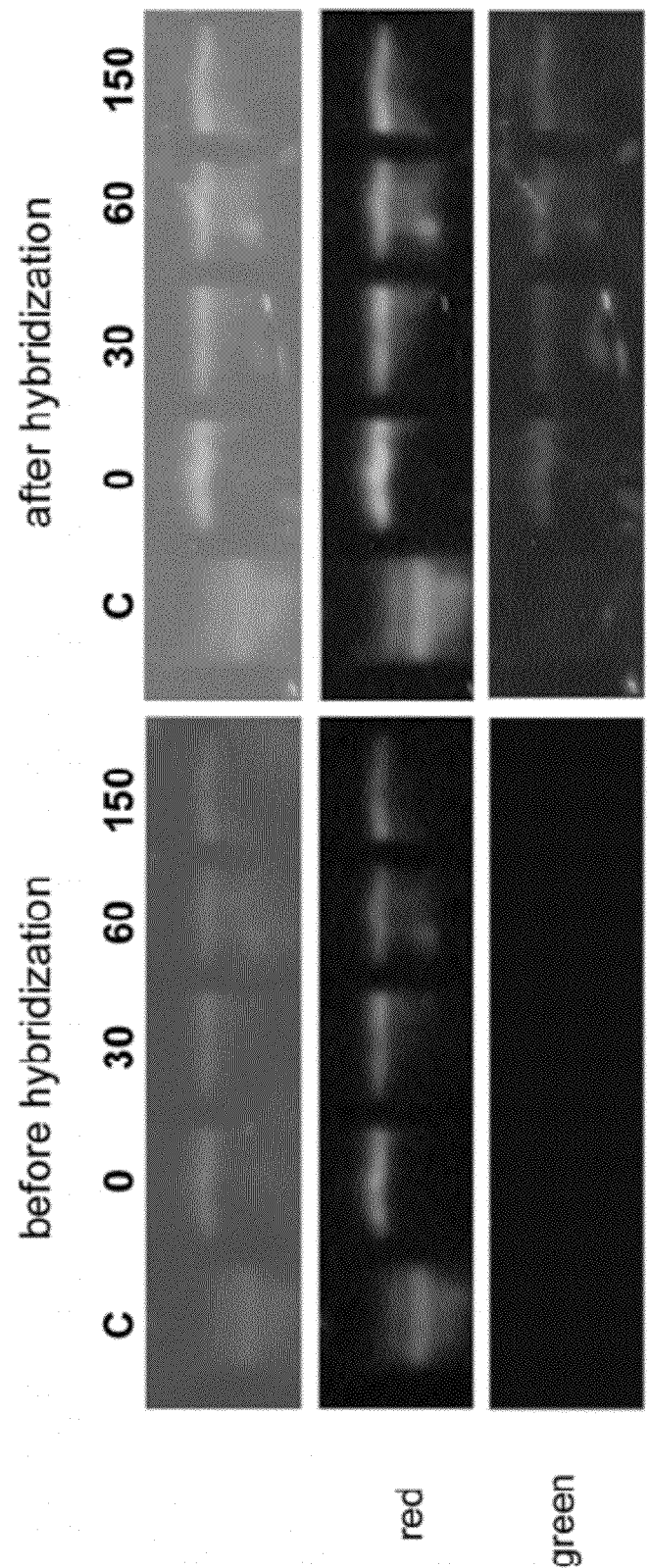
FIG. 9A is a set of digital images of Western blots showing the florescence before blotting with a secondary antibody.
FIG. 9B is a set of digital images of Western blots showing the florescence after blotting with a secondary antibody.
Figure 10:
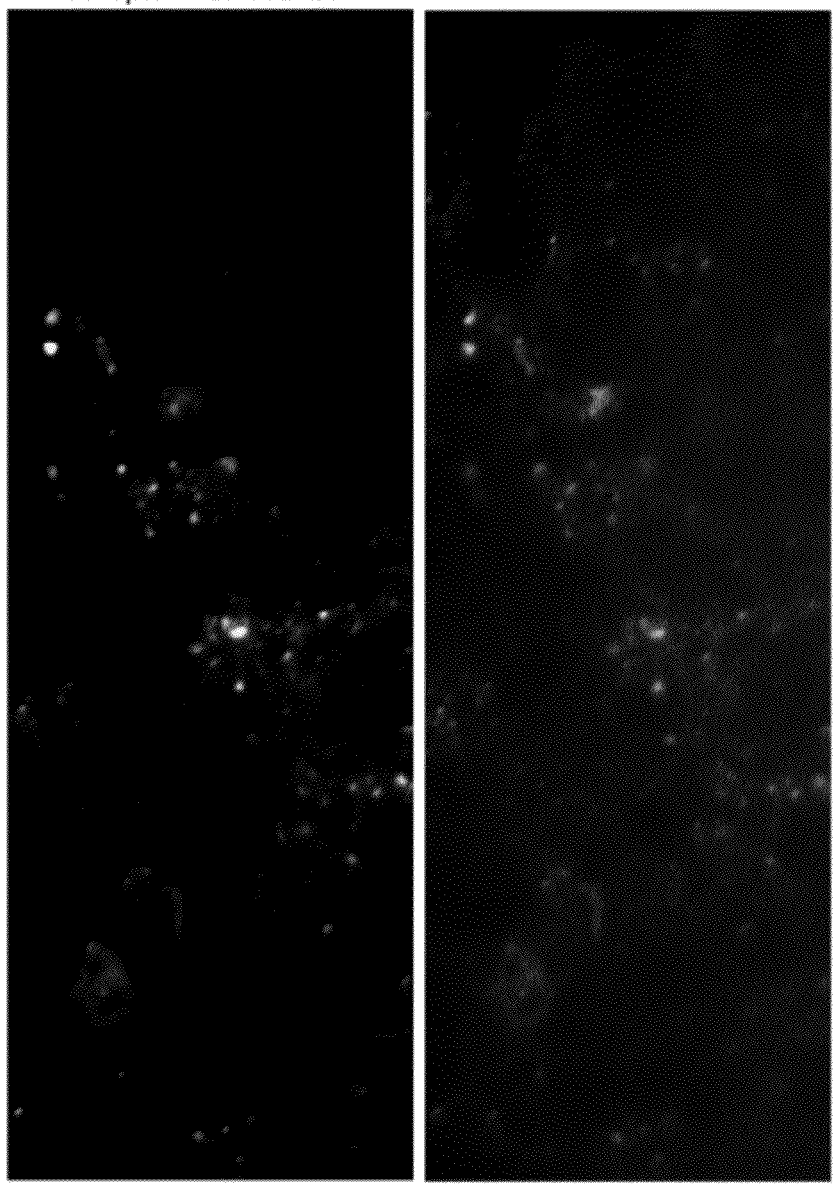
FIG. 10 is a set of digital images of Western blots showing the identification of TrkA receptor:NGF red quantum dot complexes at single quantum dot resolution, with the left panel showing fluorescence of receptor-NGF-red quantum dots and the right panel showing the fluorescence of anti-TrkA antibodies labeled with different color quantum dots.

To demonstrate and highlight the new capabilities of detecting protein-protein at the single quantum dot nanoparticle scale, quantum dot pull-downs with ligand nerve growth factor (NGF) with its cognate tyrosine kinase receptor, the trkA receptor were done as described. NGF binds to trkA and is endocytosed into cells as a ligand-receptor complex. Quantum dots conjugated with nerve growth factor (NGF) bind specifically to trkA receptors, induce trkA downstream signaling, and are internalized into cell bodies. Conventional Western blots of lysates obtained from cells treated with NGF-quantum dots show that trkA is detectable and that NGF-quantum dots stimulate a profound increase in trkAs compared to baseline trkA of cells treated with null streptavidin quantum dots. As shown in FIG. 9A quantum dot pull downs of TrkAs can be accomplished. FIG. 9B shows NGF-TrkA association as demonstrated by hybridization with anti-trkA receptor antibodies labeled with green quantum dots. FIG. 10 demonstrates that individual quantum dots can be visualized form both green quantum dot labeled NGF and the red quantum dot labeled anti-trkA receptor antibodies.

Example 9

Figure 11:
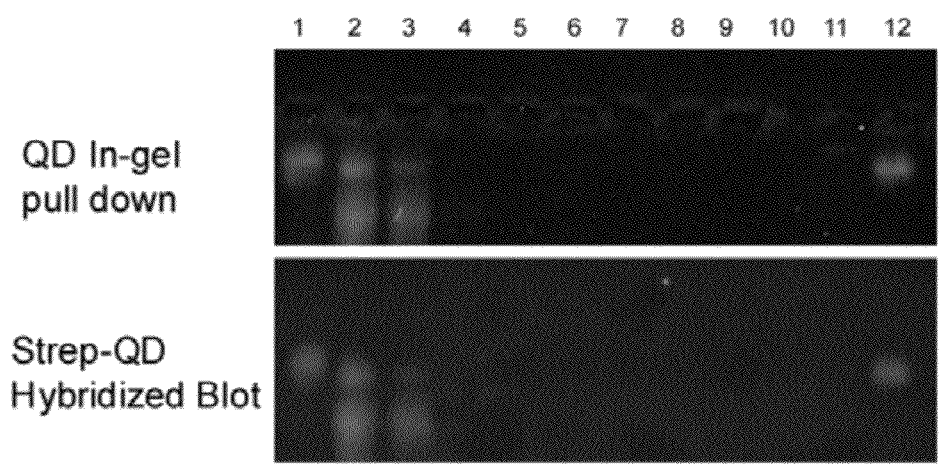
FIG. 11 is a set of digital images of Western blots showing in-gel fractionation of a serial dilution of a known number of biotin-quantum dots which ranged from about $12 \times 10^8$ to about 6 biotin-quantum dot particles.

Sensitivity of Quantum Dot Detection of Protein-Protein Interaction at the Single Quantum Dot Level To determine the sensitivity of detecting protein-protein associations at the single quantum dot level, trials were performed to detect the presence of streptavidin-biotin binding over a dilution series. FIG. 11 shows in-gel fractionation of a series dilution of a known number of biotin-quantum dots which ranged from $12 \times 10^8$ biotin-quantum dots to 6 biotin-quantum dots. Following electroblotting, blots were hybridized with streptavidin-quantum dots and biotin-streptavidin binding at the sensitivity of <60 biotin-quantum dot nanoparticles was detected.

G. Apparatus and Method for Automated Counting of Biomolecules

Substantially-improved automated detection methods are needed to detect protein samples present at trace concentrations in complex, heterogeneous tissue and biofluid samples. Counts of quantum dot-tagged proteins on immunoblots achieved optimal detection sensitivity of 0.2 pg, and a sample size of 100 cells, which was a $10^3$-fold improvement in detection sensitivity and a $10^2$-fold reduction in required cell sample, compared to traditional Westerns processed using the same membrane immunoblots. Quantum dot fluorescent blinking analysis showed that detection of single quantum dot tagged-proteins is possible and that detected points of fluorescence consist of one or a few (<9) quantum dots. The apparatus and method described herein can be useful for detecting protein or protein fragments in small populations of cells. Such detection of small numbers of cells can be useful in certain applications, such as in a solid tumor biopsy, where small numbers of cells is important.

Figure 16:
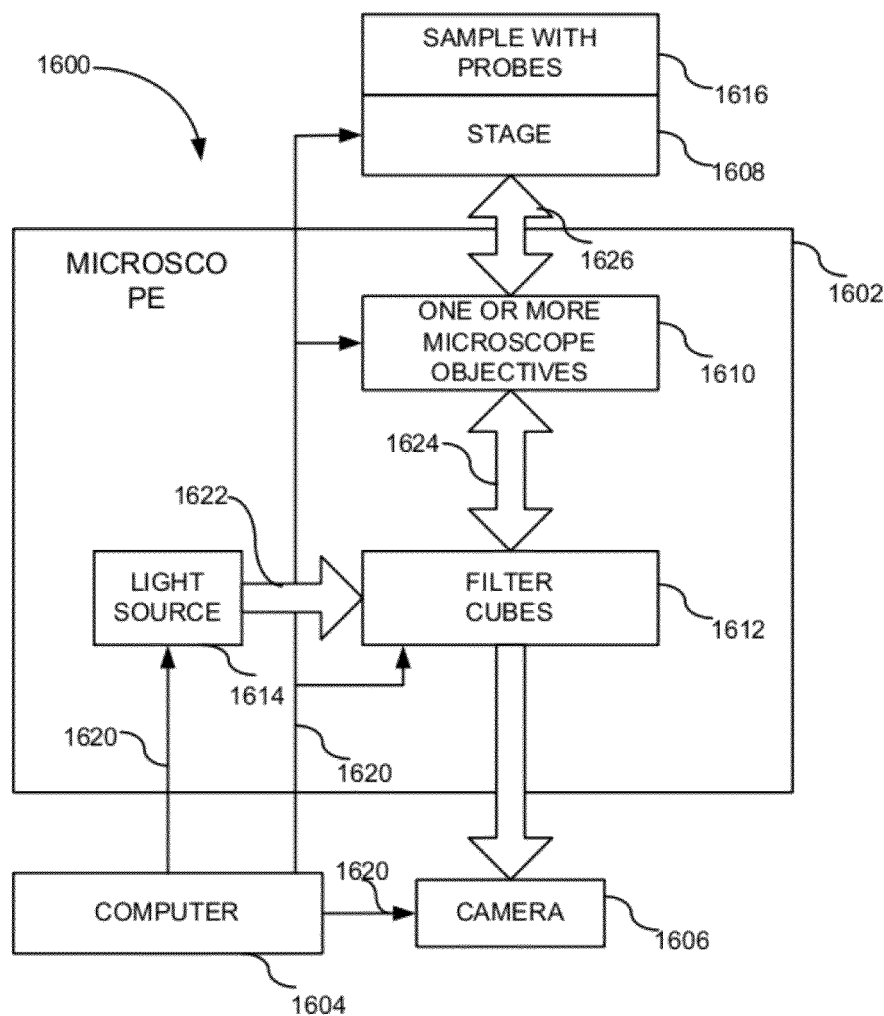
FIG. 16 is a block diagram of a system for automatically detecting and counting biomolecules.

FIG. 16 shows an embodiment of a system 1600 for automated detection and counting of biomolecules. The system 1600 can include a microscope 1602, a computer 1604, a camera 1606, and an automated stage 1608. The microscope 1602 can include one or more microscope objectives 1610, one or more filter cubes 1612 and a light source 1614. A sample 1616 containing the biomolecules (e.g., proteins) to be counted is placed on the automated stage 1608. The sample 1616 can be in a variety of formats including Western blot (which has proteins electrophoresed), Membrane blot (which is the same technique as Western blot as described herein but without using electrophoresis), and protein microarray, which uses a glass slide containing molecules of protein affixed at separate locations in an ordered manner to form a microscopic array. In any event, it is desirable that the base material upon which the biomolecules are affixed is transparent. As previously described, a wide variety of base materials can be used. One example is using an opaque PVDF membrane that is immersed in polydimethylsiloxane to make it transparent.

The computer 1604 is coupled to the camera 1606, the stage 1608, the objectives 1610, the filter cubes 1612, and the light source 1614 as shown by connections 1620, which may be established through electrical cables or wireless communication. In operation, the user turns on the light source 1614, which emits an excitation light 1622. The excitation light 1622 is at a first wavelength and encounters filter cubes 1612, which contain a dichroic mirror passing certain wavelengths and reflecting others. As shown at 1624, the filter cubes 1612 reflect desired wavelengths of the excitation light through one of the objectives as shown at 1626 to the stage 1608. The objectives can have any magnification, but a typical magnification is between 63× and 100×. The excitation light causes the nanoparticles on the sample 1616 to fluoresce, which produces an emission light. The emission light passes through the objective 1610, into the filter cubes 1612, and to the camera 1606. The emission light is at a second wavelength, different than the excitation light, and the filter cubes 1612 are designed to pass light at the second wavelength to the camera 1606. The camera 1606 captures an image of the excitation light in response to a control signal from the computer 1604. The stage 1608 can then be controlled by the computer 1604 to position the sample at a new X-Y-Z position and the process is repeated.

Figure 17:
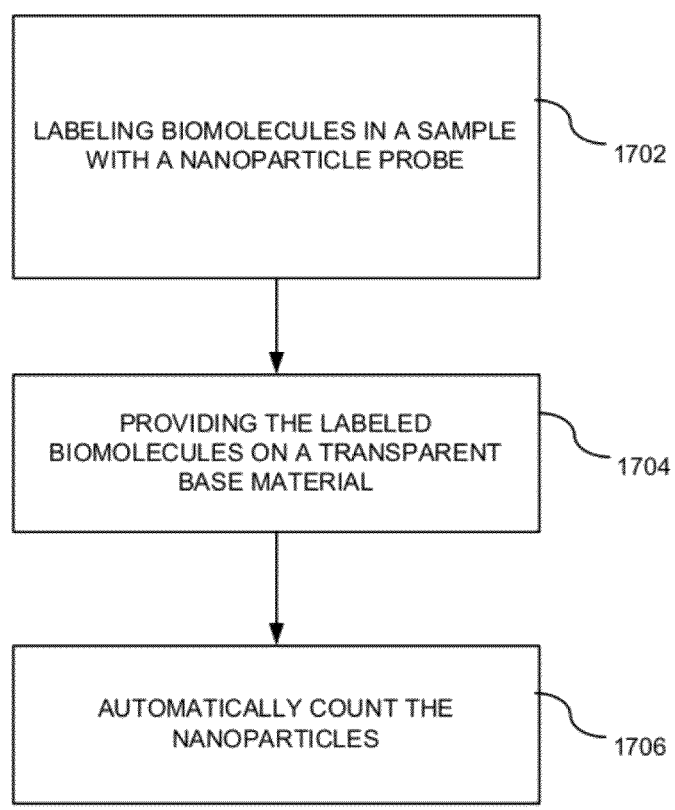
FIG. 17 is a flowchart of a method for automatically counting biomolecules.

FIG. 17 shows an embodiment of a method for counting biomolecules. In process box 1702, biomolecules are labeled in a sample with nanoparticle probes, such as quantum dots. In process box 1704, the labeled biomolecules are provided on a transparent base material, such as a membrane or glass. In process block 1706, the computer 1604 automatically counts the nanoparticles using processing software. Automated counting as described herein allows for counting of discrete groups of nanoparticle probes (e.g., any number between 2-100, such as 5, 10, 50, etc.) or single nanoparticle probes.

Figure 18:
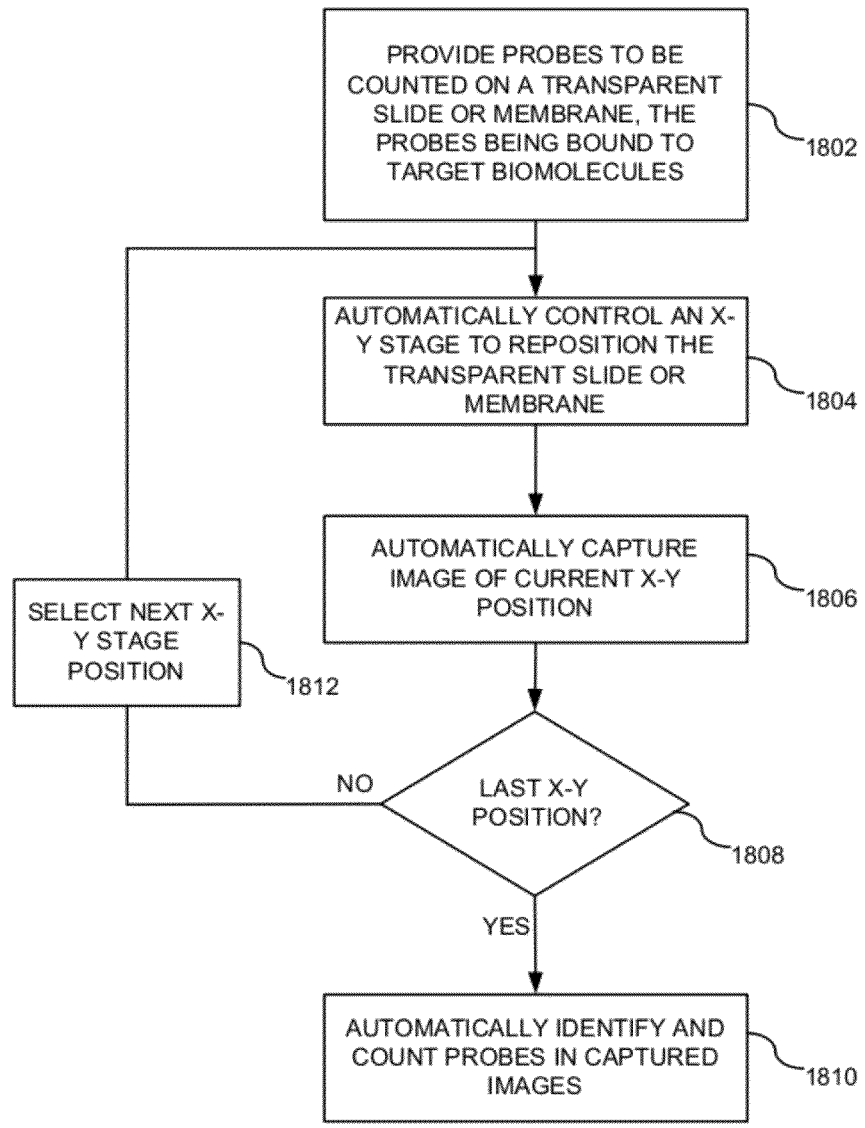
FIG. 18 is a flowchart of a method for capturing images in differing X-Y locations using the system of FIG. 16.

FIG. 18 shows a more detailed flowchart of a method for counting biomolecules. In process box 1802, the probes to be counted are provided on a transparent slide or membrane in one of the formats previously described. In process box 1804, the computer 1604 automatically controls the stage 1608 to position the stage in the proper X-Y location. Additionally, the Z location of the sample can also be set. If Z control is provided, a first focal plane can be used as a reference and then an estimate is made for changes in the focal plane. The sample can be considered to have different zones to be captured and the number of zones depends on the dimension of the sample and the magnification of the objective. In process block 1806, the image of the current X-Y location is captured using the computer-controlled camera 1606. In decision box 1808, a check is made by the computer 1604 to determine if the last X-Y position has been captured. If so, in process box 1810, the probes are automatically identified and counted for each of the images. In not, in process box 1812, the stage 1608 is automatically moved to the next X-Y position (i.e., the next zone) and the process is repeated until all of the desired X-Y positions have been captured.

Figure 19:
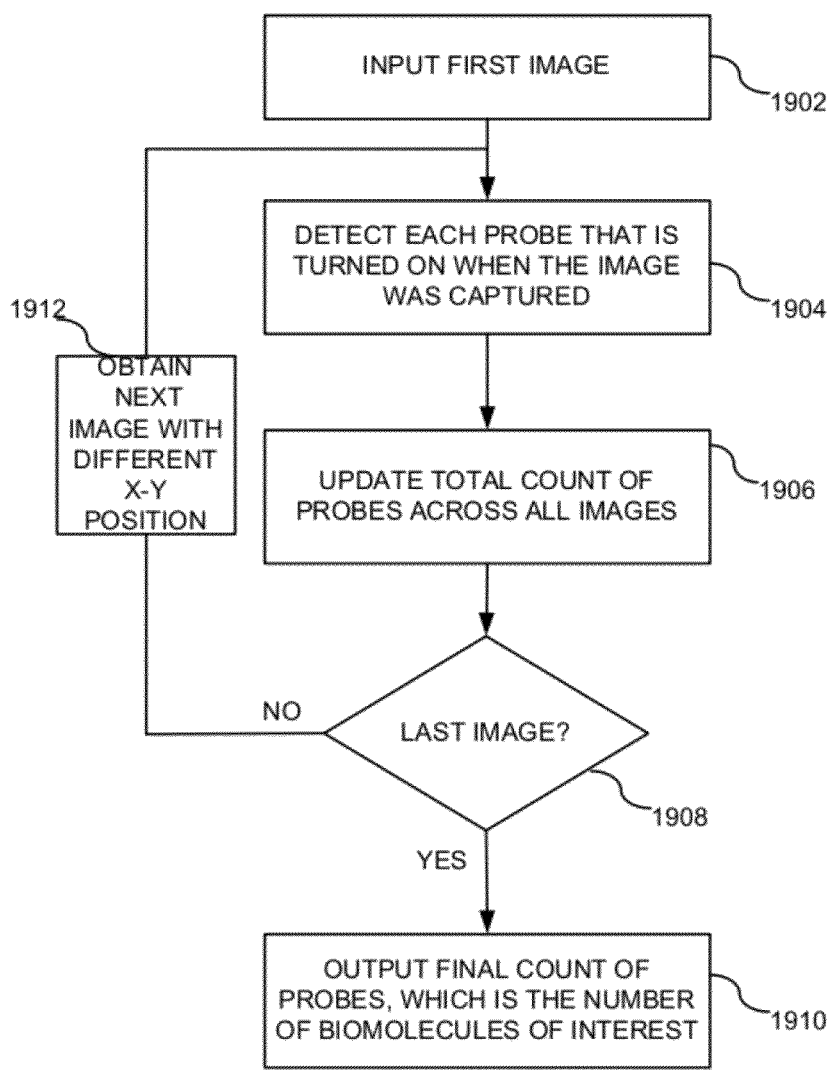
FIG. 19 is a flowchart of a method for counting biomolecules across multiple images.

FIG. 19 is an embodiment of a method for counting the labeled biomolecules across multiple images. For example, FIG. 19 can be an expansion of process box 1810 and can be performed after all of the images are captured. Alternatively, the process of FIG. 19 can be performed after each image is captured. In process box 1902, the first image is input into the software. The image is typically stored in a standard format (e.g., TIFF). In process box 1904, each probe that was turned on is identified or otherwise detected in the image. Probe detection can be based on publicly available algorithms, such as those described in Crocker, J. C. & Grier, D. G., *Methods of Digital Video Microscopy for Colloidal Studies*. J Colloid Interface Sci 179 (1996). In process block 1906, the detected probes are added to a total count of probes. In decision box 1908, a check is made to determine if all of the captured images have been processed. If yes, the final count is output (process box 1910), which is the number of detected probes across all images, wherein the images are taken at different X-Y locations. The number of detected probes is considered to be the number of biomolecules. A further error factor can be added to the total count. The error factor (also called blinking factor) takes into account probes that are in the off cycle of blinking, as further described below. If decision box 1908 is decided in the negative, then in process box 1912, the next image with a different X-Y position is obtained and the identification and total count (process boxes 1904, 1906) are performed again.

Figure 20:
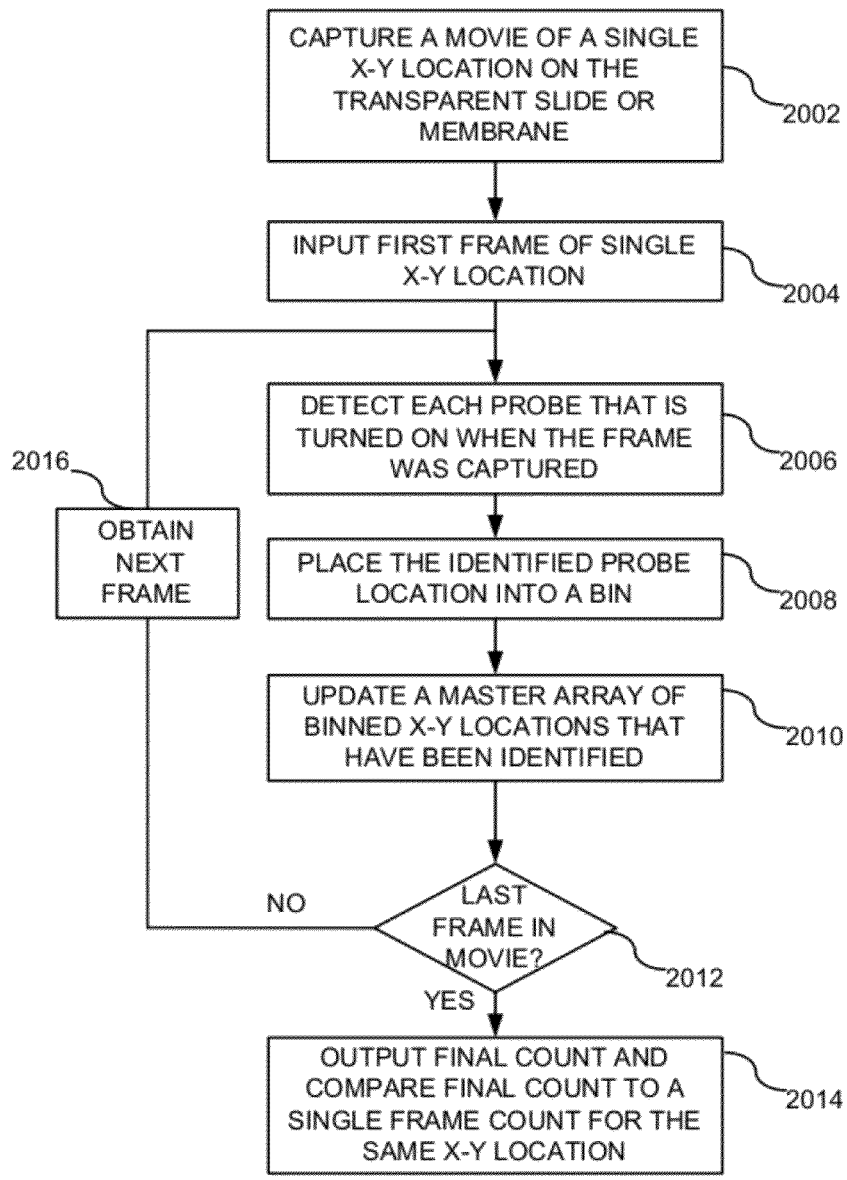
FIG. 20 is a flowchart of a method for counting biomolecules using a movie in order to obtain an error factor that can be used to supplement the count of FIG. 19.

FIG. 20 is a flowchart of a method for generating an error factor. In any captured image there are likely a certain percentage of probes that are in the off cycle of blinking. As a result, it is beneficial to detect how many probes are generally missing from the total count in any captured image. Such a number can be used as an error factor to be added to the total count to obtain a more accurate estimate of the number of biomolecules. In process box 2002, a movie is captured of a single X-Y location on the transparent slide or membrane. The movie can, for example, include any desired number of frames (e.g., 500 frames). In process box 2004, a first frame is input for analysis. In process box 2006, the image is searched for probes using the methods previously described. In process box 2008, the detected probes are placed into a bin using a rounding process. For example, the bin can be one pixel wide so that if the probe was detected at an intermediate pixel location (e.g., pixel 45.6), the detected probe can be rounded to the nearest pixel. In this way, probes will not be counted multiple times due to slight variations between images. In process box 2010, a master array of binned X-Y locations is updated to indicate the detected probes. The array can have a single bit to indicate whether a probe was found in the bin at a particular location. In decision box 2012, a check is made whether this is the last frame in the movie. If so, the final count, which is the total number of binned probes in the array, is compared to a final count for a single image at the same X-Y location. The difference is considered an error count that can be added to a final count obtained after box 1910 in FIG. 19. If decision box 2012 is answered in the negative, then the next frame is retrieved and process boxes 2006, 2008, and 2010 are repeated. In short, multiple frames are considered for a single X-Y location and the probes are binned to avoid double counting.

FURTHER EXAMPLES

Example 10

Before explanation of the particular example, it is useful to have a more detailed description of FIGS. 21-25.

FIG. 21 illustrates counts of single point of QD fluorescence that allow accurate quantification of fluorescent blot bands at low concentration. A) Schematic of Single Point Quantum Dot (SPQD) Western Immunoblotting. B) Detection of discrete QD fluorescence is possible on PDMS-treated PVDF membranes but not using opaque PVDF membranes. Left hand side: opaque and transparent nature of the PVDF and PDMS-PVDF membrane, respectively, shown by simultaneously scanned images of these membranes placed atop a printed scale bar on a green background. Right hand side: transparent PDMS-PVDF membranes enable quality, discrete QD detection that is not possible with opaque PVDF membranes. Microscopic images taken with a CCD camera mounted on a fluorescence microscope under same conditions; scale: 7.2 um. C) Top row: After gel separation and electrotransfer of two QD bioconjugate species, macroscopic UV illumination shows that relatively high concentrations of QDs are visible but low concentrations of QDs are not (streptavidin-QD655s: lanes 1 and 2: 2.5 nM and 25 pM each at 3 µL; biotin-QD655s: lanes 2 and 4: 2.5 nM and 25 pM each at 30). Bottom row: After PDMS-treatment of PVDF membrane blots, microscope images taken of membrane at the location of bright macroscopic QD bands shows the presence of discrete QD fluorescence. Almost all points of QD fluorescence showed blinking at all loading concentrations, an indicator that each fluorescent count is comprised of individual or small numbers of QDs. Image acquisition and processing are the same for all images. Right hand panel: Plots of lanes containing low QD signal (lanes 1 and 3) are graphed as # of QD counts/micrograph vs. distance from loading well, illustrating that QD counts accurately reflects that of macroscopic blots seen by eye at higher QD concentrations (lane 2, 4). Graph represents 180 micrographs taken in a band area of 3.2 mm×1.9 mm.

FIG. 22 illustrates that single Point Quantum Dot Western Immunoblotting achieves enhanced protein detection sensitivity. A) Purified protein detection performed using SPQD for nerve growth factor (NGF) shows a detection sensitivity of 0.01 ng. Plot inset shows QD counts for the lowest protein amounts (0.1 and 0.01 ng). SPQD Western QD counts were acquired from a total of n=3 independent experiments in a band area of 3.3 mm×0.50 mm (n=1) and 3.3 mm×1.9 mm (n=2). Plot symbols: unfilled triangles, independent trials; solid triangles, mean. B) In comparison, traditional Western blots performed using the same NGF-fractionated membranes as in A show a detection threshold of 10 ng. C) Detection threshold of SPQD blots for purified protein standards of Factor XI show a detection sensitivity of 0.2 pg. SPQD Western QD counts were acquired from n=4 independent experiments in a band area of 1 mm×3 mm. Plot inset shows QD counts for the lowest protein amounts (20 -0.2 pg). Plot symbols: unfilled triangles, independent trials; solid triangles, mean. D) Traditional Western blots performed using the same Factor XI membranes in C show a detection threshold of 0.2 ng. All measurements were normalized by subtracting QD counts from parallel blank control lanes containing buffer in each experiment.

FIG. 23 illustrates that single point Quantum Dot Western Immunoblotting provides a significant reduction of the amounts of required cell sample. A) Cellular protein detection performed for TrkA receptor protein in PC12 cells using SPQD and traditional Western blots. TrkA levels measured for steady-state (NGF−) and stimulated (NGF+) levels. SPQD Western signal is detection threshold is 0.05 ng (100 cells). Small sampled region of the membrane is shown to demonstrate the discrete nature of QD counts of TrkA over all range tested (Scale: 6.4 µm). The traditional Western blots signal is 50 µg of cell sample (100,000 cells). Similar cell amounts are required for abundant actin protein (loaded into parallel lanes of same membrane). B) TrkA levels plotted as a function of amount of cell sample. TrkA signal quantified as arbitrary integrated intensity (traditional Westerns) and QD counts (SPQD blotting) SPQD blotting results computed from band area of 3.3 mm×1.9 mm. All values normalized by subtraction from parallel blank control lanes loaded with buffer. C) Graph of TrkA upregulation (TrkA$_{NGF+}$/TrkA$_{NGF-}$). TrkA upregulation is detectable by SPQD Westerns over the entire range of 0.05-50 µg ($10^2$-$10^5$ cells) compared to the Western blot threshold of 50 µg ($10^5$ cells).

FIG. 24 illustrates that SPQD Western Immunoblotting detects cellular CrkL protein in 100 Cells. A) Detection threshold for SPQD blots using total-CrkL and phosphorylated-CrkL antibodies in BCR-ABL positive CML cells, both show a detection threshold for 100 cells. Plot inset shows QD counts for the lowest cellular amounts (100 and 10 cells). SPQD Western QD counts for both CrkL antibodies were acquired from 3 independent experiments in a band area of 4 mm×1. Plot symbols: unfilled symbols, independent trials; solid symbols, mean. B) In comparison, traditional Western blots using the total-CrkL and phosphorylated-CrkL antibodies show a detection threshold of 100,000 and 10,000 cells, respectively. Blots were performed using the same cellular lysates and gels were run simultaneously in each experiment.

FIG. 25 illustrates QD blinking analysis of Western Blots of purified and cellular protein and shows populations of detected QD fluorescent counts composed of a single, few, and multiple QDs. A) A single frame from movies of SPQD Western blots processed with purified Factor XI and cellular phospho-CrkL protein show examples of: background fluorescence (b, blue), a single QD (s, green), a few QDs (f, purple), and many QDs (m, red). B) Time-varying intensity traces corresponding to each circled location shown in A. Dashed lines in each trace indicate the mean background intensity value for each frame. Fluorescence counts associated with single QDs exhibit square-wave ON-OFF blinking behavior, counts associated with few QDs exhibit intensities that return to the mean background, and counts associated with many QDs exhibit a wide range of variance and intensity values that do not return to the mean background intensity. C) Histograms plot the distribution of intensities for the profiles shown in B. QD counts composed of a single QD exhibit bimodal ON-OFF blinking (s, green) which overlapped with the background distribution of intensities (b, blue). QD counts composed of a few QDs do not show a bimodal distribution (f, purple), but have a distribution of intensity values that overlap with the background intensity (b, blue). QD counts composed of many QDs show a distribution of values located above the mean background intensity (m, red). These distributions also exhibited a wide range of variances (compare red histograms for Factor XI and phospho-CrkL). D) Bar graphs show the population of QD counts containing single, few, and many QDs. Single QDs make up 13.40% and 6.36% of the total QD counts for Factor XI blots (n=1515, lanes loaded with 2 and 0.2 ng) and phospho-CkrL blots (n=707, lanes loaded with 10,000 cells), respectively. The majority of all QD counts were composed single or a few (<9 QDs, see text): 72.48% and 78.92% for purified Factor XI and cellular phospho-CrkL, respectively.

In this particular example, a method is used to image discrete QD-tagged proteins that are immobilized on membranes by converting opaque PVDF membranes into optically transparent siloxane-treated PVDF membranes. This enables analysis of Western blot signals at the resolution of discrete fluorescent points of QD tagged-protein and is a contrast to traditional analysis of bulk blot bands. The capability to count discrete QD-tagged proteins allows significant increase in sensitivity and reduction in amount of cell sample.

The method of detecting and counting discrete QDs in transparent PVDF membranes, called single point quantum dot (SPQD) Western blotting, is outlined in FIG. 21A. One step of this method is converting the PVDF membranes from an opaque to optically transparent state, thus allowing high-quality detection and quantification of QD-tagged proteins. Single QDs can be detected on glass slides using a fluorescent microscope. However stable fluorescence detection of single QDs on PVDF membranes is more difficult because PVDF membranes are opaque (FIG. 21B) and existing methods using alcohol-based solvents (e.g. methanol) for producing semi-transparent membranes are not only poor for detecting single QDs, but are also not compatible with preserving membrane-adsorbed protein for subsequent immunoblotting steps.

To image proteins tagged with QDs on PVDF membranes, it is to immerse dry, opaque PVDF membranes in polydimethylsiloxane (PDMS) mixtures such as PDMS curing agent. The PDMS curing agent penetrates dry PVDF membranes and creates an optically transparent PDMS-PVDF membrane mixture that allows single QDs to be detected using a simple fluorescent microscope (FIG. 21B, left hand column). As can be seen in FIG. 21B, righthand column, QDs cannot be sufficiently detected on opaque PVDF membranes. Using PDMS-PVDF membranes, it is possible to detect single points of QD fluorescence that are stable and persist for more than 10 minutes under continuous excitation. In contrast, QD fluorescence rapidly quenches (<1 minute) in buffers, such as those used in traditional Western immunoblotting protocols. PDMS-PVDF membranes can be stored in a cold room (4° C.) and can be re-imaged with single QD detection quality for long periods after blot preparation (3-6 weeks).

The mechanism of the PDMS-induced PVDF transparency is a physical interaction between PDMS and PVDF. One possible transparency technique is to use Sylgard 184 silicone curing agent, which contains a combination of dimethyl, methylhydrogen siloxane; dimethylsiloxane dimethylvinyl-terminated and tetramethyl tetravinyl cyclotetrasiloxane; however, other polydimethylsiloxane mixtures such as methyl-terminated polydimethylsiloxane, or the combination of siloxanes present in the base portion of Sylgard 184 elastomer are also effective in converting PVDF to transparent PDMS-PVDF membranes. Physical penetratration of the PDMS agent into the disordered and fibrous PVDF membrane can provide a better match in the index of refraction at the PDMS-PVDF interface compared to the index of refraction at the air-PVDF interface, thereby decreasing scattering and increasing transparency of the membrane.

The new capability to detect single points of QD fluorescence makes possible the measurement of QD fluorescent bands at lower concentrations that would otherwise remain invisible. FIG. 21C shows that while it is possible to detect macroscopic bands of fractionated QD bioconjugates (biotin-QD655s, and streptavidin-QD655s) at relatively high concentrations (2.5 nM: lanes 2 and 4) using a UV transillumination table, in contrast, QD bioconjugates are not visible at low concentrations (25 pM: lanes 1 and 3). After the opaque PVDF membrane was converted to a transparent PDMS-PVDF membrane, single points of QD fluorescence could be resolved at both high and low QD concentrations (bottom panel, FIG. 21C).

Figure 22A:
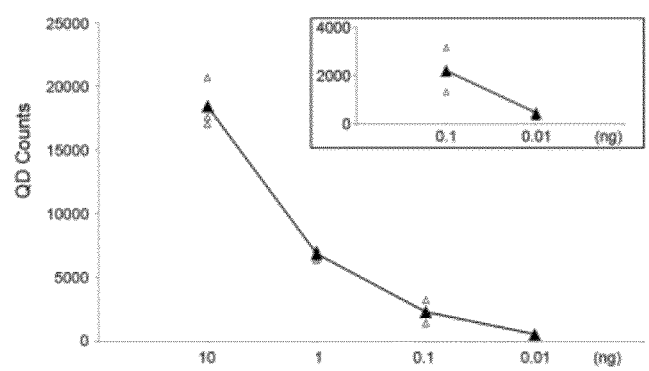
FIG. 22A-D includes plots of QD counts and digital images showing detection thresholds.
Figure 22B:
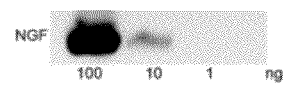
Figure 22C:
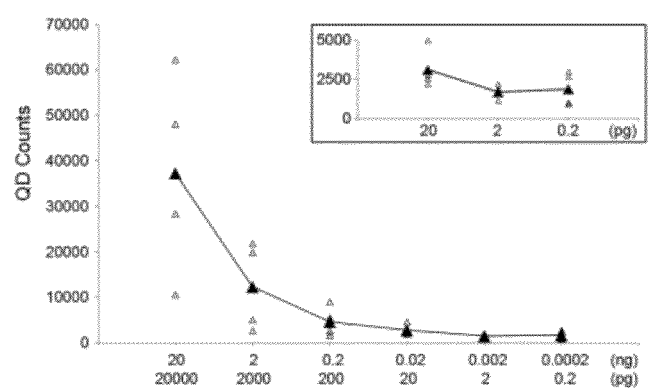

Based on several observations, the discrete points of QD fluorescence that were detected were an accurate representation of blot bands typically measured by averaged integration (e.g. densitometry). First, lanes loaded with lower quantities of QD bioconjugates (lanes 1, 3) contained fewer points of discrete QD fluorescence than lanes loaded with higher amounts of QD bioconjugates (lane 1, 3). Second, automated scanning along the length of the lanes containing low amounts of QDs (FIG. 22C, lanes 1, 3) showed that the QD distribution corresponded to the distribution visible by eye of high density QD bands (FIG. 22C, right panel). Automated counting for relatively high numbers of QDs (lanes 2, 4) can be difficult due to the dense grouping of individual QDs and due to the contribution of diffuse fluorescence emitted by out-of-focus QDs (during electrotransfer, QDs enter PVDF membranes over a depths of ~1 um). Finally, virtually all discrete points of QD fluorescence exhibited fluctuations, indicating that counts were composed of individual or small numbers of QDs. A standard used to identify single QDs from a group is QD fluorescent 'On-Off' blinking: evidence that QD fluorescence intensity returns to a dark 'Off' state that is indistinguishable from the background fluorescence. Discrete QD counts exhibited square wave shaped On-Off blinking in time-varying intensity profiles, demonstrating detection of single QDs on these transparent PDMS-PVDF membranes.

Figure 22D:
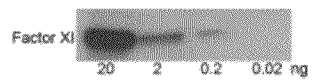

Detection of two different samples of purified, fractionated proteins showed that SPQD Westerns provide a substantial increase in protein detection sensitivity. SPQD Westerns were performed using a polyclonal anti-NGF antibody to detect purified nerve growth factor (NGF), a hormone protein implicated with a number of pathophysiological conditions. SPQD Westerns yielded a detection threshold of 0.01 ng (FIG. 22A), compared to detection of 10 ng by traditional Westerns that were processed using the same membrane blots (FIG. 22B). This was a $10^3$-fold improvement in the sensitivity of SPQD Westerns in comparison to traditional Westerns. SPQD Westerns were also performed using a monoclonal anti-Factor XI antibody that binds to a single epitope site on Factor XI, a protein present at low concentrations in plasma. SPQD Westerns of Factor XI yielded a detection threshold of 0.2 pg (FIG. 22C) compared to detection of 0.2 ng by traditional Westerns (FIG. 22D). Again, this was a $10^3$-fold sensitivity increase in comparing the SPQD Western and traditional Western techniques. SPQD counts for each protein concentration of both Factor XI and NGF were performed over multiple independent trials and yielded values above the background. In particular, for low sample amounts, the number of QD-tagged proteins could be distinguished from the background of non-specifically bound QDs, as seen by values that are consistently located above the x-axis (FIG. 22). A desired sensitivity for the detection of pure protein was 0.2 pg. This translates to a $5 \times 10^3$-fold increase in sensitivity over traditional Westerns performed on the same blots and a $5 \times 10^3$-fold increase in sensitivity over the 1 ng sensitivity limit reported by bulk fluorescence measurements using QD-based Western immunoblots.

The SPQD Western blotting technique was applied to cellular samples and it was found that specific proteins of interest could be detected in as few as 100 cells. SPQD and traditional Westerns were performed to detect the TrkA tyrosine kinase receptor protein, as well as TrkA upregulation induced by exposing PC12 cells with NGF, a TrkA cognate ligand. In SPQD Westerns, TrkA receptor protein could be detected in samples of $10^2$-$10^3$ cells, translating to an amount of 0.05-0.5 µg of total protein (FIG. 23A). Traditional Western immunoblots were performed on samples run in adjacent lanes of the same membrane and required a minimum of $10^5$ cells or 50 µg of protein (FIG. 23B). Cells treated with NGF have an increase in TrkA production, and by using SPQD blotting, a subtle increase in protein production (x1.5-2) for samples as few as 100 cells was detected (FIG. 23C). Traditional Westerns using these same cell lysate samples produced a detectable signal for a sample of $10^5$ cells. Traditional Westerns were also used to detect actin, an abundant protein in these same cell samples. An amount of $10^5$ cells was still required to produce a detectable signal (FIG. 23A). These results demonstrate that SPQD Western immunoblot technology can provide a detectable signal in cell samples of as few as 100 cells. This is a $10^3$-$10^4$-fold improvement over typical ranges of $10^5$-$10^6$ cells used in traditional Westerns and is a $10^2$-fold over QD-based Western immunoblots.

Figure 24A:
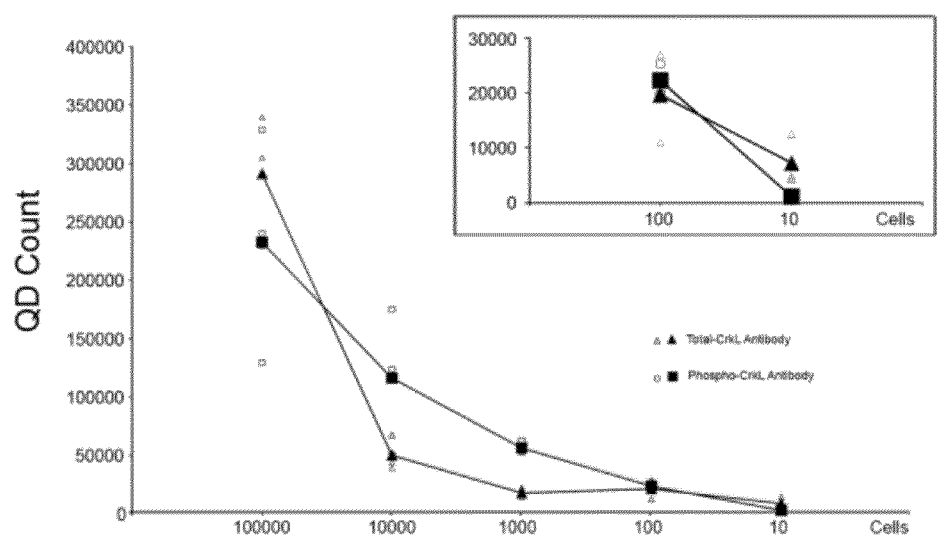
FIG. 24A-B shows detection thresholds for CrkL proteins.
Figure 24B:
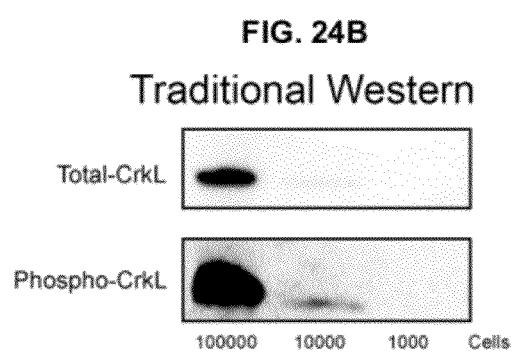

To further verify this level of sensitivity in cellular samples, SPQD and traditional Western blots were performed using a two antibody method in which one antibody detects total CrkL protein and the other detects the phosphorylated form of CrkL protein. CrkL is a direct substrate of the oncogenic tyrosine kinase, BCR-ABL, the causative molecular lesion in chronic myeloid leukemia (CML). Detection of CrkL phosphorylation is the preferred pharmacodynamic assay for CML clinical trials involving new BCR-ABL inhibitors. FIG. 24A shows that the detection threshold of SPQD Westerns for each antibody-protein pair was 100 cells. This SPQD threshold is $10^3$ times greater than traditional Westerns performed with the total-CrkL antibody (FIG. 24B, top), and $10^2$ times greater than traditional Westerns preformed with the phospho-CrkL antibody (FIG. 24B, bottom). While the detectable threshold of SPQD Western blots will vary with the specific antibody and cell sample (e.g. antibody affinity, amount of protein), similar results obtained for the detection of total-CrkL, phospho-CrkL, and TrkA proteins indicate that a threshold value of 100 cells can be regularly obtained.

It is desirable to distinguish whether SPQD counts made on Western immunoblots are composed of single QD or multiple QD tags. Single QDs can be detected on PDMS-PVDF transparent membranes, but during Western immunoblotting, other factors influence QD composition at each detected point of florescence. For example, more than one QD-streptavidin may bind to multiple biotin molecules on a single targeting antibody. Also, multiple targeting antibodies may bind to a single target protein macromolecule (depending on the number of antibody-protein recognition sites). In contrast, QD size and steric hindrance can limit the number of QD tags bound to each antibody-protein complex.

To determine the QD composition of single point counts, the distribution of intensity values for each QD count was analyzed and strict criterion of QD On-Off blinking was used to distinguish single QDs from multiple QDs. Analysis of membranes processed using SPQD Western blotting, both for purified Factor XI protein and cellular phosphorylated CrkL protein show discrete counts of QD fluorescence (FIG. 25A left and right, respectively). Using automated detection, each SPQD count was located and its time-varying intensity profile was plotted. It was found that SPQD counts exhibited three types of intensity profiles, distinguishable from areas on the membrane that did not contain QDs (FIG. 25B, blue background traces). (1.) Intensity profiles containing square wave On-Off blinking indicated a QD point composed of a single QD (FIG. 25B, green trace). (2.) Intensity profiles that did not exhibit clear square wave On-Off blinking but did exhibit intermittent intensity values that returned to a mean background intensity 'Off' state (FIG. 25B, dashed line) indicated a QD count that blinked but was composed of a few QDs (FIG. 25B, purple trace). (3.) The remaining profiles contained low frequency fluctuations that exhibited a wide range of variance, but shared the common characteristic that their intensity profile did not return to the mean background intensity 'Off' state (e.g. compare FIG. 25B, red traces), indicating that the QD point consisted of many QDs and did not blink (FIG. 25B, red trace). Histograms of intensity values reflected the distribution of intensities measured for each profile type (FIG. 25C). Single blinking QDs showed a bimodal distribution of intensity values overlapping background intensity values when in the 'Off' state. QD counts composed of a few QDs showed a distribution of intensities values that were not bimodal-shaped but which overlapped with the histogram of background intensity values. QD counts containing many QDs showed a distribution of intensity values that were located above the mean background intensity. The distinguishing features from these histograms were used to categorize all QD counts into the categories of single, few, and many QDs. The results of this analysis, performed on purified Factor XI (n=1515) and on cellular CrkL protein (n=707) showed that single QDs made up 13.4% and 6.36% of the population of total QD counts. The majority of all QD counts were composed of either a single QD or a few QDs: 72.48% and 78.92%, respectively for Factor XI and phospho-CrkL (see bar graph, FIG. 25D).

The maximum number of QDs in each detected blinking point can be estimated by assuming that each single QD possesses a 50% On-Off duty cycle. This means that on average, n QDs are simultaneously in the Off state for $1/(2^n)$ of the total time. For n=9, all 9 QDs would simultaneously be in the Off state for $1/512$ or 0.2%, of the time. Although this method of blinking analysis is preliminary, it provides an estimate that suggests that a majority of SPQD counts for both Factor XI and cellular phospho-CrkL were composed of 9 QDs or less. In summary, QD fluorescent blinking analysis shows that for SPQD Western blotting of both purified and cellular proteins, detection of single QD tagged-protein is possible and that a majority of detected fluorescence points are associated with single or a few (<9) QDs.

Given that the detection sensitivity of PVDF-membrane bound proteins is that of single QD fluorescent tags, other limiting factors are: 1) the efficiency of protein transfer in the electroblotting process, 2) the affinity of the antibody probe used to detect PVDF-membrane bound proteins, and 3) the accuracy of QD-antibody probe binding and detection. While the efficiency of protein transfer during the electroblotting process will vary depending on the size and charge of the protein, electrotransfer can be extremely efficient under optimized conditions. Notably, the anti-NGF antibody used did not possess remarkably high affinity (a high concentration of 1:500 streptavidin-HRP was needed to achieve optimized detection in our traditional Western immunoblots). Yet, sensitive detection with SPQD blotting was obtained. It might be possible to attain greater levels of sensitivity using even higher-affinity antibodies.

With regard to further increasing the detection sensitivity of SPQD Western blotting, one possibility is the optimization of QD-counting to distinguish protein tagged QDs (signal) from non-specifically bound QDs (noise). A simple approach is to increase the number of sampled regions in a blot band in order to characterize with high-resolution the spatial profile by which proteins gel-fractionate at low sample concentrations (e.g. Gaussian-shaped band vs. a rectangular-shaped blot band). Such a spatial profile may be then used as a template in all lanes to limit the locations in which QD-counts are made. Mapping high-resolution spatial profiles of QD-tagged proteins is feasible as automated scanning and QD counting is very rapid (30 mins for automated blot scanning, 1 min per 200 images for automated counting). One challenge to note is that small changes in z-focus (while scanning distances of approximately 2 mm) need to be reliably corrected to retain and improve accuracy at these lower limits of sensitivity. However, it is suspected that further optimization of SPQD Western immunoblotting along these lines could extend detection sensitivities into the range of sub-femtogram quantities of protein and reduce samples to less than 100 cells.

In one example, QDs were fractionated with high-resolution acrylamide-agarose (2% PA-0.5% AGE) electrophoresis and electroblotted to PVDF membranes. Electrophoresis was performed at 100-150 V for 0.5-1.0 h in 1× TBE running buffer. QD samples were electroblotted to PVDF membranes in 0.5× TBE with 20% methanol under 100V for 1-2 hr.

For SPQD Western immunoblotting, membranes containing fractionated QD bioconjugates (FIG. 21) or incubated with antibody-QD bioconjugates (FIGS. 22-24) were air-dried on glass slides (>2 h). To render membranes transparent, QD-bound PVDF membranes were coated with polydimethyl siloxanes (PDMS). Sylgard 184 silicone elastomer curing agent, a commercially available reagent (Product: 184 SIL ELAST Kit 3.9 kg, Ellsworth Adhesives), was used to make dry PVDF membranes transparent. Sylgard 184 silicone curing agent contains a variety of polydimethyl siloxanes including: dimethyl, methylhydrogen siloxane; dimethylsiloxane dimethylvinyl-terminated; and tetramethyl tetravinyl cyclotetrasiloxane. Other polydimethylsiloxanes such as methyl-terminated polydimethylsiloxane, or the combination of siloxanes present in the base portion of Sylgard 184 elastomer were also effective in converting PVDF for imaging single QDs. To make PVDF membranes transparent, air-dried PVDF membranes were immersed in 1 ml of PDMS in a glass dish for 10 seconds and then plated onto glass slides. Dry PVDF membranes became transparent instantly upon contact with the curing agent; it was desirable that membranes were completely dry. Once membranes were transparent and coated with PDMS, they could be immediately imaged or stored at 4° C. for future use. Macroscopic QD-bound transparent PDMS-PVDF blots were viewed using a UV imaging system (UVP, MultiDoc-It). Microscopic images of PDMS-PVDF membranes were acquired using a fluorescent microscope (Zeiss Axiovert 200M) equipped with 40× and 100× objectives, excitation and emission filters (Chroma), and a cooled monochrome CCD camera (Axiocam). Automated microscope field images were taken using a precise x-y scanning stage (ASI) under software control (AxioVision). The membrane is a 3D object containing proteins, which may penetrate the blot during electrotransfer, and QDs, which may diffuse into the blot during incubation of the membrane with antibody-QD probes. While sectioning the entire 3D membrane blot is possible, this effort provides little gain since the period of membrane electrotransfer can be reduced to deposit the majority of proteins onto the membrane surface. Relative comparisons were made of protein amount across different lanes by analyzing QD-tagged proteins residing at the surface plane of the membrane blot, the location where the majority of QDs were found. To obtain profiles of gel lanes, single counts of QDs were taken along the length of a gel lane starting at the center of the loading well. The position of the bands were located using molecular weight markers (161-0374, Bio-Rad; P7708s, NEB; LC6925, Invitrogen) in either adjacent or in the same lane, as well as by correspondence of macroscopic fluorescence with adjacent well lanes. The same imaging parameters of integration time and band position were applied to all bands in a membrane blot.

QD counts were made from fluorescence images using a custom-written procedure that is based on the algorithm developed by Crocker and Grier, and implemented with the help of publicly available Matlab scripts. CCD-collected fluorescence microscopy images are first conditioned using a spatial bandpass filter characterized by two cutoff feature sizes. The small feature cutoff of the bandpass filter is tuned to reduce pixel noise while the large feature cutoff is adjusted to eliminate inhomogeneous illumination and background fluorescence. A threshold is then applied to the filtered image, leaving only a small region of high intensity corresponding to each particle; the pixel with maximum intensity out of each region is chosen as the preliminary location for that particle. Subsequent processing refines the preliminary locations by finding the centroid of the intensity pattern near the preliminary location. This particle location procedure is carried out on multiple sampled images in each membrane lane, giving refined particle locations that are counted and form an estimate for the number of QD counts per lane for each experiment. This automated QD count algorithm produces 90% accuracy of automated QD counts, as compared to QD counts obtained by human eye on the same images. QD blinking produces negligible error in these automated counts. By noting the locations of all individual QD counts and making accumulated counts over multiple frames in a movie, QDs in an 'Off' state for one image frame will eventually return to their 'On' state in another image frame and can be counted. Comparing counts made from one frame vs. counts made over multiple frames of an entire movie, it was found that QD counts made from single image frames produce an error of 15% of total QD counts under our imaging capture rates. Given that a typical image frame consists of a total of 200 QDs, only 30 QDs/image frame were missed.

Movies of SPQD Western blots were acquired with an Andor iXon camera at 33 frames per second for 500 frames. A total of 6 movies were collected from CrkL SPQD Westerns and 9 movies from Factor XI SPQD Westerns. The detection algorithm designed for automated QD counting was used in each frame to detect the locations of discrete QD counts and an algorithm was created to output all QD count locations for a given number of frames. Pixel intensity values were measured at each QD count location in each frame. To measure background noise in each frame, background pixel intensity values were acquired which were not at QD count locations. Because the background noise varies for each movie, the measurements were normalized using a background subtraction. In each movie, the mean background pixel intensity was calculated and subtracted this value from all QD count measurements and background measurements across frames. For each movie, a baseline threshold was used to distinguish between QD count profiles exhibiting blinking behavior and those which never demonstrated an 'Off' state. Each QD count profile was characterized as consisting of either single, few, or many QDs. QD count profiles exhibiting intermittent intensity values that returned to the baseline threshold, showed square-wave On-Off blinking behavior, and had a bimodal distribution of intensity values were categorized as single QDs. QD count profiles exhibiting intermittent intensity values that returned to the baseline threshold, but did not have a bimodal distribution of intensity values were categorized as a few QDs (n<9). QD count profiles having pixel intensity values only above the baseline threshold were categorized as groups of many QDs.

Serial dilutions of NGF (#1156-NG/CF, R&D Systems) and Factor XI were fractionated using 12% and 8% SDS-PAGE, respectively. Each lane containing protein target was flanked by lanes containing molecular weight markers. Samples were electroblotted onto PVDF membranes and membranes were blocked with 5% BSA in TBS/0.1% Tween20 overnight. Biotinylated anti-NGF (0.1 mg/ml, R&D Systems) and biotinylated anti-Factor XI (6.6 mg/ml) were prepared using previously described biotinylation methods. A mixture containing 20 times the number of moles of biotin as moles of antibody is set on ice overnight and then dialyzed for 3 hours at room temperature; this is expected to produce 3-5 biotins per antibody. *SPOD Blotting of NGF and Factor XI:* anti-NGF-biotin-strep-QD655 probes were made with a molar ratio of anti-NGF to strep-QD655 is 4:1 (0.2 μg/ml anti-NGF and 0.3 nM streptavidin-QD655) and blots were incubated with this probe for 1 hour at room temperature. Factor XI-fractionated membranes were first incubated with 6 μl of 6.4 mg/ml biotinylated Factor XI 1A6 antibody overnight at 4° C. and then followed by incubation with 40 μl of 15 nM streptavidin-QD655 at room temperature. Blots were analyzed by single QD counting. *Traditional Western immunoblotting NGF:* NGF-fractionated membranes were incubated with 2 μg/ml biotinylated anti-NGF for 1 hour. After extensively washing, blots were incubated with streptavidin-HRP (1:1000, #21126, Pierce) for 1 hour. After washing, membranes were immersed into SuperSignal® West Pico Chemiluminescent substrate (#34077, Pierce) for 5 min, and exposed to X-ray film for 3 min. All Western immunoblot assays were optimized to achieve the best detectable signal. *Traditional Western immunoblotting Factor XI:* Purified Factor XI was loaded into the stacking gel without β-mercaptoethanol. Gels were run at 100V until samples reached the resolving gel and then run at 125V until the first ladder marker reached the bottom (7 kD, P7708s, NEB). Electroblotted samples were blocked, incubated overnight with 6 μl of 6.4 mg/ml biotinylated Factor XI 1A6 antibody at 4° C., washed, blocked again, and then incubated with streptavidin-HRP (1:5000) for 1.5 hours at room temperature. Blots were then washed and exposed to X-ray film for 2-10 seconds.

PC12 cells were stimulated with NGF (100 ng/ml, R&D Systems, #1156-NG/CF) for 1 hour. Whole cell extracts were prepared with lysis buffer (50 mM Tris-HCl, pH7.4, 150 mM NaCl, 1%NP-40, 0.1% Sodium deoxycholate, 4 mM EDTA) supplemented with protease inhibitor cocktail (#P2714-1BTL Sigma). Insoluble materials were removed from the protein extract by centrifugation at 13,000 rpm for 15 min. Serial diluted cell lysates were mixed with 1× laemmli sample buffer (#161-0737,Bio-Rad) and denatured (95° C., 5 min). Lysates were separated with 8% SDS-PAGE. Samples were loaded into gels with flanking lanes containing molecular weight markers. Extracts from control (no NGF stimulation) cells were run in parallel as a control. After electroblotting onto to PVDF membranes, membranes were blocked with 5% BSA in TBST overnight. *SPOD blotting of TrkA:* Blots were incubated with anti-TrkA-biotin-strep-QD655s (4 anti-TrkA Ab:1 strep-QD655 molar ratio, 0.2 μg/ml anti-TrkA and 0.3 nM strep-QD655) for 1 hour, or anti-β-actin -biotin-strep-QD655s (1 anti-β-actin Ab:1 strep-QD655, molar ratio, 0.0045 μg/ml anti-β-actin, 0.03 nM strep-QD655) for 1 hour. Blots were analyzed by single QD counting (see above). *Traditional Western immunoblotting of TrkA:* Blots were incubated with biotinylated anti-TrkA antibody (4 μg/ml, sc-11, C-14, Santa Cruz) for 1 h, or with control biotinylated β-actin antibody (0.01 μg/ml, #4967, Cell Signaling) for 1 h. After extensive washing, blots were incubated with streptavidin-HRP (1:5000) for 1 h. Membranes were immersed into SuperSignal® West Pico Chemiluminescent substrate for 5 min, then exposed to X-ray film for 3 min.

Serially diluted imatinib-treated Mo7e/p210 cellular lysate (starting concentration: $10^5$ per 20 μl) was loaded into 4 identical pre-cast 4-15% Criterion Tris-glycine gels. Each gel was run at 200V for 1 hour, until the first ladder band reached the gel bottom (4 kD, LC6925, Invitrogen). Samples were electroblotted to PVDF membranes at 95V for 1 hour and then blocked overnight in 3% BSA in TBST overnight at 4° C. *SPOD blotting of CrkL and phospho-CrkL:* One membrane was incubated with 10 ml of biotinylated anti-CrkL (1:2500 in 3% BSA/TBST) and another membrane was incubated with 10 ml of biontinylated anti-phospho-CrkL (1:2500 in 3% BSA/TBST), both at 4° C. for 2 hours. Both membranes were washed and then incubated with 200 μl of 1 nM strep-QD655 for 1 hour at room temperature. Blots were analyzed by single QD counting (see above). *Traditional Western immunoblotting of CrkL and phospho-CrkL:* One membrane was incubated with 25 ml of anti-CrkL (1:2500 in 3% BSA/TBST) and another membrane was incubated with 25 ml of biontinylated anti-phospho-CrkL (1:2500 in 3% BSA/TBST), both at 4° C. overnight. For both membranes 15 second exposures were obtained using a Lumi Imager (Roche).

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

We claim:

1. A method for counting biomolecules in a sample comprising:
    labeling the biomolecules in the sample with a nanoparticle probe comprising a detectable nanoparticle;
    providing the labeled biomolecules on a transparent base material;
    automatically counting the nanoparticles including;
        automatically capturing an image of the nanoparticles;
        automatically detecting nanoparticles that have fluoresced on the image; and
        maintaining a count of discrete groups of nanoparticle probes or single nanoparticle probes, wherein counting the nanoparticles is considered counting of the target biomolecules;
    performing blinking analysis of nanoparticle fluorescence including:
        capturing a movie of an x-y location of the transparent base material;
        detecting nanoparticle fluorescence in each frame of the captured movie;
        maintaining a movie-based count of detected nanoparticle fluorescence over each frame in the captured movie to obtain an accurate total count of each detected nanoparticle and a time-varying intensity trace of each detected nanoparticle fluorescence;
        detecting background intensity values over each frame of the captured movie to obtain a time-varying background intensity trace;
        binning intensity values of the time-varying background intensity trace to obtain a distribution of background intensity values; and
        for each detected nanoparticle fluorescence:
            binning intensity values of the time-varying intensity trace of the detected nanoparticle fluorescence to obtain a distribution of intensity values associated with the nanoparticle fluorescence; and
            characterizing a nanoparticle population composition of the detected nanoparticle fluorescence based on an amount of overlap of the distribution of intensity values associated with the nanoparticle with the distribution of background intensity values and mean intensity values of the detected nanoparticle fluorescence.

2. The method of claim 1, further including:
    positioning the transparent base material on a stage that can move the transparent base material in at least an X-Y plane;
    automatically moving the transparent base material through multiple predetermined locations using the stage;
    capturing an additional image at each predetermined location;
    automatically detecting nanoparticles for each additional image; and
    adding a number of detected nanoparticles for each additional image to the count.

3. The method of claim 1, further including adding an error factor to the count.

4. The method of claim 3, wherein the count is an image-based count and further including determining the error factor by capturing a movie of a single x-y location of the transparent base material, maintaining a movie-based count of detected nanoparticles over each frame in the captured movie, and comparing the movie-based count to the image-based count.

5. The method of claim 4, further including binning the detected nanoparticles so that detected nanoparticles that are separated by less than a predetermined distance are considered the same nanoparticle.

6. The method of claim 1, wherein the transparent base material is a membrane or a glass slide.

7. The method of claim 1, wherein the biomolecules comprise proteins and the method further comprises electrophoresing the sample, transferring proteins in the sample to an opaque or translucent base material, and converting the base material to the transparent base material.

8. The method of claim 1, wherein the biomolecules comprise proteins and the method further comprises transferring proteins in the sample, which were not electrophoresed, onto an opaque or translucent base material and converting the base material to the transparent base material.

9. The method of claim 1, wherein the biomolecules comprise proteins and the proteins in the sample are in a protein array and the transparent base material is a glass slide.

10. The method of claim 1, wherein the base material is an opaque polyvinylidene fluoride (PVDF) membrane, and further including making the base material transparent by immersing the opaque PVDF membrane in a mixture containing polydimethylsiloxane.

11. The method of claim 1, further including filtering the image using a spatial bandpass filter that eliminates detection of features that are sized below a lower threshold and sized above an upper threshold.

12. The method of claim 1, wherein automatically detecting nanoparticles includes:
    applying an intensity threshold to a region encompassing the detected nanoparticle;
    choosing a pixel within the region with a maximum intensity; and
    determining a centroid of an intensity pattern around the chosen pixel.

13. The method of claim 1,
    wherein characterizing the nanoparticle population composition of the detected nanoparticle fluorescence comprises:
    characterizing the detected nanoparticle fluorescence as a single nanoparticle if it exhibited intermittent intensity values that returned to a baseline value, the distribution of intensity values associated with the nanoparticle fluorescence and the distribution of background intensity values overlap, and the overlap of the distribution of intensity values associated with the nanoparticle fluorescence with the distribution of background intensity values forms a bimodal distribution of intensity values;
    characterizing the nanoparticle fluorescence as several nanoparticles if it exhibited intermittent intensity values that returned to the baseline value, the distribution of intensity values associated with the nanoparticle fluorescence and the distribution of background intensity values overlap, and the overlap of the distribution of intensity values associated with the nanoparticle fluorescence with the distribution of background intensity values does not form a bimodal distribution of intensity values; and characterizing the nanoparticle fluorescence as a group of nanoparticles if mean intensity values of the detected nanoparticle fluorescence remain above the baseline value and the distribution of intensity values associated with the nanoparticle fluorescence and the distribution of background intensity values do not overlap.

14. The method of claim 1, wherein the nanoparticles are quantum dots.

15. A method for counting quantum dots coupled to proteins, comprising:
(a) providing a transparent membrane containing quantum dots bound to proteins;
(b) automatically moving the transparent membrane to an X-Y coordinate suitable for image capturing;
(c) projecting an excitation light onto the membrane;
(d) capturing an image of emission light from the quantum dots using a camera;
(e) detecting quantum dots on the image;
(f) capturing a movie using the camera while projecting excitation light onto the membrane;
(g) for each frame of the captured movie and for each quantum dot detected on the image:
detecting quantum dot intensity values for a region encompassing the detected quantum dot to obtain a time-varying intensity trace and an accumulated, updated record of newly detected quantum dots for the same region;
(h) detecting background intensity values on each frame of the captured movie to obtain a time-varying background intensity trace;
(i) binning intensity values of the time-varying background intensity trace to obtain a distribution of background intensity values; and
(j) for each detected quantum dot:
binning intensity values of the time-varying intensity trace of the detected quantum dot to obtain a distribution of intensity values associated with the detected quantum dot; and
characterizing a quantum dot population of the detected quantum dot based on an amount of overlap of the distribution of intensity values associated with the quantum dot with the distribution of background and mean intensity values of the detected quantum dot; and
(k) automatically counting the quantum dots based on the quantum dot population characterization of each quantum dot to obtain a quantum dot count.

16. The method of claim 14, further including repeating (b), (c), (d), (e), (f), (g), (h), (i), j), and (k) for multiple X-Y coordinates to obtain a plurality of images and wherein automatically counting the quantum dots includes summing the quantum dots over multiple images to obtain the quantum dot count.

17. The method of claim 13, wherein characterizing the nanoparticle fluorescence as several nanoparticles comprises characterizing the nanoparticle fluorescence as including a number of at least two nanoparticles but less than approximately 9 nanoparticles, and characterizing the nanoparticle fluorescence as a group of nanoparticles comprises characterizing the nanoparticle fluorescence as including a number greater than or substantially equal to approximately 9 nanoparticles.

* * * * *